US008623351B2

(12) United States Patent
Anversa et al.

(10) Patent No.: US 8,623,351 B2
(45) Date of Patent: Jan. 7, 2014

(54) COMPOSITIONS COMPRISING VASCULAR AND MYOCYTE PROGENITOR CELLS AND METHODS OF THEIR USE

(75) Inventors: Piero Anversa, Boston, MA (US); Annarosa Leri, Boston, MA (US); Jan Kajstura, Brookline, MA (US)

(73) Assignee: New York Medical College, Valhalla, NY (US)

(*) Notice: Subject to any disclaimer, the term of this patent is extended or adjusted under 35 U.S.C. 154(b) by 0 days.

(21) Appl. No.: 13/365,072

(22) Filed: Feb. 2, 2012

(65) Prior Publication Data

US 2012/0207714 A1    Aug. 16, 2012

Related U.S. Application Data

(63) Continuation of application No. 12/325,776, filed on Dec. 1, 2008, now Pat. No. 8,119,123.

(60) Provisional application No. 60/991,515, filed on Nov. 30, 2007.

(51) Int. Cl.
*A61K 35/34* (2006.01)
*A61K 38/19* (2006.01)

(52) U.S. Cl.
USPC .......................... 424/93.7; 424/93.1; 435/325

(58) Field of Classification Search
USPC .................. 424/93.7, 93.1; 435/325
See application file for complete search history.

(56) References Cited

U.S. PATENT DOCUMENTS

| | | | |
|---|---|---|---|
| 5,434,134 A | 7/1995 | Gluckman et al. | |
| 5,908,782 A | 6/1999 | Marshak et al. | |
| 6,036,972 A | 3/2000 | Nakamura et al. | |
| 6,387,369 B1 | 5/2002 | Pittenger et al. | |
| 2003/0054973 A1 | 3/2003 | Anversa | |
| 2004/0258669 A1 | 12/2004 | Dzau et al. | |
| 2005/0170506 A1 | 8/2005 | Sayre et al. | |
| 2006/0239983 A1 | 10/2006 | Anversa | |
| 2006/0263337 A1 | 11/2006 | Maziarz et al. | |
| 2007/0054397 A1 | 3/2007 | Ott et al. | |
| 2009/0143296 A1 | 6/2009 | Anversa | |
| 2009/0157046 A1 | 6/2009 | Anversa | |
| 2009/0162329 A1 | 6/2009 | Anversa et al. | |
| 2009/0169525 A1 | 7/2009 | Anversa et al. | |
| 2009/0180998 A1 | 7/2009 | Anversa et al. | |

FOREIGN PATENT DOCUMENTS

| | | |
|---|---|---|
| JP | 11-246433 | 9/1999 |
| WO | WO 92/11865 | 7/1992 |
| WO | WO 95/28174 | 10/1995 |
| WO | WO 99/45775 | 9/1999 |
| WO | WO 99/47163 A | 9/1999 |
| WO | WO 99/49015 A | 9/1999 |
| WO | WO 01/26694 | 4/2001 |
| WO | WO 01/34179 | 5/2001 |
| WO | WO 01/94420 | 12/2001 |
| WO | WO 02/13760 A | 2/2002 |
| WO | WO 03/033678 A | 4/2003 |
| WO | WO 03/103611 A | 12/2003 |
| WO | WO 2005/012510 A1 | 2/2005 |
| WO | WO 2006/045331 A | 5/2006 |
| WO | WO 2007/100530 A1 | 9/2007 |
| WO | WO 2008/058216 A | 5/2008 |
| WO | WO 2009/073594 A | 6/2009 |

OTHER PUBLICATIONS

Young et al., "Mesenchymal Stem Cells Reside Within the Connective Tissues of Many Organs." *Developmental Dynamics* 1995. vol. 202 pp. 137-144.
Nakamura et al., "Myocardial protection from ischemia/reperfusion injury by endogenous and exogenous HGF." *J. Clin. Invest.* 2000, vol. 106, pp. 1511-1519.
Yamamura et al., "IGF-1 differentially regulates Bcl-xL and Bax and confers myocardial protection in the rat heart." *Am. J. Physiol. Heart Circ. Physiol.* 2001, vol. 280, pp. H1191-H1200.
Segers et al., "Stem-cell therapy for cardiac disease." *Nature* 2008, vol. 451, pp. 937-942.
International Search Report Based on International Application No. PCT/US08/085108 (Apr. 28, 2009).
International Search Report Based on International Application No. PCT/US08/084877 (Apr. 7, 2009).
Torella et al., "Biological properties and regenerative potential, in vitro and in vivo, of human cardiac stem cells isolated from each of the four chambers of the adult human heart" Circulation, vol. 114, No. 18, suppl: 87, 2006.
Bearzi et al., "Human cardiac stem cells" Proc. Natl. Acad. Sci. USA, vol. 104: 14068-14073, 2007.
Messina et al., "Isolation and expansion of adult cardiac stem cells from human and murine heart" Circulation Research, vol. 95: 911-921, 2004.
Linke et al., "Stem cells in the dog heart are self-renewing, clonogenic, and multipotent and regenerate infarcted myocardium, improving cardiac function" Proc. Natl. Acad. Sci. USA, vol. 102: 8966-8971, 2005.
Beltrami et al., "Adult cardiac stem cells are multipotent and support myocardial regeneration" Cell, vol. 114: 763-776, 2003.

(Continued)

*Primary Examiner* — Taeyoon Kim
(74) *Attorney, Agent, or Firm* — Cooley LLP

(57) ABSTRACT

The invention provides compositions of adult cardiac vascular progenitor cells (VPCs) and adult cardiac myocyte progenitor cells (MPCs) useful for the treatment of various cardiac conditions. The invention also encompasses methods of generating a biological bypass, repairing damaged myocardium, and treating or preventing hypertensive cardiomyopathy and heart failure with the compositions of the invention. Methods of isolating the cardiac progenitor cells are also disclosed.

32 Claims, 25 Drawing Sheets

(56) References Cited

OTHER PUBLICATIONS

Dawn et al., "Cardiac stem cells delivered intravasculary traverse the vessel barrier, regenerate infarcted myocardium, and improve cardiac function" Proc. Natl. Acad. Sci. USA, vol. 102: 3766-3771, 2005.

Urbanek et al., "Cardiac stem cells possess growth factor-receptor systems that after activation regenerate the infarcted myocardium, improving ventricular function and long-term survival" Circulation Research, vol. 97: 663-673, 2005.

Urbanek et al., "Myocardial regeneration by activation of multipotent cardiac stem cells in ischemic heart failure" Proc. Natl. Acad. Sci. USA, vol. 102: 8692-8697, 2005.

Urbanek et al., "Intense myocyte formation from cardiac stem cells in human cardiac hypertophy" Proc. Natl. Acad. Sci. USA, vol. 100: 10440-10445, 2003.

Anversa et al., "Life and death of cardiac stem cells-A paradigm shift in cardiac biology" Circulation, vol. 113: 1451-1463, 2006.

Sussman et al., "Myocardial aging and senescence: Where have the stem cells gone?" Annual Review of Physiology, vol. 66: 29-48, 2004.

Armandola, Written Opinion of International Search Authority for PCT/US08/084877, Apr. 2009.

Pêche et al., "Prolongation of Heart Allograft Survival by Immature Dendritic Cells Generated from Recipient Type Bone Marrow Progenitors", *American Journal of Transplantation*, Feb. 2005, vol. 5, No. 2, pp. 255-267.

Metcalfe et al., "Transplantation tolerance: gene expression profiles comparing allotolerance vs. allorejection", *International Immunopharmacology*, Jan. 2005, vol. 5, No. 1, pp. 33-39.

Orlic et al., "Mobilized bone marrow cells repair the infarcted heart, improving function and survival", Proc. Natl. Acad. Sci. USA, vol. 98: 10344-10349, 2001.

Beltrami et al., "Adult cardiac stem cells are multipotent and support myocardial regeneration", *Cell*, Sep. 19, 2003, 114(6):763-776.

International Search Report based on International Application PCT/US2008/085163 (Oct. 14, 2009).

Baba et al., "Flk I+ cardiac stem/progenitor cells derived from embryonic stem cells improve cardiac function in a dilated cardiomyopathy mouse model", *Cardiovascular Research*, 2007; 76:119-131.

Leri et al., "Heart failure and regenerative cardiology", *Regenerative Medicine*, 2006, 1(2):153-159.

International Search Report based on International Application PCT/US2008/085158 (Jan. 11, 2010).

Figure 11

Genes Increased in Bone Marrow Stem Cells

| Gene Title | Relevance | Fold Increase | p-value | Probe |
|---|---|---|---|---|
| chitinase 3-like 3 & 4 | Mast cells and macrophages | 4390 | 0.00002 | 1425451_s_at |
| CD177 antigen | Neutrophil alloantigen | 3327 | 0.00002 | 1424509_at |
| lactotransferrin | Component of innate immunity | 1351 | 0.00002 | 1450009_at |
| lipocalin 2 | Neutrophil gelatinase-associated lipocalin precursor | 1024 | 0.00002 | 1427747_a_at |
| interferon induced transmembrane protein 6 | Fragilis5 / restricted to immune cells | 891 | 0.00002 | 1440865_at |
| ficolin B | Macrophage-associated protein | 776 | 0.00002 | 1430060_at |
| olfactomedin 4 | Found during myeloid differentiation | 128 | 0.00002 | 1437060_at |
| growth differentiation factor 3 | Similar to bone morphogenic proteins | 64 | 0.00002 | 1449288_at |
| poly(A)-specific ribonuclease (deadenylation nuclease) | Enhances neuronal differentiation in neuroblastoma cells | 56 | 0.000023 | 1456658_at |
| Hemopoietic cell kinase | Upregulated during myeloid differentiation | 45 | 0.001336 | 1446553_at |

Genes Increased in Cardiac Stem Cells

| Gene Title | Relevance | Fold Increase | p-value | Probe |
|---|---|---|---|---|
| nuclear receptor subfamily 2, group F, member 1 | Controls Notch regulation in hair cell differentiation | 3104 | 0.000046 | 1418157_at |
| forkhead box C2 | Implicated in lymphatic morphogenesis | 2048 | 0.00002 | 1416693_at |
| paternally expressed 3 | Downstream effector of p53 inhibition of myogenesis | 1783 | 0.00002 | 1417355_at |
| protein tyrosine phosphatase, receptor type, K | Correlated to reduced keratinocyte proliferation | 1663 | 0.000023 | 1444763_at |
| oncostatin M receptor | Pivotal in hepatocyte differentiation | 1552 | 0.000078 | 1416674_at |
| tyrosinase-related protein 1 | Integral during melanocyte differentiation | 1552 | 0.000035 | 1439409_x_at |
| WW domain containing transcription regulator 1 | Beta-catenin-like / regulates mesenchymal differentiation | 1552 | 0.000052 | 1456655_at |
| cysteine rich protein 61 | Ccn1 / associated with development/stimulated by Wnt | 1448 | 0.00002 | 1442340_x_at |
| Cd200 antigen | Mox1 / Expressed before to MyoD during differentiation | 1351 | 0.00002 | 1448788_at |
| kit ligand | SCF | 1261 | 0.00002 | 1448117_at |
| desmoglein 2 | Required for normal ES cell proliferation | 1176 | 0.00002 | 1426153_a_at |
| Wilms tumor homolog | Possibly regulates nestin during cardiac development | 1024 | 0.00002 | 1425995_s_at |

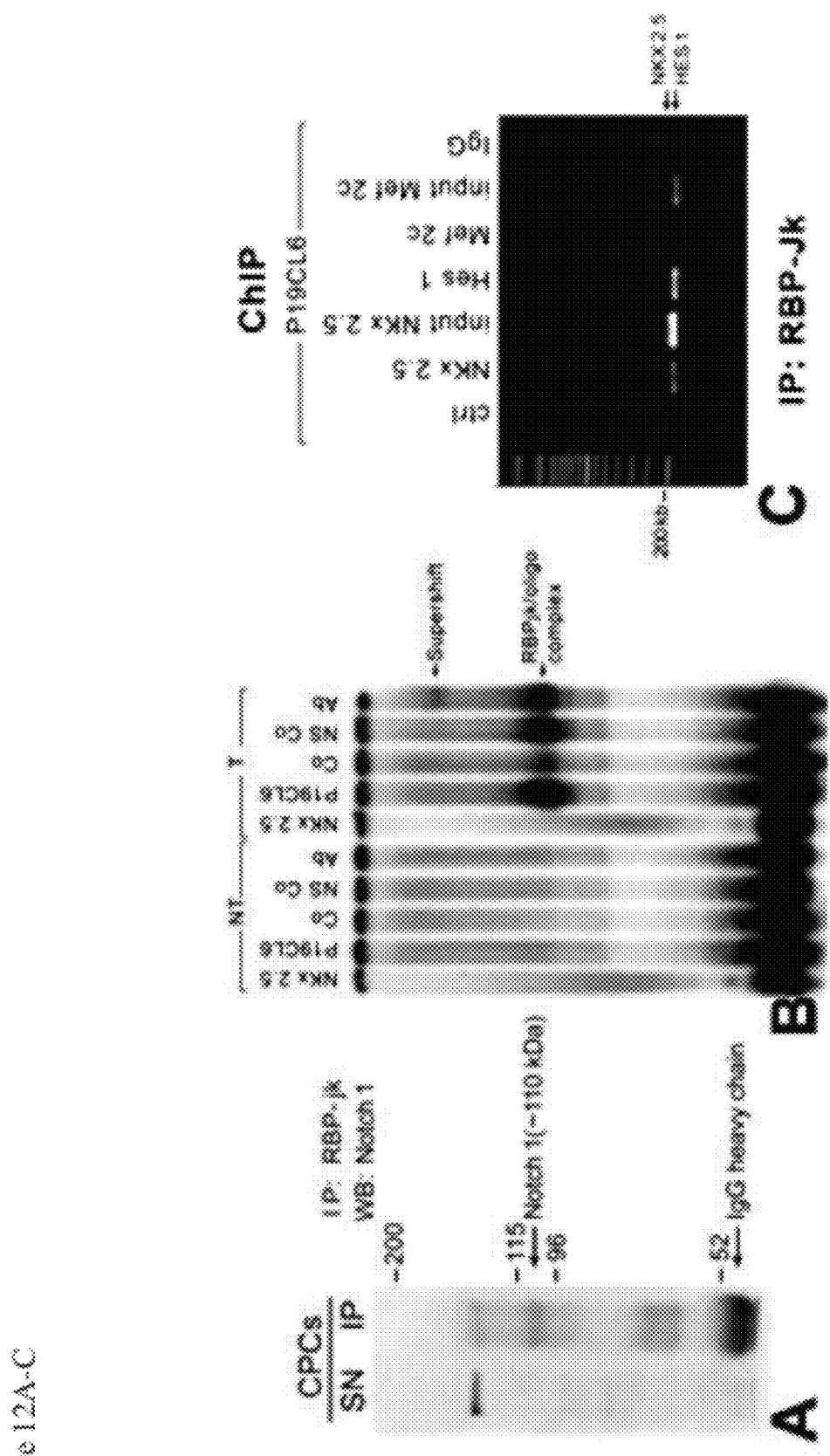
Figure 12A-C

Figure 12D-F
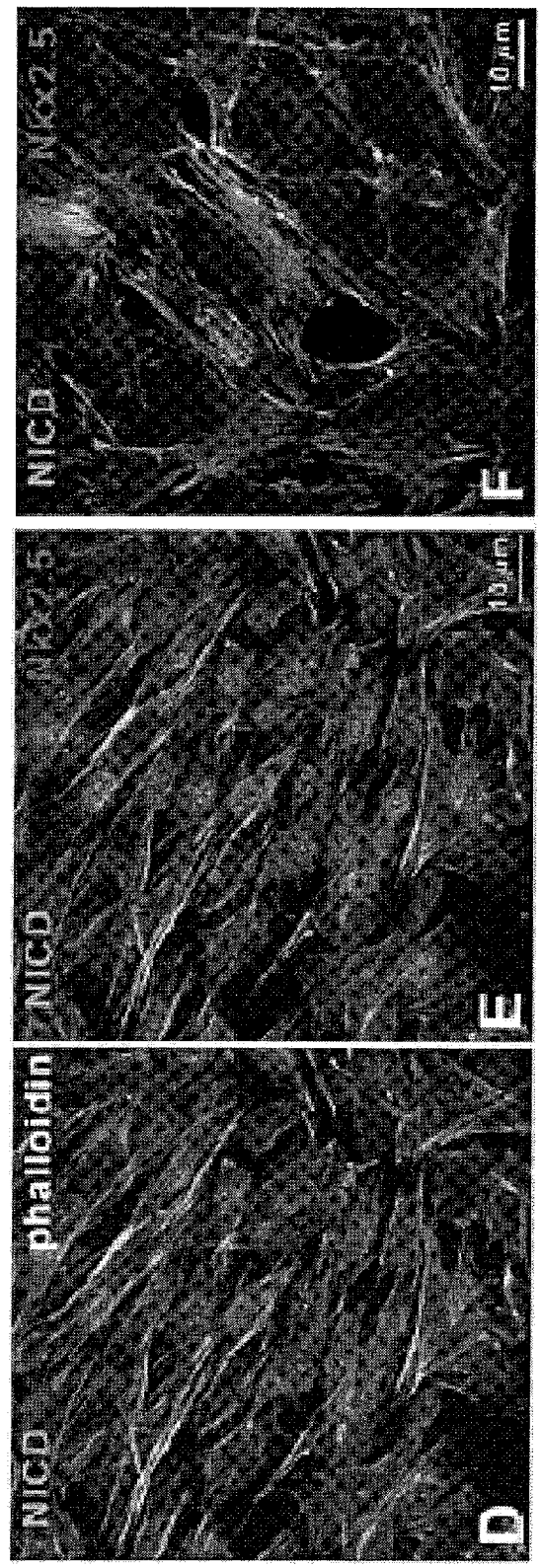

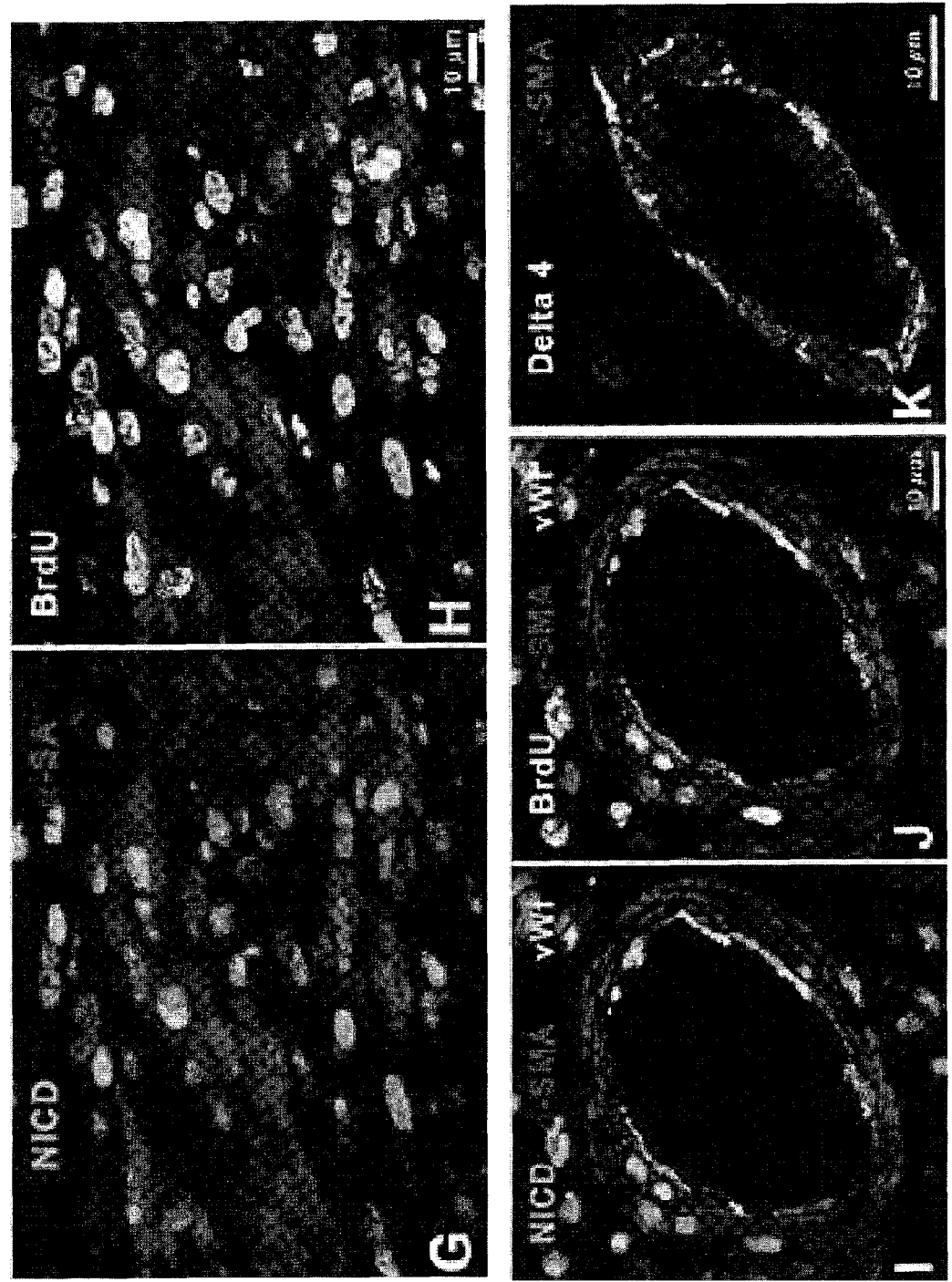
Figure 12G-K

Figure 20
A
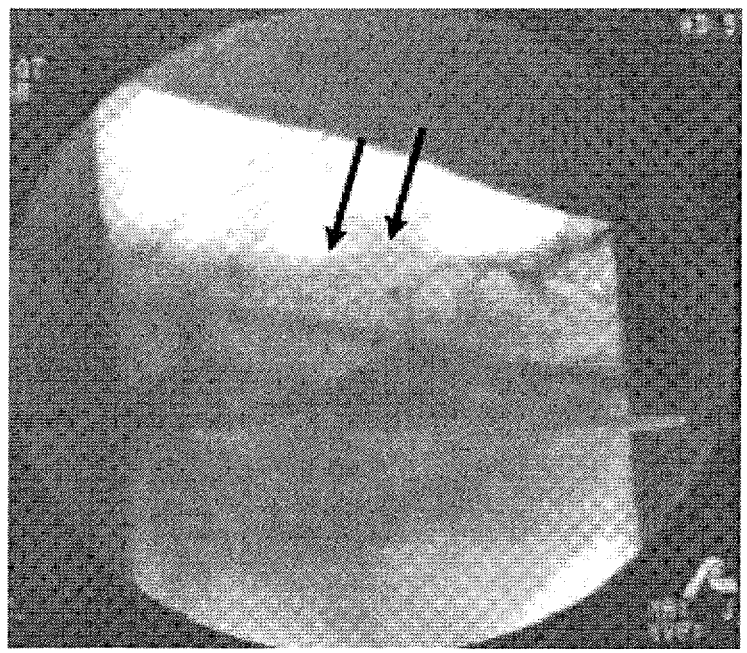
B
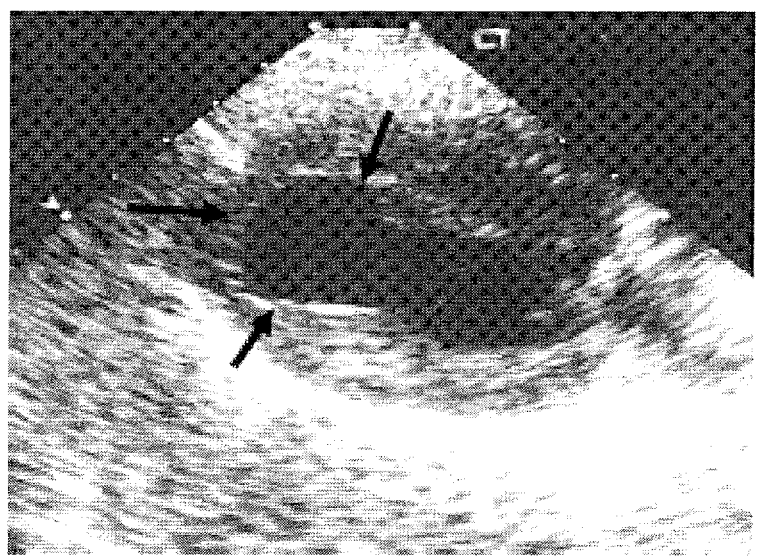

COMPOSITIONS COMPRISING VASCULAR AND MYOCYTE PROGENITOR CELLS AND METHODS OF THEIR USE

CROSS REFERENCE TO RELATED APPLICATIONS

This application is a continuation of U.S. patent application Ser. No. 12/325,776, filed Dec. 1, 2008, which claims the benefit of U.S. Provisional Application No. 60/991,515, filed Nov. 30, 2007, both of which are herein incorporated by reference in their entirety.

FIELD OF THE INVENTION

The present invention relates generally to the field of cardiology, and more particularly relates to compositions of cardiac progenitor cells or cardiac stem cells and methods of using the compositions for repairing damaged myocardium and/or generating a biological coronary bypass.

BACKGROUND OF THE INVENTION

Acute and chronic post-infarction ischemic heart failure in humans is characterized by myocardial regeneration which is limited to the myocyte compartment of the surviving myocardium (259-270). Additionally, small areas of spontaneous myocardial regeneration which invade the infarct shortly after the ischemic event have been identified (267). In addition to the loss in muscle mass, the coronary vasculature remains defective and the extent and regulation of myocardial perfusion are severely impaired (271-281). Alterations in the balance between oxygen demand and supply have been viewed for a long time as critical determinants of the evolution of the ischemic myopathy (282). Pathology of the coronary circulation together with humoral, mechanical and biochemical factors sustain the ischemic myopathy and condition its unfavorable progression to terminal failure (283-288).

Despite advances in understanding the etiology of coronary artery disease (CAD) together with early diagnosis of pre-clinical atherosclerotic lesions and treatment of conventional risk factors, cardiovascular disease continues to be the leading cause of death in the industrialized world (289). Coronary atherosclerosis is the result of the evolving and complex interplay of endothelial injury, inflammatory mediators and the accumulation of oxidized lipids within the arterial wall (290-292). The presence of pro-inflammatory and anti-inflammatory cytokines mediates the cross-talk between the injured endothelial cells and the constituents of the vessel wall which condition the progression of the atherosclerotic plaque (292-296). The site of coronary artery stenosis is characterized by a large fibrous cap, a small lipid core and calcification; vessel pathology typically shows inward growth and narrowing of the lumen. Conversely, non-constrictive coronary atherosclerosis manifests itself with a lipid deposition and a thin fibrous cap without a change in vessel luminal diameter (291). However, it is the latter which is commonly involved in the initiation of an acute coronary syndrome triggered by thrombosis secondary to plaque rupture or erosion (297-299). More than 50% of these events occur in the proximal portion of the epicardial coronary arteries (300) resulting in sudden death, myocardial infarction or ischemic cardiomyopathy.

SUMMARY OF THE INVENTION

One objective of the invention is to interfere with the evolution of coronary artery disease by regenerating the various portions of the coronary circulation together with cardiomyocytes through the delivery of resident cardiac progenitor cells (PCs) capable of differentiating into vascular endothelial cells (ECs), smooth muscle cells (SMCs) and cardiomyocytes. The inventors have surprisingly discovered two subsets of cardiac PCs: vascular progenitor cells and myocyte progenitor cells. Vascular progenitor cells are c-kit positive and flk1 positive and predominantly differentiate into ECs and SMCs. Myocyte progenitor cells are c-kit positive and flk1 negative and predominantly differentiate into cardiomyocytes.

The present invention provides compositions, including pharmaceutical compositions, of adult cardiac progenitor cells useful for the treatment of various cardiac conditions. In one embodiment of the invention, the pharmaceutical composition comprises adult vascular progenitor cells and a pharmaceutically acceptable carrier, wherein the vascular progenitor cells are lineage negative, c-kit positive, and flk1 positive. In another embodiment, the pharmaceutical composition further comprises adult myocyte progenitor cells, wherein the myocyte progenitor cells are lineage negative, c-kit positive, and flk1 negative. The vascular progenitor cells and myocyte progenitor cells may be isolated from human myocardium or myocardial vessels. In some embodiments, the ratio of vascular progenitor cells to myocyte progenitor cells in the composition can be varied to optimize cell therapy treatment for a particular condition or a particular patient. In a preferred embodiment, the ratio of vascular progenitor cells to myocyte progenitor cells is about 1:1.

The present invention also provides a method for generating a biological bypass in a subject in need thereof. In one embodiment, the method comprises obtaining myocardial tissue from the subject; extracting vascular progenitor cells from said myocardial tissue; expanding said vascular progenitor cells in culture; and administering said vascular progenitor cells to a stenotic or occluded artery in the subject's heart, wherein the vascular progenitor cells differentiate into endothelial cells and/or smooth muscle cells, thereby forming coronary vessels that reestablish blood flow to the myocardium. The coronary vessels may include coronary arteries, arterioles, and capillaries with diameters ranging from about 6 µm to about 2 mm.

The present invention also encompasses a method for restoring structural and functional integrity to damaged myocardium in a subject in need thereof. In one embodiment, the method comprises obtaining myocardial tissue from the subject; extracting vascular progenitor cells from said myocardial tissue; expanding said vascular progenitor cells in culture; and administering said vascular progenitor cells to the damaged myocardium, wherein the vascular progenitor cells differentiate into endothelial cells and smooth muscles cells forming functional coronary vessels, thereby increasing blood flow to the damaged myocardium. In another embodiment, the method further comprises extracting myocyte progenitor cells from said myocardial tissue, expanding said myocyte progenitor cells in culture; and administering said myocyte progenitor cells to the damaged myocardium, wherein the myocyte progenitor cells differentiate into cardiomyocytes forming functional myocardium, thereby increasing contractile function. The myocyte progenitor cells may be administered simultaneously with the vascular progenitor cells or after a particular time interval.

The present invention also provides a method for treating or preventing hypertensive cardiomyopathy in a subject in need thereof comprising administering a pharmaceutical composition comprising vascular progenitor cells and myocyte progenitor cells to the subject's heart, wherein the vascular progenitor cells and myocyte progenitor cells engraft in said subject's heart, thereby repopulating diminished progenitor cell niches or forming new progenitor cell niches. In one embodiment, the vascular progenitor cells and myocyte progenitor cells are autologous. In another embodiment, the probability of the subject having heart failure is reduced following administration of the pharmaceutical composition.

The present invention includes a method for treating or preventing heart failure in a subject in need thereof. In one embodiment, the method comprises obtaining myocardial tissue from the subject; extracting vascular progenitor cells from said myocardial tissue; expanding said vascular progenitor cells in culture; and administering said vascular progenitor cells to the subject's heart, wherein the vascular progenitor cells differentiate into endothelial cells and smooth muscles cells forming functional coronary vessels, thereby increasing cardiac function. In another embodiment, the method further comprises extracting myocyte progenitor cells from said myocardial tissue, expanding said myocyte progenitor cells in culture; and administering said myocyte progenitor cells to the damaged myocardium, wherein the myocyte progenitor cells differentiate into cardiomyocytes forming functional myocardium, thereby increasing cardiac function.

BRIEF DESCRIPTION OF THE DRAWINGS

FIG. 11. Transcriptional profile of BMPCs and MPCs. Freshly isolated BMPCs and MPCs were compared. The spectrum of transcripts was similar in the two cell populations with the exception of mRNA for proteins specific of myeloid cells, mast cells and macrophages which were expressed in BMPCs and mRNA for genes involved in proliferation and differentiation of cells of mesodermal and ectodermal origin which were expressed in MPCs. Genes and fold-increases are indicated.

FIG. 12. Notch signaling in MPCs. A: As shown by immunoprecipitation (IP), the intracellular domain of Notch1 and RBP-Jk form a complex in MPCs. SN: supernatant used as negative control. B, C: RBP-Jk binding to the promoter of Nkx2.5. B: Gel-shift assay: arrows indicate the position of the RBPJk-shifted and supershifted bands. Co, unlabeled self-oligonucleotide; NS Co, unlabeled non-specific oligonucleotide; Ab: RBP-Jk antibodies; Nkx2.5: oligonucleotide only. C: ChIP: arrows indicate the position of the PCR product representing the Nkx2.5 promoter. DNA templates were obtained from a protein-DNA complex immunoprecipitated with RBP-Jk-specific antibody (Nkx2.5) or IgG only (IgG). Hes1 promoter was used as positive control and MEF2C promoter as negative control. Input: Genomic DNA without immunoprecipitation. CTRL: control with no template. D, E: Mouse MPCs following the activation of the Notch receptor express the Notch intracellular domain (D, NICD: green) in their nuclei. NICD-positive MPCs express Nkx2.5 (E: magenta). F: Treatment with γ-secretase inhibitor which blocks the Notch signaling, markedly attenuates the nuclear accumulation of NICD and expression of Nkx2.5. G, H: In infarcted mice, numerous small myocytes are positive for NICD (G: green) and BrdU (H: white). 1, J: Newly formed vessels in infarcted heart: SMCs (α-SMA: red) and ECs (vWF: yellow) express NICD (I: green) and are positive for BrdU white). K: The Notch ligand Delta-4 accumulates in the wall of regenerated vessels.

FIG. 20. A. During occlusion of the LAD using the hydraulic occluder, injection of contrast did not appear in the distal LAD circulation in 2 of the dogs (i.e. there was little collateral blood flow), whereas there was a substantial and obvious appearance of contrast in the distal circulation in the one dog receiving VPCs (evidence of a newly developed circulation) as shown above in A by the dark arrows. B. Ligation resulted in apical wall thinning and paradoxical motion (see arrows). Thus, we have created a model of a large infarct accompanied by heart failure.

DETAILED DESCRIPTION OF THE INVENTION

Figure 1:
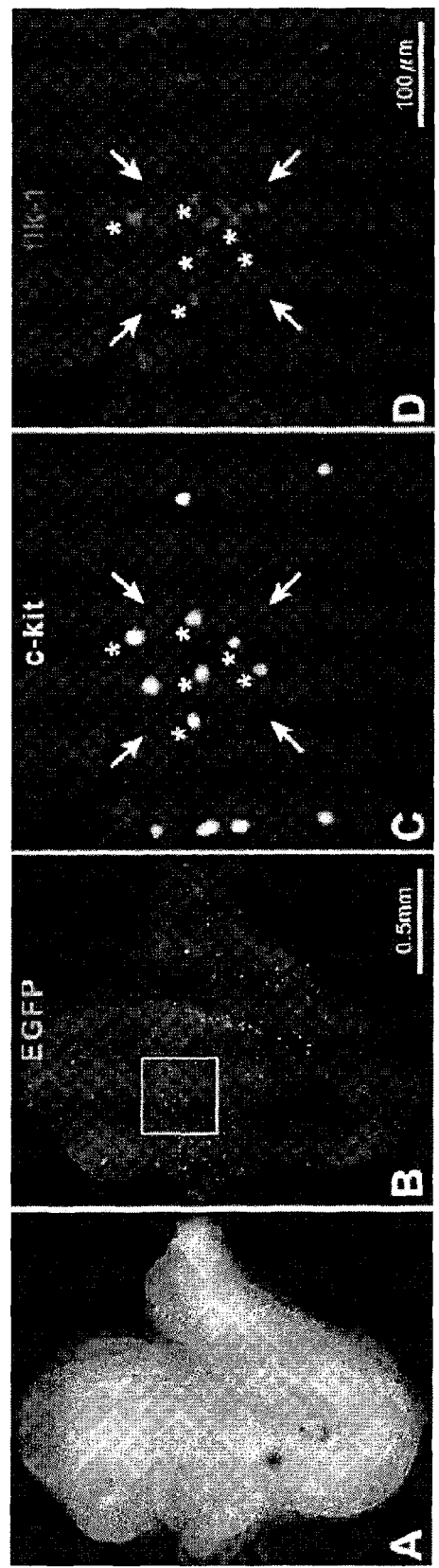
FIG. 1. Pro-epicardium. (A, B) Embryo at E9 showing the localization of c-kit-positive EGFP-positive progenitor cells (PCs) (B: green). Area in the rectangle is shown at higher magnification in C and D. Arrows delimit the pro-epicardium. EGFP-positive PCs express c-kit (C, white) and flk1 (D, magenta). PCs positive for c-kit and flk1 are indicated by asterisks.

As used herein, "autologous" refers to something that is derived or transferred from the same individual's body (i.e., autologous blood donation; an autologous bone marrow transplant).

As used herein, "allogeneic" refers to something that is genetically different although belonging to or obtained from the same species (e.g., allogeneic tissue grafts or organ transplants).

As used herein, "stem cells" are used interchangeably with "progenitor cells" and refer to cells that have the ability to renew themselves through mitosis as well as differentiate into various specialized cell types. The stem cells used in the invention are somatic stem cells, such as bone marrow or cardiac stein cells or progenitor cells. "Vascular progenitor cells" or VPCs are a subset of adult cardiac stem cells that are c-kit positive and flk1 (e.g. VEGFR-2) positive, which generate predominantly endothelial cells and smooth muscle cells. "Myocyte progenitor cells" or MPCs are a subset of adult cardiac stem cells that are c-kit positive and flk1 negative, which generate cardiomyocytes predominantly.

As used herein, "adult" stem cells refers to stem cells that are not embryonic in origin nor derived from embryos or fetal tissue.

Stem cells employed in the invention are advantageously selected to be lineage negative. The term "lineage negative" is known to one skilled in the art as meaning the cell does not express antigens characteristic of specific cell lineages. And, it is advantageous that the lineage negative stem cells are selected to be c-kit positive. The term "c-kit" is known to one skilled in the art as being a receptor which is known to be present on the surface of stem cells, and which is routinely utilized in the process of identifying and separating stem cells from other surrounding cells.

As used herein, the term "cytokine" is used interchangeably with "growth factor" and refers to peptides or proteins that bind receptors on cell surfaces and initiate signaling cascades thus influencing cellular processes. The terms "cytokine" and "growth factor" encompass functional variants of the native cytokine or growth factor. A functional variant of the cytokine or growth factor would retain the ability to activate its corresponding receptor. Variants can include amino acid substitutions, insertions, deletions, alternative splice variants, or fragments of the native protein. The term "variant" with respect to a polypeptide refers to an amino acid sequence that is altered by one or more amino acids with respect to a reference sequence. The variant can have "conservative" changes, wherein a substituted amino acid has similar structural or chemical properties, e.g., replacement of leucine with isoleucine. Alternatively, a variant can have "nonconservative" changes, e.g., replacement of a glycine with a tryptophan. Analogous minor variations can also include amino acid deletion or insertion, or both. Guidance in determining which amino acid residues can be substituted, inserted, or deleted without eliminating biological activity can be found using computer programs well known in the art, for example, DNASTAR software.

As used herein "damaged myocardium" refers to myocardial cells which have been exposed to ischemic conditions. These ischemic conditions may be caused by a myocardial infarction, or other cardiovascular disease or related complaint. The lack of oxygen causes the death of the cells in the surrounding area, leaving an infarct, which will eventually scar.

As used herein, "patient" or "subject" may encompass any vertebrate including but not limited to humans, mammals, reptiles, amphibians and fish. However, advantageously, the patient or subject is a mammal such as a human, or a mammal such as a domesticated mammal, e.g., dog, cat, horse, and the like, or production mammal, e.g., cow, sheep, pig, and the like.

The pharmaceutical compositions of the present invention may be used as therapeutic agents—i.e. in therapy applications. As herein, the terms "treatment" and "therapy" include curative effects, alleviation effects, and prophylactic effects. In certain embodiments, a therapeutically effective dose of progenitor cells is applied, delivered, or administered to the heart or implanted into the heart. An effective dose or amount is an amount sufficient to effect a beneficial or desired clinical result. Said dose could be administered in one or more administrations.

Mention is made of the following related pending patent applications:

U.S. Application Publication No. 2003/0054973, filed Jun. 5, 2002, which is herein incorporated by reference in its entirety, discloses methods, compositions, and kits for repairing damaged myocardium and/or myocardial cells including the administration cytokines.

U.S. Application Publication No. 2006/0239983, filed Feb. 16, 2006, which is herein incorporated by reference in its entirety, discloses methods, compositions, and kits for repairing damaged myocardium and/or myocardial cells including the administration of cytokines and/or adult stem cells as well as methods and compositions for the development of large arteries and vessels. The application also discloses methods and media for the growth, expansion, and activation of human cardiac stem cells.

Figure 2:
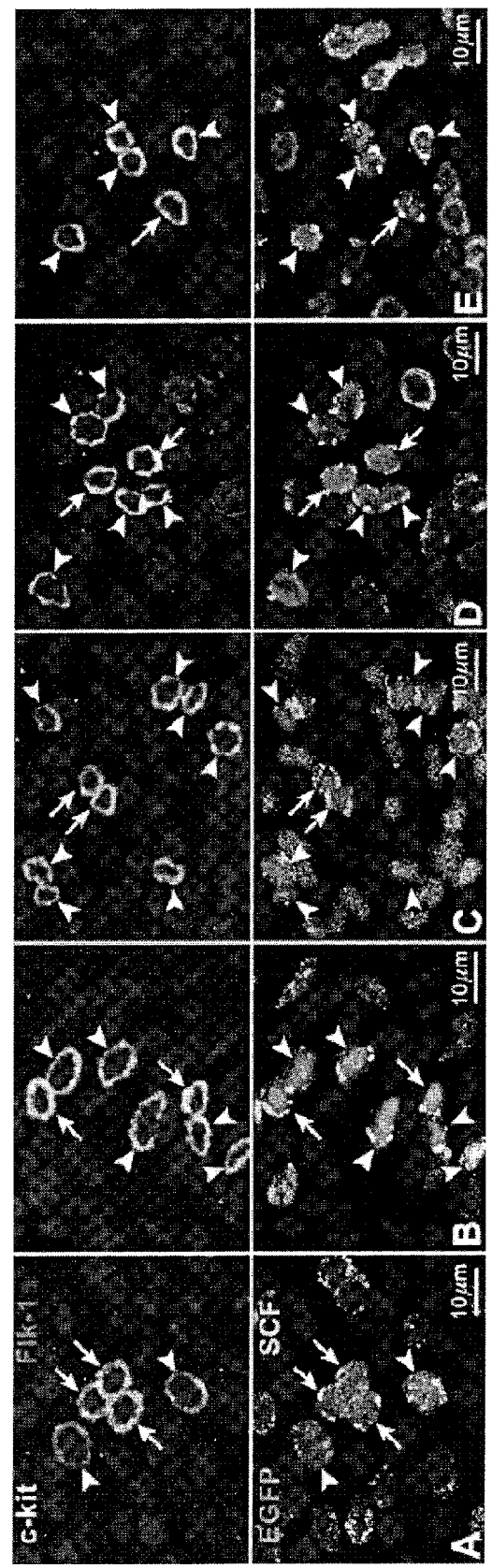
FIG. 2. Progenitor Cells in c-kit-EGFP mice. Expression of flk1 (upper panels, magenta), c-kit (upper panels, white) and SCF (lower panels, yellow) in EGFP-positive PCs (lower panels, green) in the primitive streak (A), cardiac crescent (B), heart tube (C), looping heart (D) and four-chambered heart (E). Arrows: c-kit-positive flk1-positive PCs. Arrowheads: c-kit-positive flk1-negative PCs.

In development, the cardiogenic mesoderm contains two populations of progenitor cells (PCs), which are destined to generate pre-cardiomyocytes and pre-endocardial cells while coronary vessels are formed independently (1-5). Endothelial and smooth muscle precursors migrate from the pro-epicardium and differentiate into sinusoidal vesicles that create capillary channels (6-8). When the closed vessel network is established and connections with the aorta are made, smooth muscle precursors migrate to segments of the endothelial channels and coronary arteries are formed (8-11). Five classes of PCs have been implicated in cardiac development: endocardial, myocardial, endothelial, smooth muscle and peri-vascular connective tissue cell progenitors-precursors. The contracting heart is avascular for several days (2, 7), strengthening the notion that the origin of the coronary vasculature is distinct from the muscle mass. The inventors have identified in the developing mouse heart that c-kit-positive-flk1-positive PCs together with c-kit-positive flk1-negative PCs are present in the pro-epicardium from which the coronary circulation is formed and in the primitive myocardium from which cardiomyocytes originate (FIGS. 1 and 2). Thus, c-kit is present in two PC classes differentiating into vascular cells and cardiomyocytes. To provide evidence in favor of the interaction of c-kit, flk1 and the c-kit ligand, stem cell factor (SCF), in cardiac development their colocalization was established in embryos from c-kit-EGFP mice; flk1, c-kit and SCF were concurrently expressed in the primitive streak, cardiac crescent, primitive heart tube, looping heart and four-chambered heart (FIG. 2). A second subset of c-kit-positive flk1-negative cells was also found.

The identification that several PCs regulate cardiac development together with observations of myocyte and vessel formation in the adult (12-17), has led to the recognition that the heart is a dynamic organ regulated by a stem cell compartment (18-20). Moreover, this intrinsic cellular system promotes partial cardiac repair following injury (21-23). Although several cardiac PC classes have been described (21, 22, 24-32), the inventors have discovered c-kit-positive flk1-negative myocyte progenitor cells (MPCs) appear to represent the most potent cell for myocardial regeneration (18-22). The inventors have focused on the functional characterization of MPCs and their ability to form a myocyte progeny that reaches the adult phenotype in rodent, dogs and humans (16, 21-23, 33). These cells acquire the electrical, mechanical and calcium transient properties of mature myocytes (21, 23, 33). Also, MPCs give rise to coronary arterioles and capillary structures. Myocyte regeneration is impressive but vessel growth is not as striking as myocyte growth (21-23, 33). This differential response is consistent with in vitro results in which MPCs differentiate predominantly into myocytes and to a lesser extent into endothelial cells (ECs) and smooth muscle cells (SMCs) (21, 33). Thus, MPCs acquire predominantly a cardiomyogenic fate but possess also a restricted ability to form ECs and SMCs. Accordingly, the present invention provides isolated myocyte progenitor cells, wherein the myocyte progenitor cells are c-kit positive and flk1 negative. In one embodiment, the myocyte progenitor cells differentiate predominantly into cardiomyocytes, that is at least 80%, at least 85%, at least 90%, or at least 95% of the cells generated from myocyte progenitor cells are cardiomyocytes.

The notion that PCs in the adult heart generate de novo coronary vessels is at variance with the traditional view of coronary vessel biology. It is generally believed that, in contrast to active vessel growth in the embryonic and neonatal heart, the adult coronary vasculature is quiescent (34). A certain degree of expansion of the vascular bed is considered possible only after tissue injury (35, 36). This process can be mediated by three mechanisms (FIG. 3A): (a) angiogenesis that corresponds to the sprouting of mature ECs from pre-existing vessels in response to angiogenic growth factors (36); (b) vasculogenesis that corresponds to sites of active neovascularization mediated by recruitment of circulating endothelial progenitor cells (EPCs) from the bone marrow (37-40); and (c) adaptive arteriogenesis or collateral vessel formation that corresponds to the development of large vessels from pre-existing arteriolar anastomosis (41). This process is mediated by shear-stress which upregulates angiogenic and inflammatory factors (34, 35). Thus, at the site of vascularization, ECs are assumed to originate from adjacent pre-existing blood vessels or from recruited EPCs. SMCs are derived from a pool of circulating progenitors or, in analogy to atherogenesis, from mature cells in the media (41-43).

The contribution of resident vascular PCs to vasculogenesis is a relatively new concept in vascular biology. Among the most likely candidates, a population of Sca-1 positive PCs located in the adventitia of the mouse aorta may represent a novel vascular primitive cell (44-47). Multipotent, self-renewing cells with characteristics similar to embryonic mesangioblasts have been isolated from the embryonic aorta (48-50) and PCs with vasculogenic potential have been identified in the human thoracic aorta (51). Importantly, in the presence of tissue ischemia, various organs contribute to the release of a pool of circulating PCs distinct from the bone marrow which have powerful vasculogenic properties (52). Collectively, this novel information suggests that undifferentiated cells may reside in the vessel wall and play a relevant role in vessel homeostasis and regeneration.

Figure 6:
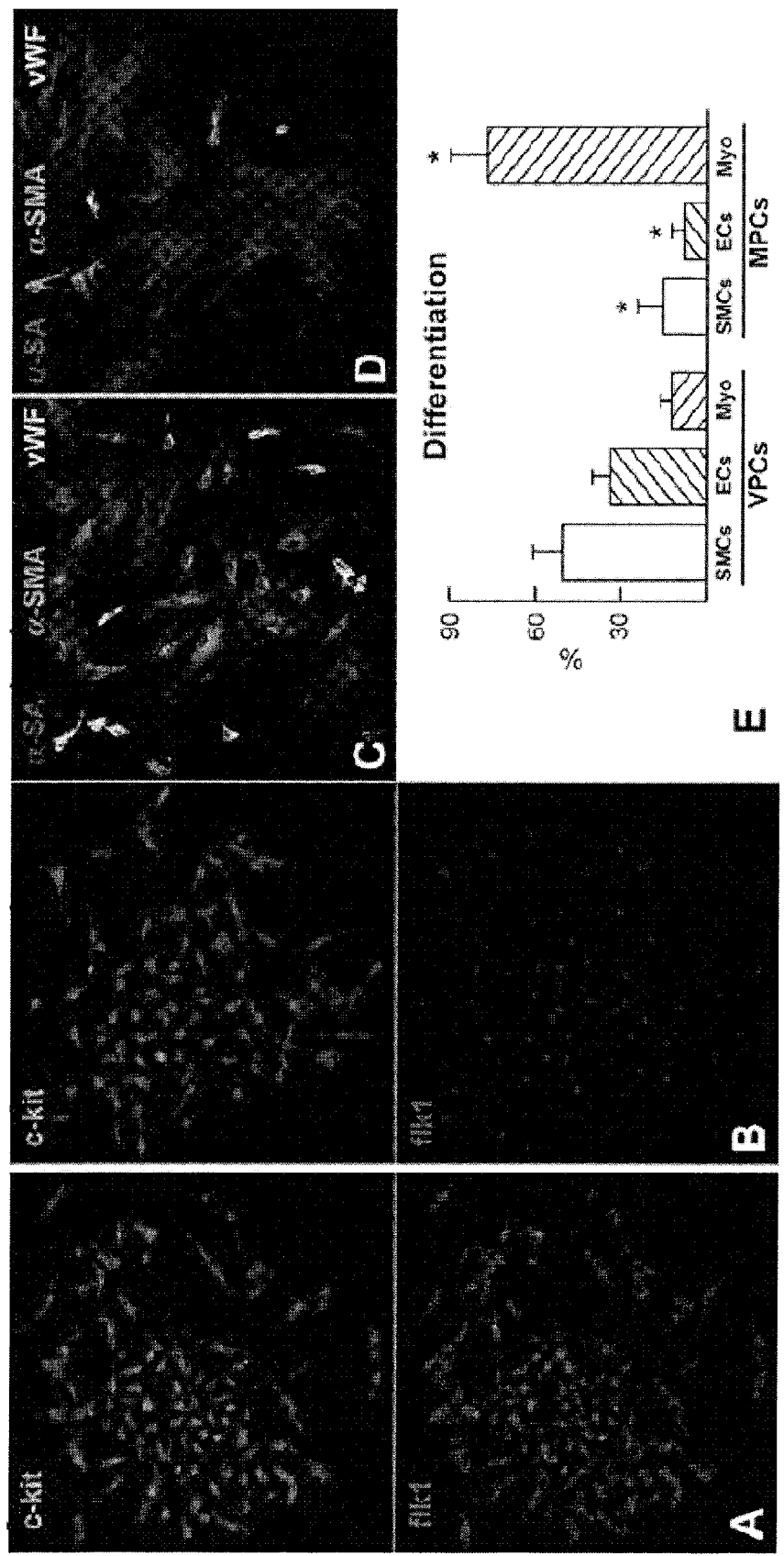
FIG. 6. Clonogenic VPCs and MPCs. Clones generated by deposition of single VPCs and MPCs. VPCs express c-kit and flk1 (A), and MPCs c-kit only (B). Clonogenic VPCs (C) differentiate mostly into ECs (vWF: yellow) and SMCs (α-SMA: green) and MPCs (D) mostly into myocytes (α-SA: red). E: Differentiation pattern of VPCs and MPCs. Results are mean±SD. *Difference between VPCs and MPCs.
Figure 7:
FIG. 7. EPCs and myocardial regeneration. Human EPCs injected in the infarcted immunodeficient mouse heart formed human (Alu sequences, green dots in nuclei) coronary vessels (left panel: α-SM-actin, yellow; middle panel: vWF, white) and new myocytes (right panel: α-SA, red; arrows). *Spared myocytes FIG. 8. Mechanisms of asymmetric division of stem cells. (A) Cell polarization involves the establishment of distinct membrane domains, apical and basolateral, through the formation of adherens junctions. (B) The orientation of the mitotic spindle depends on polarity proteins which determine the localization of the cell fate determinants. (C) The distribution of the cell fate determinants Numb and α-adaptin conditions the pattern of stem cell division. The uniform localization of these endocytic proteins at the two poles of the dividing stem cell results in the generation of two daughter cells with identical fate. But the non-uniform localization of these endocytic proteins at one pole only of the dividing stem cell results in the generation of two daughter cells with different fate.

Therefore, in analogy to cardiomyogenesis that is promoted by activation, proliferation and differentiation of resident MPCs, the inventors suggested that the physiological turnover of vascular ECs and SMCs and vasculogenesis following injury are regulated by the commitment of resident c-kit-positive flk1-positive vascular progenitor cells (VPCs). The inventors have found that c-kit-flk1-positive PCs from the adult mouse heart generate single cell clones and these clonogenic cells differentiate predominantly into ECs and SMCs and to a much smaller extent into myocytes (FIG. 6).

Thus, c-kit-flk1-positive PCs are nested in vascular niches and possess the fundamental properties of stem cells: they are self-renewing, clonogenic and multipotent. They appear to constitute a novel class of adult VPC distinct from MPCs. MPCs are located in myocardial niches, do not express flk1 and differentiate predominantly into cardiomyocytes. Thus, the present invention also provides isolated vascular progenitor cells, wherein the vascular progenitor cells are c-kit positive and flk1 (e.g. VEGFR-2) positive. In one embodiment, the vascular progenitor cells differentiate predominantly into ECs and SMCs, that is at least 80%, at least 85%, at least 90%, or at least 95% of the cells generated from vascular progenitor cells are ECs and SMCs.

Given the regenerative capacity of these new classes of cardiac PCs and their propensity for generating particular cardiac lineages, MPCs and VPCs are particularly useful in generating new myocardial tissue and vessels, respectively. Accordingly, the present invention provides a method for restoring structural and functional integrity to damaged myocardium in a subject in need thereof. Restoration of structural and functional integrity preferably requires the generation of new functional myocardium comprised of new cardiomyocytes as well as new myocardial vessels comprised of new endothelial and smooth muscle cells. In one embodiment, the method comprises obtaining myocardial tissue from the subject; extracting vascular progenitor cells from said myocardial tissue; expanding said vascular progenitor cells in culture; and administering said vascular progenitor cells to the damaged myocardium, wherein the vascular progenitor cells differentiate into endothelial cells and smooth muscles cells forming functional coronary vessels, thereby increasing blood flow to the damaged myocardium. Preferably, the vascular progenitor cells are c-kit positive and flk1 positive.

In another embodiment, the method further comprising extracting myocyte progenitor cells from said myocardial tissue, expanding said myocyte progenitor cells in culture; and administering said myocyte progenitor cells to the damaged myocardium, wherein the myocyte progenitor cells differentiate into cardiomyocytes forming functional myocardium, thereby increasing contractile function. Preferably, the myocyte progenitor cells are c-kit positive and flk1 negative.

Administration of VPCs and/or MPCs are used to restore structural and functional integrity to damaged myocardium and or damaged myocardial vessels resulting from cardiovascular diseases, including, but not limited to, atherosclerosis, ischemia, hypertension, restenosis, angina pectoris, rheumatic heart disease, congenital cardiovascular defects and arterial inflammation and other diseases of the arteries, arterioles and capillaries or related complaint. In some embodiments, the subject is suffering from a myocardial infarction and the damaged myocardium is an infarct. The vascular progenitor cells and myocyte progenitor cells may be administered to a border zone of the damaged myocardium (e.g. infarct) and/or they may be administered to the middle of the infarct.

The present invention also provides a method of generating a biological bypass in a subject in need thereof. This method can be used in conjunction with surgical procedures, such as stenting and angioplasty, or is preferably used in place of such surgical procedures. In one embodiment, the method comprises obtaining myocardial tissue from the subject; extracting vascular progenitor cells from said myocardial tissue; expanding said vascular progenitor cells in culture; and administering said vascular progenitor cells to a stenotic or occluded artery in the subject's heart, wherein the vascular progenitor cells differentiate into endothelial cells and/or smooth muscle cells, thereby forming coronary vessels that reestablish blood flow to the myocardium.

The coronary vessels that may be formed include coronary arteries, arterioles, and capillaries. The formed coronary vessels may have diameters ranging from about 6 µm to about 2 mm. In one embodiment, the coronary vessel has a diameter of over 100 µm. In a further embodiment, the formed coronary vessel has a diameter of at least 125, at least 150, at least 175, at least 200, at least 225, at least 250, at least 275, at least 300, at least 325, at least 350, at least 375, at least 400, at least 425, at least 450, or at least 475 µm. In a preferred embodiment, formed coronary arteries have a diameter of at least 500 µm. In yet another embodiment of the present invention, the formed coronary vessel provides a biological bypass around an area in need of therapy or repair, including around an occlusion or blockage, such that blood flow, blood pressure, and circulation are restored or improved. Improvements or enhancements in blood flow and cardiac function or contractility can be assessed using standard techniques known to those skilled in the art of cardiology, including, but not limited to, hemodynamic analysis and echocardiography.

The present invention also encompasses methods of treating or preventing hypertensive cardiomyopathy. Hypertensive cardiomyopathy is a weakening of the heart muscle or a change in heart muscle structure caused by prolonged high blood pressure, which can lead to heart failure.

The evolution of hypertensive cardiomyopathy may be conditioned by the formation of dysfunctional vascular and myocardial niches and loss of functionally-competent VPCs and MPCs. Thus, it may be possible to interfere with the etiology of hypertensive cardiomyopathy by repopulating dysfunctional niches and the PC pool with functionally-competent VPCs and MPCs or by creating new vascular and myocardial niches. The newly repopulated niches can provide a sufficient number of VPCs and MPCs to regenerate an unlimited number of coronary vessels and myocytes so that the heart can have the capacity to correct anatomical changes produced by pathologic loads and sustain pump function indefinitely.

Figure 3:
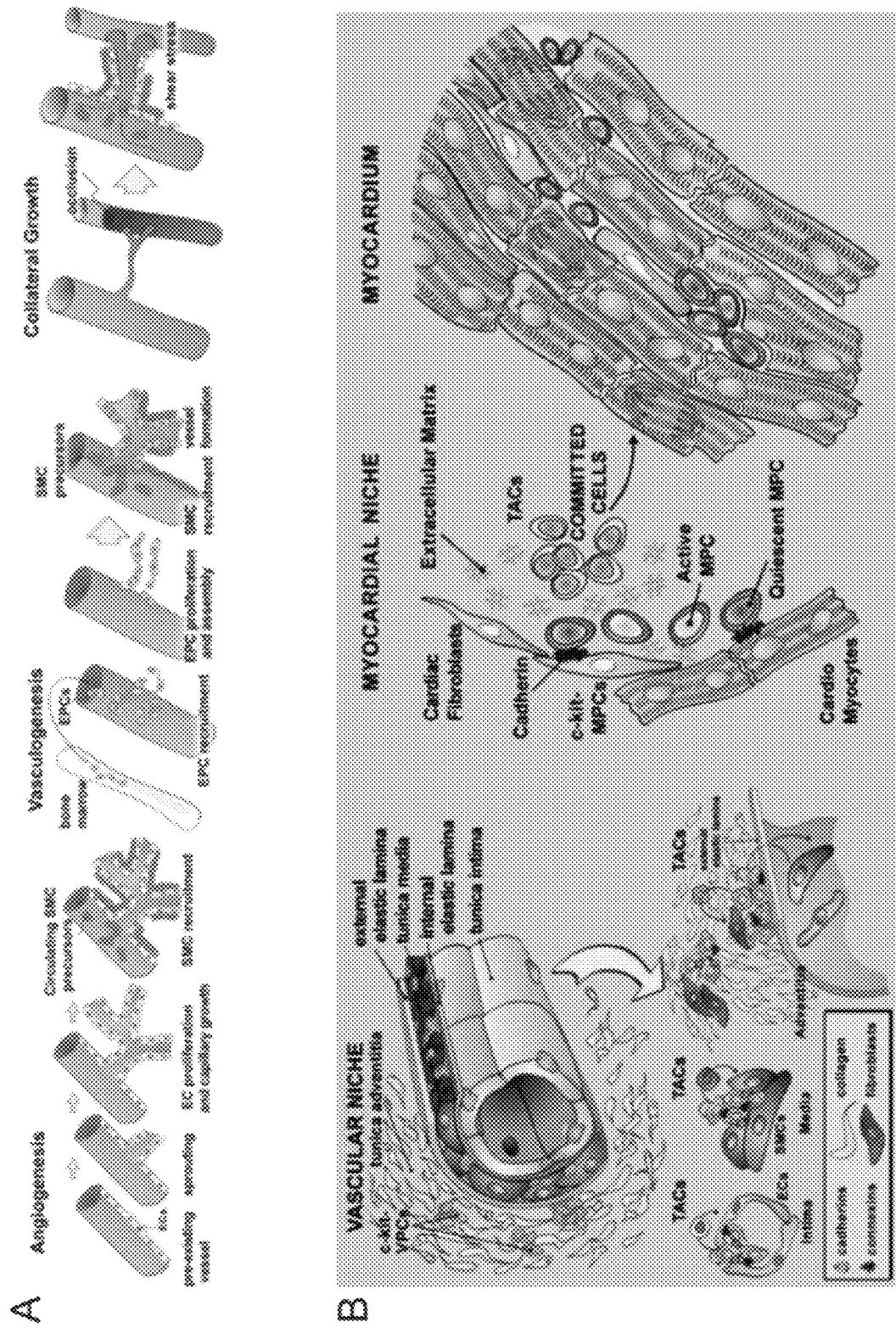
FIG. 3. A. Formation of vessels. Regeneration of vessels by proliferation of resident differentiated cells or recruitment of circulating progenitors. B. Cardiac niches. Vascular niches contain quiescent VPCs that following activation leave the niche area and give rise to transient amplifying cells (TACs) differentiating into SMCs, ECs and adventitial cells. Similarly, myocardial niches contain quiescent MPCs that following activation leave the niche area and give rise to TACs differentiating into myocytes.
Figure 4:
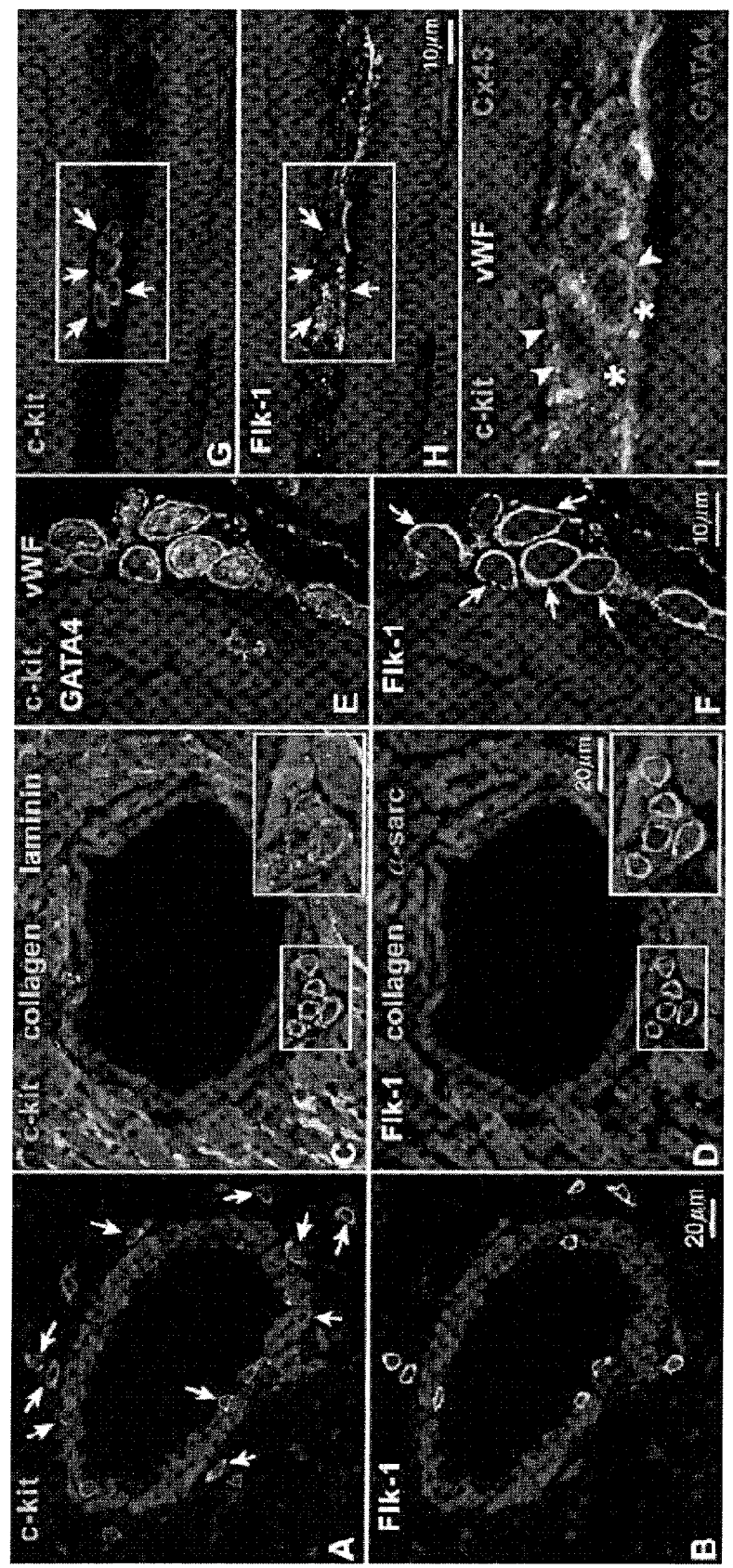
FIG. 4. Vascular niches. C-kit-positive (A, C, E, G: green, arrows) flk1-positive (B, D, F, H: white, arrows) VPCs in the endothelium (A, B: not stained; E, F, I: vWF, yellow), SMC layer (A, B: α-SM-actin, red) and adventitia (A, B: not stained; C, D: collagen, blue) of coronary arterioles and tangentially sectioned capillaries (E-I) in the mouse (A, C, E) and rat (G) heart. Connexin 43 (magenta, arrowheads) is present between c-kit-flk1-positive cells and ECs (G-I). GATA4 positive cells (E: white; I: red). *VPCs positive for c-kit and flk1 only (I). A continuous basal lamina (yellow) that defines the vascular niche is not present (C; inset). Some of the cells adjacent to vessel (A, B) are c-kit-positive flk1-negative. The functional role of these cells is identified only by their differentiation potential in vitro, as discussed in the detailed description.

VPC and MPC niches possess distinct structural and functional properties (FIG. 3B). The inventors have shown that VPCs are nested within the endothelium, the media and the adventitia of different classes of coronary vessels of the mouse and rat heart (FIG. 4). Gap and adherens junctions made by connexins and cadherins are present between VPCs, and between VPCs and ECs, SMCs and fibroblasts. VPCs in the intima and media appear as single cells or in groups of 2-4 cells. Larger pockets of VPCs are found predominantly in close proximity to large-intermediate arteries and resistance arterioles. Cell clusters consist of undifferentiated VPCs and lineage committed cells (LCC), i.e., ECs and SMCs. Larger clusters in the adventitia are similar but occasionally show one or two cells committed to the myocyte fate. Collectively, these structural properties are consistent with vascular niches.

Figure 5:
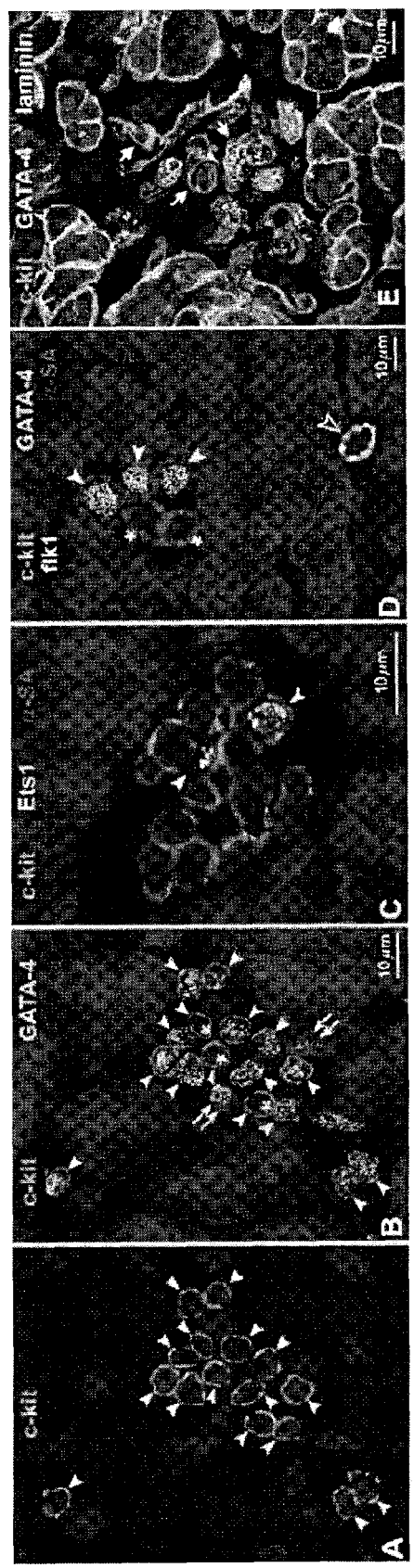
FIG. 5. Myocardial niches. Some MPCs (A-D: c-kit, green) express GATA4 (B, D: yellow, arrowheads) or Ets1 (C: white, arrowheads). *MPCs positive for c-kit and negative for GATA4. Small developing myocytes are also apparent (B, double arrows). (B: α-sarcomeric actin, α-SA, red; double arrows). (E) A continuous basal lamina (white) that defines the myocardial niche is not present. A single PC that expresses c-kit and flk1 is also present (D: VPC, open arrow).

Vascular niches are distinct from myocardial niches for their localization along the territory of the coronary vessels and cellular composition. In myocardial niches, MPCs are intimately associated with cells predominantly committed to the myocyte lineage although EC and SMC progenitor-precursors may be found (FIG. 5). In myocardial niches, myocytes and fibroblasts but not ECs operate as supporting cells (53). Thus, vascular and myocardial niches function in tandem to sustain heart homeostasis.

In one embodiment of the invention, the method for treating or preventing hypertensive cardiomyopathy in a subject in need thereof comprises administering vascular progenitor cells and myocyte progenitor cells to the subject's heart, wherein the vascular progenitor cells and myocyte progenitor cells engraft in said subject's heart, thereby repopulating diminished progenitor cell niches or forming new progenitor cell niches. In preferred embodiments, the vascular progenitor cells and myocyte progenitor cells are autologous.

Following administration of the progenitor cells to the subject's heart, the vascular progenitor cells engraft within established vascular niches or form new vascular niches within the walls or coronary vessels. Similarly, following their administration, myocyte progenitor cells engraft within established myocyte niches or form new myocyte niches within the myocardium, particularly in the subject's atria or myocardial apex. Repopulation of the progenitor cell niches within a subject's heart restores the regenerative capacity of the subject's heart and can reduce the symptoms or occurrence of cardiovascular disease or heart failure. Thus, the present invention also provides a method for restoring regenerative capacity to a subject's heart by administering VPCs and/or MPCs to the subject's heart. In one embodiment, the probability of the subject having heart failure is reduced following administration of the progenitor cells.

The present invention also includes a method for treating or preventing heart failure in a subject in need thereof. Heart failure may be the result of diminished functional capacity of resident VPCs and MPCs or a depletion of functional VPCs and MPCs within their respective niches in the heart. In one embodiment of the invention, the method comprises obtaining myocardial tissue from the subject; extracting vascular progenitor cells from said myocardial tissue; expanding said vascular progenitor cells in culture; and administering said vascular progenitor cells to the subject's heart, wherein the vascular progenitor cells differentiate into endothelial cells and smooth muscles cells forming functional coronary vessels, thereby increasing cardiac function.

In another embodiment, the method further comprises extracting myocyte progenitor cells from said myocardial tissue, expanding said myocyte progenitor cells in culture; and administering said myocyte progenitor cells to the damaged myocardium, wherein the myocyte progenitor cells differentiate into cardiomyocytes forming functional myocardium, thereby increasing cardiac function. Increased cardiac function may be reflected as increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased left and right ventricular wall stress, and decreased wall tension. In some embodiments, multiple administrations of VPCs and/or MPCs may be made to the subject's heart. For example, VPCs and/or MPCs may be administered in two or more, three or more, four or more, five or more, or six or more injections. Injections may be made at the base of the heart, the apex, or the mid-region. In one embodiment, two injections of VPCs and/or MPCs are made at each of the apex, mid-region, and base.

Preferably, one or more symptoms of heart failure are reduced or alleviated following administration of VPCs and/or MPCs. Symptoms of heart failure include, but are not limited to, fatigue, weakness, rapid or irregular heartbeat, dyspnea, persistent cough or wheezing, edema in the legs and feet, and swelling of the abdomen.

Progenitor cells may be isolated from tissue specimens (e.g. myocardium or myocardial vessels) obtained from a subject or patient. By way of example, myocardial tissue specimens may be minced and placed in appropriate culture medium. Cardiac progenitor cells growing out from the tissue specimens can be observed in approximately 1-2 weeks after initial culture. At approximately 4 weeks after the initial culture, the expanded progenitor cells may be collected by centrifugation. Other methods of isolating adult cardiac progenitor cells from a subject are known in the art and can be employed to obtain suitable progenitor cells for use in the methods of the invention. U.S. Patent Application Publication No. 2006/0239983, filed Feb. 16, 2006, which is herein incorporated by reference in its entirety, describes media appropriate for culturing and expanding adult progenitor cells, particularly human cardiac progenitor cells. However, one of ordinary skill in the art would be able to determine the necessary components and modify commonly used cell culture media to be employed in culturing the isolated cardiac progenitor cells of the invention.

It is preferable that the cardiac progenitor cells of the invention are lineage negative. Lineage negative progenitor cells can be isolated by various means, including but not limited to, removing lineage positive cells by contacting the progenitor cell population with antibodies against lineage markers and subsequently isolating the antibody-bound cells by using an anti-immunoglobulin antibody conjugated to magnetic beads and a biomagnet. Alternatively, the antibody-bound lineage positive stem cells may be retained on a column containing beads conjugated to anti-immunoglobulin antibodies. The cells not bound to the immunomagnetic beads represent the lineage negative progenitor cell fraction and may be isolated. For instance, cells expressing markers of the cardiac lineage (e.g. markers of vascular cell or cardiomyocyte commitment) may be removed from cardiac progenitor cell populations to isolate lineage negative cardiac progenitor cells. Markers of the vascular lineage include, but are not limited to, GATA6 (SMC transcription factor), Ets1 (EC transcription factor), Tie-2 (angiopoietin receptors). VE-cadherin (cell adhesion molecule), CD62E/E-selectin (cell adhesion molecule), alpha-SM-actin (α-SMA, contractile protein), CD31 (PECAM-1), vWF (carrier of factor VIII), Bandeiraera simplicifolia and Ulex europaeus lectins (EC surface glycoprotein-binding molecules). Markers of the myocyte lineage include, but are not limited to, GATA4 (cardiac transcription factor), Nkx2.5 and MEF2C (myocyte transcription factors), and alpha-sarcomeric actin (α-SA, contractile protein).

In a preferred embodiment of the invention, the lineage negative progenitor cells express the stem cell surface marker, c-kit, which is the receptor for stem cell factor. Positive selection methods for isolating a population of lineage negative progenitor cells expressing c-kit are well known to the skilled artisan. Examples of possible methods include, but are not limited to, various types of cell sorting, such as fluorescence activated cell sorting (FACS) and magnetic cell sorting as well as modified forms of affinity chromatography. In a preferred embodiment, the lineage negative progenitor cells are c-kit positive.

Vascular progenitor cells are isolated by selecting cells expressing the VEGFR2 receptor, Oki, from the c-kit positive progenitor cell population, isolated as described above. Thus, vascular progenitor cells are lineage negative, c-kit positive, and flk1 positive. Similarly, myocyte progenitor cells are isolated from the c-kit progenitor cell population by selecting cells that do no express flk1. Therefore, myocyte progenitor cells are lineage negative, c-kit positive, and flk1 negative. Similar methods for isolating c-kit positive progenitor cells may be employed to select cells that express or do not express the flk1 receptor (e.g. immunobeads, cell sorting, affinity chromatography, etc.).

Isolated lineage negative, c-kit positive progenitor cells (e.g. VPCs and MPCs) may be plated individually, for instance in single wells of a cell culture plate, and expanded to obtain clones from individual progenitor cells. In some embodiments, cardiac progenitor cells that are c-kit positive and flk1 positive are plated individually to obtain pure cultures of vascular progenitor cells. In other embodiments, cardiac progenitor cells that are c-kit positive and flk1 negative are plated individually to obtain pure cultures of myocyte progenitor cells.

In certain embodiments of the invention, the vascular progenitor cells or myocyte progenitor cells are activated prior to administration to a subject. Activation of the progenitor cells may be accomplished by exposing the progenitor cells to one or more cytokines. Suitable concentrations of the one or more cytokines for activating the progenitor cells include a concentration of about 0.1 to about 500 ng/ml, about 10 to about 500 ng/ml, about 20 to about 400 ng/ml, about 30 to about 300 ng/ml, about 50 to about 200 ng/ml, or about 80 to about 150 ng/ml. In one embodiment, the concentration of one or more cytokines is about 25, about 50, about 75, about 100, about 125, about 150, about 175, about 200, about 225, about 250, about 275, about 300, about 325, about 350, about 375, about 400, about 425, about 450, about 475, or about 500 ng/ml. In some embodiments, the vascular progenitor cells or myocyte progenitor cells are activated by contact with hepatocyte growth factor (HGF), insulin-like growth factor-1 (IGF-1), or a variant thereof.

HGF positively influences stem cell migration and homing through the activation of the c-Met receptor (Kollet et al. (2003) J. Clin. Invest. 112: 160-169; Linke et al. (2005) Proc. Natl. Acad. Sci. USA 102: 8966-8971; Rosu-Myles et al. (2005) J. Cell. Sci. 118: 4343-4352; Urbanek et al. (2005) Circ. Res. 97: 663-673). Similarly, IGF-1 and its corresponding receptor (IGF-1R) induce cardiac stem cell division, upregulate telomerase activity, hinder replicative senescence and preserve the pool of functionally-competent cardiac stem cells in the heart (Kajstura et al. (2001) Diabetes 50: 1414-1424; Torella et al. (2004) Circ. Res. 94: 514-524; Davis et al. (2006) Proc. Natl. Acad. Sci. USA 103: 8155-8160). In some embodiments, the vascular progenitor cells or myocyte progenitor cells are contacted with HGF and IGF-1.

Some other non-limiting examples of cytokines that are suitable for the activation of the vascular progenitor cells or myocyte progenitor cells include Activin A, Bone Morphogenic Protein 2, Bone Morphogenic Protein 4, Bone Morphogenic Protein 6, Cardiotrophin-1, Fibroblast Growth Factor 1, Fibroblast Growth Factor 4, Flt3 Ligand, Glial-Derived Neurotrophic Factor, Heparin, Insulin-like Growth Factor-11, Insulin-Like Growth Factor Binding Protein-3, Insulin-Like Growth Factor Binding Protein-5, Interleukin-3, Interleukin-6, Interleukin-8, Leukemia Inhibitory Factor, Midkine, Platelet-Derived Growth Factor AA, Platelet-Derived Growth Factor BB, Progesterone, Putrescine, Stem Cell Factor, Stromal-Derived Factor-1, Thrombopoietin, Transforming Growth Factor-α, Transforming Growth Factor-β1, Transforming Growth Factor-β2, Transforming Growth Factor-□β3, Vascular Endothelial Growth Factor, Wnt1, Wnt3a, and Wnt5a, as described in Kanemura et al. (2005) Cell Transplant. 14:673-682; Kaplan et al. (2005) Nature 438:750-751; Xu et al. (2005) Methods Mol. Med. 121:189-202; Quinn et al. (2005) Methods Mol. Med. 121:125-148; Almeida et al. (2005) J Biol Chem. 280:41342-41351; Barnabe-Heider et al. (2005) Neuron 48:253-265; Madlambayan et al. (2005) Exp Hematol 33:1229-1239; Kamanga-Sollo et al. (2005) Exp Cell Res 311:167-176; Heese et al. (2005) Neuro-oncol. 7:476-484; He et al. (2005) Am J. Physiol. 289:H968-H972; Beattie et al. (2005) Stem Cells 23:489-495; Sekiya et al. (2005) Cell Tissue Res 320:269-276; Weidt (2004) Stem Cells 22:890-896; Encabo et al (2004) Stem Cells 22:725-740; and Buytaeri-Hoefen et al. (2004) Stem Cells 22:669-674, the entire text of each of which is incorporated herein by reference.

Functional variants of the above-mentioned cytokines can also be employed in the invention. Functional cytokine variants would retain the ability to bind and activate their corresponding receptors. Variants can include amino acid substitutions, insertions, deletions, alternative splice variants, or fragments of the native protein. For example, NK1 and NK2 are natural splice variants of HGF, which are able to bind to the c-MET receptor. These types of naturally occurring splice variants as well as engineered variants of the cytokine proteins that retain function can be employed to activate the progenitor cells of the invention.

The present invention involves administering a therapeutically effective dose or amount of progenitor cells to a subject's heart. An effective dose is an amount sufficient to effect a beneficial or desired clinical result. Said dose could be administered in one or more administrations. In some embodiments, at least three effective doses are administered to the subject's heart. In other embodiments, at least five effective doses are administered to the subject's heart. Each administration of progenitor cells may comprise a single type of progenitor cell (e.g. VPC or MPC) or may contain a mixture of VPCs and MPCs. In one embodiment, VPCs and/or MPCs are administered to a border zone of the damaged myocardium. More than one administration of the progenitor cells may be administered to the border zone, for instance, two or more, three or more, four or more, or five or more administrations may be applied to the border zone of the damaged myocardium.

In some embodiments, it may be beneficial to alter the number of MPCs and VPCs to optimize the ratio that governs flow and function to increase segment function and to fully restore contractile function of the anterior wall of the heart. Thus, in one embodiment, the MPCs are administered simultaneously with VPCs. The ratio of VPCs to MPCs may be adjusted to obtain more endothelial cells, smooth muscle cells, and myocardial vessels or more cardiomyocytes and myocardium. For example, suitable ratios of VPCs to MPCs include, but are not limited to, 1:20; 1:10; 1:5, 1:2; 1:1:2:1, 5:1; 10:1, and 20:1. In a preferred embodiment, the ratio of VPCs to MPCs is 1:1. In other embodiments, MPCs are administered at a particular time interval after VPCs. These embodiments allow for the development of coronary circulation by differentiation of the injected VPCs to support the differentiation, growth and function of later injected MPCs. In one embodiment, MPCs are administered after VPCs have generated functional coronary vessels. Examples of suitable time intervals include, but are not limited to, 1 week, 2 weeks, 3 weeks, 1 month, 2 months, 3 months, 6 months, 9 months, 12 months, 18 months or 24 months.

An effective dose of progenitor cells may be from about $2 \times 10^4$ to about $2 \times 10^7$, more preferably about $1 \times 10^5$ to about $6 \times 10^6$, or most preferably about $2 \times 10^6$. As illustrated in the examples, about $2 \times 10^6$ to about $1 \times 10^7$ progenitor cells are used to effect generation of new myocardium and new myocardial vessels in a canine model. Although there would be a size difference between the heart of a canine and the heart of a human, it is likely that this range of progenitor cells would be sufficient in a human as well. However, the precise determination of what would be considered an effective dose may be based on factors individual to each patient, including their size, age, size of donor heart, type of repopulating progenitor cells (e.g. VPCs, or MPCs), and amount of time after myocardial damage. One skilled in the art, specifically a physician or cardiologist, would be able to determine the number of progenitor cells that would constitute an effective dose without undue experimentation.

The progenitor cells (e.g. stem cells) may be administered to the heart by injection. The injection is preferably intramyocardial. As one skilled in the art would be aware, this is the preferred method of delivery for progenitor cells as the heart is a functioning muscle. Injection by this route ensures that the injected material will not be lost due to the contracting movements of the heart.

In another embodiment, the progenitor cells are administered by injection transendocardially or trans-epicardially. In another embodiment of the invention, the progenitor cells are administered using a catheter-based approach to deliver the trans-endocardial injection. The use of a catheter precludes more invasive methods of delivery wherein the opening of the chest cavity would be necessitated. As one skilled in the art would appreciate, optimum time of recovery would be allowed by the more minimally invasive procedure. A catheter approach involves the use of such techniques as the NOGA catheter or similar systems. The NOGA catheter system facilitates guided administration by providing electromechanic mapping of the area of interest, as well as a retractable needle that can be used to deliver targeted injections or to bathe a targeted area with a therapeutic. Any of the embodiments of the present invention can be administered through the use of such a system to deliver injections or provide a therapeutic. One of skill in the art will recognize alternate systems that also provide the ability to provide targeted treatment through the integration of imaging and a catheter delivery system that can be used with the present invention. Information regarding the use of NOGA and similar systems can be found in, for example, Sherman (2003) Basic Appl. Myol. 13: 11-14; Patel et al. (2005) The Journal of Thoracic and Cardiovascular Surgery 130:1631-38; and Perrin et al. (2003) Circulation 107: 2294-2302; the text of each of which are incorporated herein in their entirety.

In still another embodiment, the progenitor cells may be administered to a subject's heart by an intracoronary route. This route obviates the need to open the chest cavity to deliver the cells directly to the heart. One of skill in the art will recognize other useful methods of delivery or implantation which can be utilized with the present invention, including those described in Dawn et al. (2005) Proc. Natl. Acad. Sci. USA 102, 3766-3771, the contents of which are incorporated herein in their entirety.

The present invention also encompasses a pharmaceutical composition comprising adult vascular progenitor cells and a pharmaceutically acceptable carrier, wherein the vascular progenitor cells are lineage negative, c-kit positive, and flk1 positive. The vascular progenitor cells may be isolated from human myocardium. In one embodiment, the vascular progenitor cells are isolated from the subject to whom they will be administered (i.e. the vascular progenitor cells are autologous). The vascular progenitor cells preferably differentiate predominantly (e.g. greater than 80%) into endothelial cells or smooth muscle cells in vitro.

In another embodiment, the pharmaceutical composition further comprises adult myocyte progenitor cells, wherein the myocyte progenitor cells are lineage negative, c-kit positive, and flk1 negative. The myocyte progenitor cells may be isolated from human myocardium. In one embodiment, the myocyte progenitor cells are isolated from the subject to whom they will be administered (i.e. the myocyte progenitor cells are autologous). The myocyte progenitor cells preferably differentiate predominantly (e.g. greater than 80%) into cardiomyocytes in vitro.

The pharmaceutical composition may comprise a concentration of vascular progenitor cells and/or myocyte progenitor cells from about $2 \times 10^4$ to about $2 \times 10^7$, more preferably about $1 \times 10^5$ to about $6 \times 10^6$, or most preferably about $2 \times 10^6$. In one embodiment, the pharmaceutical composition comprises a concentration of vascular progenitor cells and/or myocyte progenitor cells from about $1 \times 10^5$ cells/ml to about $1 \times 10^7$ cells/ml. In some embodiments, the pharmaceutical composition may comprise vascular progenitor cells and myocyte progenitor cells in a particular ratio. This ratio may be adjusted to generate more vascular tissue (i.e. a higher number of VPCs compared to MPCs) or more myocardium (i.e. a higher number of MPCs compared to VPCs). The ratio of VPCs to MPCs in the pharmaceutical composition may be 1:20; 1:10; 1:5, 1:2; 1:1:2:1, 5:1; 10:1, and 20:1. In a preferred embodiment, the ratio of VPCs to MPCs is 1:1.

The invention also comprehends methods for preparing compositions, such as pharmaceutical compositions, including VPCs and/or MPCs as described herein, for instance, for use in inventive methods for treating or preventing cardiovascular diseases, such as myocardial infarction, hypertensive cardiomyopathy, and heart failure. In one embodiment, the pharmaceutical composition comprises vascular progenitor cells and a pharmaceutically acceptable carrier, wherein said vascular progenitor cells are c-kit positive and flk1 positive. In another embodiment, the pharmaceutical composition comprises myocyte progenitor cells and a pharmaceutically acceptable carrier, wherein said myocyte progenitor cells are c-kit positive and flk1 negative. In still another embodiment, the pharmaceutical composition comprises vascular progenitor cells, myocyte progenitor cells and a pharmaceutically acceptable carrier, wherein said vascular progenitor cells are c-kit positive and flk1 positive and said myocyte progenitor cells are c-kit positive and flk1 negative.

In an additionally preferred aspect, the pharmaceutical compositions of the present invention are delivered via injection. These routes for administration (delivery) include, but are not limited to, subcutaneous or parenteral including intravenous, intraarterial (e.g. intracoronary), intramuscular, intraperitoneal, intramyocardial, transendocardial, trans-epicardial, intranasal administration as well as intrathecal, and infusion techniques. Accordingly, the pharmaceutical composition is preferably in a form that is suitable for injection.

When administering a therapeutic of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion, and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the progenitor cells.

Sterile injectable solutions can be prepared by incorporating the compounds utilized in practicing the present invention in the required amount of the appropriate solvent with various amounts of the other ingredients, as desired.

The pharmaceutical compositions of the present invention, e.g., comprising a therapeutic dose of progenitor cells (e.g. VPC and/or MPCs), can be administered to the patient in an injectable formulation containing any compatible carrier, such as various vehicles, adjuvants, additives, and diluents. Examples of compositions comprising a therapeutic of the invention include liquid preparations for parenteral, subcutaneous, intradermal, intramuscular, intracoronarial, intramyocardial or intravenous administration (e.g., injectable administration), such as sterile suspensions or emulsions. Such compositions may be in admixture with a suitable carrier, diluent, or excipient such as sterile water, physiological saline, glucose or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation.

The compositions can be isotonic, i.e., they can have the same osmotic pressure as blood and lacrimal fluid. The desired isotonicity of the compositions of this invention may be accomplished using sodium chloride, or other pharmaceutically acceptable agents such as dextrose, boric acid, sodium tartrate, propylene glycol or other inorganic or organic solutes. Sodium chloride is preferred particularly for buffers containing sodium ions.

Viscosity of the compositions may be maintained at the selected level using a pharmaceutically acceptable thickening agent. Methylcellulose is preferred because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

A pharmaceutically acceptable preservative can be employed to increase the shelf-life of the compositions. Benzyl alcohol may be suitable, although a variety of preservatives including, for example, parabens, thimerosal, chlorobutanol, or benzalkonium chloride may also be employed. A suitable concentration of the preservative will be from 0.02% to 2% based on the total weight although there may be appreciable variation depending upon the agent selected.

Those skilled in the art will recognize that the components of the compositions should be selected to be chemically inert with respect to the active compound. This will present no problem to those skilled in chemical and pharmaceutical principles, or problems can be readily avoided by reference to standard texts or by simple experiments (not involving undue experimentation), from this disclosure and the documents cited herein.

The inventive compositions of this invention are prepared by mixing the ingredients following generally accepted procedures. For example, isolated progenitor cells can be resuspended in an appropriate pharmaceutically acceptable carrier and the mixture adjusted to the final concentration and viscosity by the addition of water or thickening agent and possibly a buffer to control pH or an additional solute to control tonicity. Generally the pH may be from about 3 to 7.5. Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable, may include an initial administration followed by subsequent administrations; but nonetheless, may be ascertained by the skilled artisan, from this disclosure, the documents cited herein, and the knowledge in the art.

The present invention also includes kits for restoring structural and functional integrity to damaged myocardium or generating a biological bypass. In one embodiment, the kit comprises a pharmaceutical composition, instructions for administering the pharmaceutical composition, and optionally an administration device, wherein the pharmaceutical composition comprises vascular progenitor cells. In another embodiment, the kit comprises a pharmaceutical composition, instructions for administering the pharmaceutical composition, and optionally an administration device, wherein the pharmaceutical composition comprises myocyte progenitor cells. In still another embodiment, the kit comprises a pharmaceutical composition, instructions for administering the pharmaceutical composition, and optionally an administration device, wherein the pharmaceutical composition comprises vascular progenitor cells and myocyte progenitor cells. The vascular progenitor cells and myocyte progenitor cells may be in the same pharmaceutical composition or they may be in separate pharmaceutical compositions packaged in different containers within the kit. Administration devices that may optionally be included in the kit include a catheter, syringe, or any other appropriate administration device.

This invention is further illustrated by the following additional examples that should not be construed as limiting. The contents of all references, patents and published patent applications cited throughout this application, as well as the Figures, are incorporated herein by reference in their entirety.

EXAMPLES

Example 1

Identification of VPCs and Vascular Niches in the Mouse Heart

The objective of the experiments outlined in this example is to identify and characterize vascular niches containing vascular progenitor cells within the vasculature of murine hearts. Homozygous c-kit-EGFP mice at 4 months of age are used for this study (182). They were generated through microinjection of FVB/NJ 0.5 dpc zygotes with clone 2 of the c-kit-EGFP construct. Founder animals were genotyped by PCR and backcrossed to stabilize the transgene. High expressing lines were characterized by PCR and immunohistochemistry for colocalization of endogenous c-kit and EGFP; testes, heart and bone marrow were examined. Although EGFP is under the control of the c-kit promoter, mice do not develop a dilated myopathy. Cardiac function and anatomy were measured in a group of 28 male homozygous mice at 6-11 months of age. No significant differences between wild-type and c-kit-EGFP mice were observed in left ventricular (LV) anatomy or LV hemodynamics A. In Vivo Studies Vascular niches. The heart is arrested in diastole and fixed by perfusion of the coronary vasculature with 10% buffered formalin (23, 66-68). The left (LV) and right (RV) ventricle are separated and five slices each, perpendicular to the origin of the left and right coronary artery, from the base to the apex are obtained. Serial sections, 4 μm thick, are collected, 200 μm apart, for a total of approximately 30 sections per ventricle. These sections include the entire thickness of the LV or RV wall so that the left and right coronary arteries are sampled from their origin near the aorta to the level of resistance arterioles and capillaries. The various segments of the coronary arteries are identified by staining smooth muscle cells (α-SMA, calponin), endothelial cells (PECAM-1, vWF) and adventitial fibroblasts (procollagen). Vascular progenitor cells (VPCs) are recognized with antibodies specific for c-kit and flk1. Transcription factors specific for vascular (GATA6, Ets1, VEZF1) and myocyte (Nkx2.5, MEF2C) lineages are detected by a mixture of antibodies. Additionally, the presence of junctional proteins (connexin 43, 45, 40, 37; VE-, N-, R-, T-cadherin) between VPCs and between VPCs and endothelial cells (ECs), smooth muscle cells (SMCs) and fibroblasts is assessed. These analyses are all performed by con focal microscopy (13, 16, 21-23, 33, 53, 183).

Size, number and cellular composition of vascular niches. The methodology employed in this study has been previously described (See ref 53). Briefly, in each vascular niche, multiple parameters are measured: number and diameter of primitive and committed cells; long and short diameter of cell clusters. The volume of each niche is calculated assuming a shape which will vary from an ellipsoid to spherical configuration. The number of niches, VPCs and committed cells are expressed per length of coronary arteries, arterioles and capillaries (148, 183).

BrdU pulse-chase assays. The protocol below is based on the assumption that the cell cycle lasts 24 hours and S phase 8 hours. Three assays are performed to identify 1) slowly-cycling VPCs; 2) transition of VPCs from the stem cell compartment to the amplifying cell pool; and 3) EC and SMC lifespan and their turnover rate.

Short-term pulse-chase assay. Mice are injected with BrdU 3 times in 8 hours (length of S phase) and sacrificed ~15 min after the last injection (Pulse) or 1, 3 and 7 days later (Chase). If VPCs control cell turnover in the vessel wall, the following results are anticipated: Pulse: All BrdU-labeled cells are expected to be bright. BrdU-bright cells are cycling cells that have incorporated BrdU and correspond to VPCs and amplifying cells. Differentiated ECs and SMCs are not expected to be BrdU-positive at this time point. Chase: Following 1, 3 and 7 days of chasing, BrdU-bright and BrdU-dim cells may be found. Because of the short chasing period, VPCs are predicted to be bright. VPCs are hypothesized to divide rarely and asymmetrically. The daughter stem cell will be BrdU-bright and the daughter committed cell will undergo rounds of division and simultaneously differentiate, i.e., amplifying cells. Due to the low turnover rate of ECs and SMCs in the vessel wall (184-188), a few BrdU-dim ECs and SMCs may be present and most likely constitute the progeny of VPCs. Alternatively, BrdU-dim ECs and SMCs may derive from already committed amplifying cells that incorporated BrdU during pulse. The number of BrdU-dim ECs and SMCs should increase with time of chasing.

Long-term pulse-chase assay. Mice are injected with BrdU 3 times/day for 4 days and sacrificed ~15 minutes after the last injection (Pulse) or 4 and 8 weeks later (Chase). Pulse: BrdU-labeled VPCs, ECs and SMCs will consist mostly of BrdU-bright cells because cycling cells will continue to incorporate BrdU preventing its dilution. The number of BrdU-labeled cells provide information on the cumulative growth rate within the vessel wall in 4 days. Chase: Because of the long period of chasing. BrdU-bright cells detected at 4 and 8 weeks correspond to slowly or rarely cycling cells that were in S phase during pulse and did not divide during chase. If these cells express c-kit and flk1, they correspond to long-term label retaining cells, i.e. VPCs. BrdU-dim cells are interpreted as cells that underwent label dilution during chase, i.e., the progeny of VPCs that incorporated BrdU during pulse or the progeny of BrdU-labeled amplifying cells. BrdU-negative cells are considered cells that have lost the label as a result of multiple (>10) rounds of divisions (189) with chase or were not cycling during pulse.

Very long-term pulse-chase assay. Mice are injected with BrdU 3 times/day for 4 days and sacrificed 6 months later. Pulse: see above. Chase: Over 6 months, amplifying cells labeled during pulse should have undergone a number of divisions leading to complete loss of BrdU. In comparison with 8 weeks of chasing (see above), the number of BrdU-negative ECs and SMCs should increase and the number of BrdU-positive ECs and SMCs should decrease. Thus, it is reasonable to assume that all BrdU-labeled cells at 6 months are the progeny of BrdU-bright VPCs that incorporated BrdU during pulse and have undergone rare division during the 6 month chasing. This protocol provides evidence in favor of a progenitor-product relationship between VPCs and ECs and SMCs.

In all cases, bright and dim BrdU-positive VPCs are counted. Levels of fluorescence greater than 4,000 and lower than 2,000 units (pixel×average intensity) are considered representative of bright and dim cells, respectively (53). VPCs with intermediate levels of fluorescence, >2,000 but <4,000, are excluded to score long-term label retaining lineage-negative VPCs. Under this condition, the auto fluorescence of the section together with the signal generated by the irrelevant antibody, employed as a negative control for BrdU staining, is <10 units. Labeling >50 units is included. BrdU-negative VPCs are also counted. An identical approach is utilized to evaluate the fraction of EC and SMC nuclei labeled by BrdU, bright and dim. However, EC and SMC nuclei with intermediate fluorescence intensity (>2,000 and <4,000) are included in the analysis.

EC and SMC Lifespan. EC and SMC lifespan are determined by the equations developed for hierarchically structured cell populations (190). This methodology is described in detail in ref. 53.

B. In Vitro Studies

VPCs. VPCs are harvested by enzymatic dissociation and characterized by FACS. VPCs are deposited in individual wells of Terasaki plates (21, 22, 33). Myocyte progenitor cells (MPCs) are similarly isolated and used for comparison.

FACS (MoFlo, Dako). VPCs are incubated with 1-5 µg/100 µl primary antibody against c-kit and flk1 and markers listed below. Primary antibodies are directly conjugated with FITC or Cy5 (33). Bone marrow lineages: CD2 (T cells, Natural Killer cells), CD3 (T cells), CD8 (T cells), CD 11b/Mac-1 (neutrophils), CD11c (neutrophils), CD14 (monocytes), CD16 (neutrophils, monocytes), CD19 (B cells), CD20 (B cells), CD24 (B cells), CD41 (hematopoietic cells), CD34 (HSCs, EPCs). CD45 (leukocytes, mast cells), CD133 (HSCs, EPCs), TER119 (erythrocytes); Vascular lineage: GATA6 (SMC transcription factor), Ets1 (EC transcription factor), Tie-2 (angiopoietin receptors), VE-cadherin (cell adhesion molecule), CD62E/E-selectin (cell adhesion molecule), alpha-SM-actin ($\alpha$-SMA, contractile protein), CD31 (PECAM-1), vWF (carrier of factor VIII), Bandeiraera simplicifolia and Ulex europaeus lectins (EC surface glycoprotein-binding molecules); Myocyte lineage: GATA4 (cardiac transcription factor), Nkx2.5 and MEF2C (myocyte transcription factors), alpha-sarcomeric actin ($\alpha$-SA, contractile protein).

Clonogenicity. VPCs are seeded in single wells (21, 22, 33). Cloning efficiency (number of clones/number of seeded cells) are determined and clones are expanded in F12 medium. For subcloning, cells from a clone are plated in single wells and the formation of clones analyzed. Population doubling time is calculated by linear regression of log 2 values of cell number. BrdU (1 µg/ml) is added for one week to measure the fraction of cycling and non-cycling cells. In view of the long labeling period, BrdU positive and negative cells are considered cycling and non-cycling VPCs, respectively. Ki67 labeling provides the number of cycling cells at the time of observation (21, 22, 33, 191). To determine the self-renewal potential of the founder cell, the number of lineage negative (LinNEG) VPCs are counted within the clone. LinNEG cells are cells negative for markers of vascular cell commitment. Identical analysis is performed in each subclone.

VPC differentiation. Clonogenic VPCs are grown in differentiating medium (DM; $10^8$M dexamethasone). The fraction of cells committed to SMCs (GATA6. TGF$\beta$1 receptor, $\alpha$-SMA, calponin), ECs (Ets1, VEZF1, CD31, vWF, VE-cadherin) and myocytes (Nkx2.5, MEF2C, $\alpha$-SA, $\alpha$-actinin, troponin I, troponin T, cardiac MHC, connexin 43, N-cadherin) is studied by FACS and immunocytochemistry (33). MPCs are used for comparison. Cell differentiation is confirmed by real-time RT-PCR.

Functional competence of differentiated progeny. For SMC differentiation, cells are grown in collagen IV-coated dishes in DM supplemented with 1 ng/ml human recombinant TGF-$\beta$1 (192). Cells with electrophysiological properties of adult SMCs are defined. For EC differentiation, cells are seeded in methylcellulose plates (Methocult) with 100 ng/mL VEGF. Colonies taking up DiI-Ac-LDL and binding lectin are defined (193, 194).

Calcein dye transfer assay. SMCs, ECs and fibroblasts are loaded with calcein-AM and VPCs are labeled with DiI (53). Labeled VPCs are cultured in the presence of SMCs, ECs and fibroblasts for 2 hours. This approach is followed for the detection of functional gap junctions between VPCs and putative supporting cells. Since calcein does not transfer spontaneously between cells, the presence of green fluorescence in VPCs will be indicative of the transfer of calcein through functional gap junctions to VPCs. This analysis is done by two-photon microscopy. Then, the same preparations are fixed, stained for connexins, and examined by confocal microscopy to confirm in the same cells that calcein transfer is mediated by functional gap junctions (53). In additional experiments, the gap junction blocker heptanol (53) is added to the cells prior to their co-culture.

Vessel culture. Coronary arteries are isolated to test the ability of clonogenic VPCs to engraft. Coronary arteries are loaded with calcein (green), cultured and placed on the stage of a two-photon microscope enclosed in a chamber at constant temperature, 37° C., and CO2 concentration, 5%. A suspension of ~10,000 DiI-labeled VPCs (red) is allowed to come in contact with the vessel lumen or adventitia. The transfer of calcein (green) to DiI-labeled cells (red) is recorded continuously for 48 hours by two-photon microscopy. The appearance of green fluorescence in the DiI-labeled VPCs (red) documents the formation of functional gap junctions. To determine efficiency of engraftment, VPCs positive for DiI and calcein are counted in the vessel wall together with the sites of engraftment with ECs, SMCs, fibroblasts, myofibroblasts and pericytes (195, 196). The ability of VPCs to invade the vessel wall from the lumen or adventitia and establish adherens and gap junctions with ECs, SMCs and adventitial cells is determined by two photon microscopy and calcein transfer assay in living vessels. Two-photon microscopy allows us to document the speed of migration of VPCs. Presence of cadherins and connexins between VPCs and vascular cells are evaluated after fixation by confocal microscopy. ECs, SMCs, fibroblasts and pericytes are identified respectively by vWF, calponin, procollagen and NG2-proteoglycan (33, 195, 196). VPC commitment is determined by expression of transcription factors and cytoplasmic proteins.

C. Characterization of VPC and MPC Niches

Figure 8:
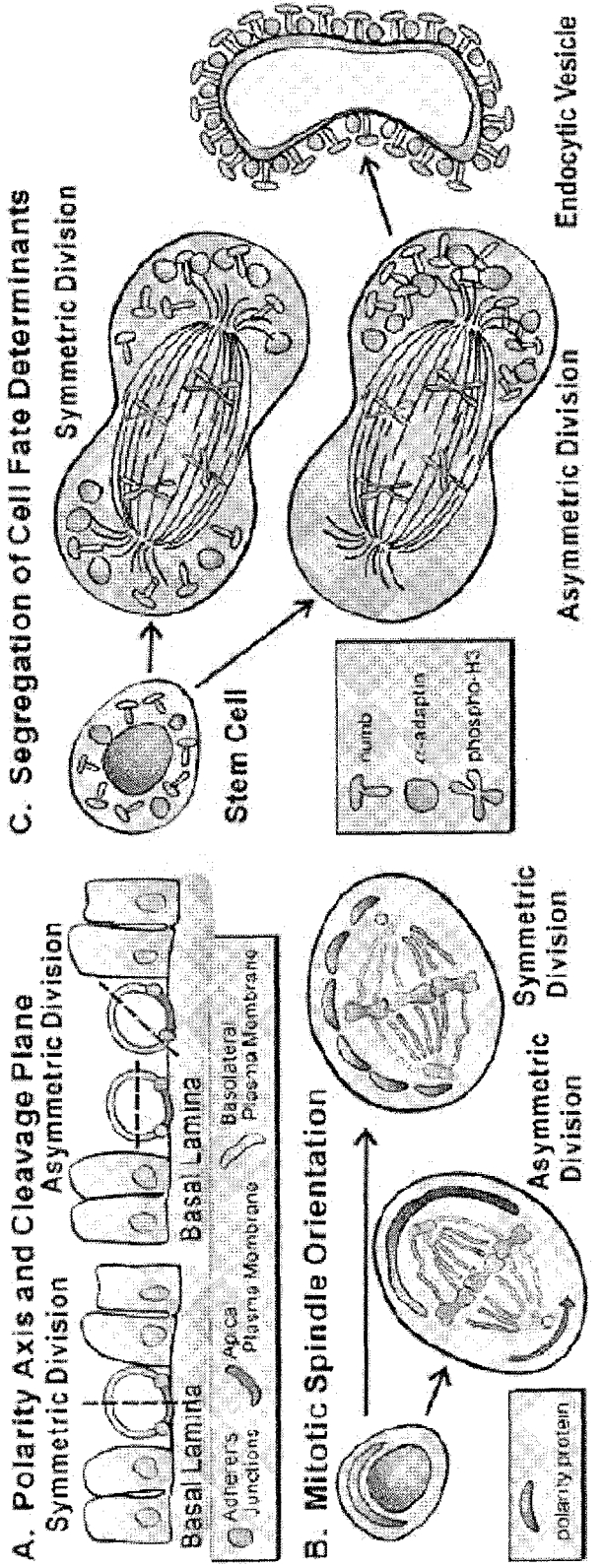

The niche microenvironment controls the number of progenitor cells (i.e. stem cells) and their progeny by influencing the pattern of division. Progenitor cells self-renew by symmetric division, which generates two daughter stem cells, or by asymmetric division, which generates one daughter cell that is identical to the mother cell and a second daughter cell which has a separate fate (71-80). The non-stem cell sister is a short-lived committed PC that proliferates and simultaneously differentiates, i.e., the amplifying cell (18, 19, 81, 82). Upon maturation, the amplifying cell cannot divide further; it has reached terminal differentiation and growth arrest. The terminally differentiated cell may retain only the ability to increase in size undergoing hypertrophy (15, 18-20). Asymmetric cell replication can occur by three mechanisms (FIG. 8): (a) Generation of cell polarity which is determined by basal contacts (basal lamina) and lateral interactions (neighboring cells) (83-88); (b) Orientation of the mitotic spindle which is controlled by spindle-polarizing factors (89-94); and (c) Segregation of cell fate determinants into one of the daughter cells (95-99).

Figure 9:
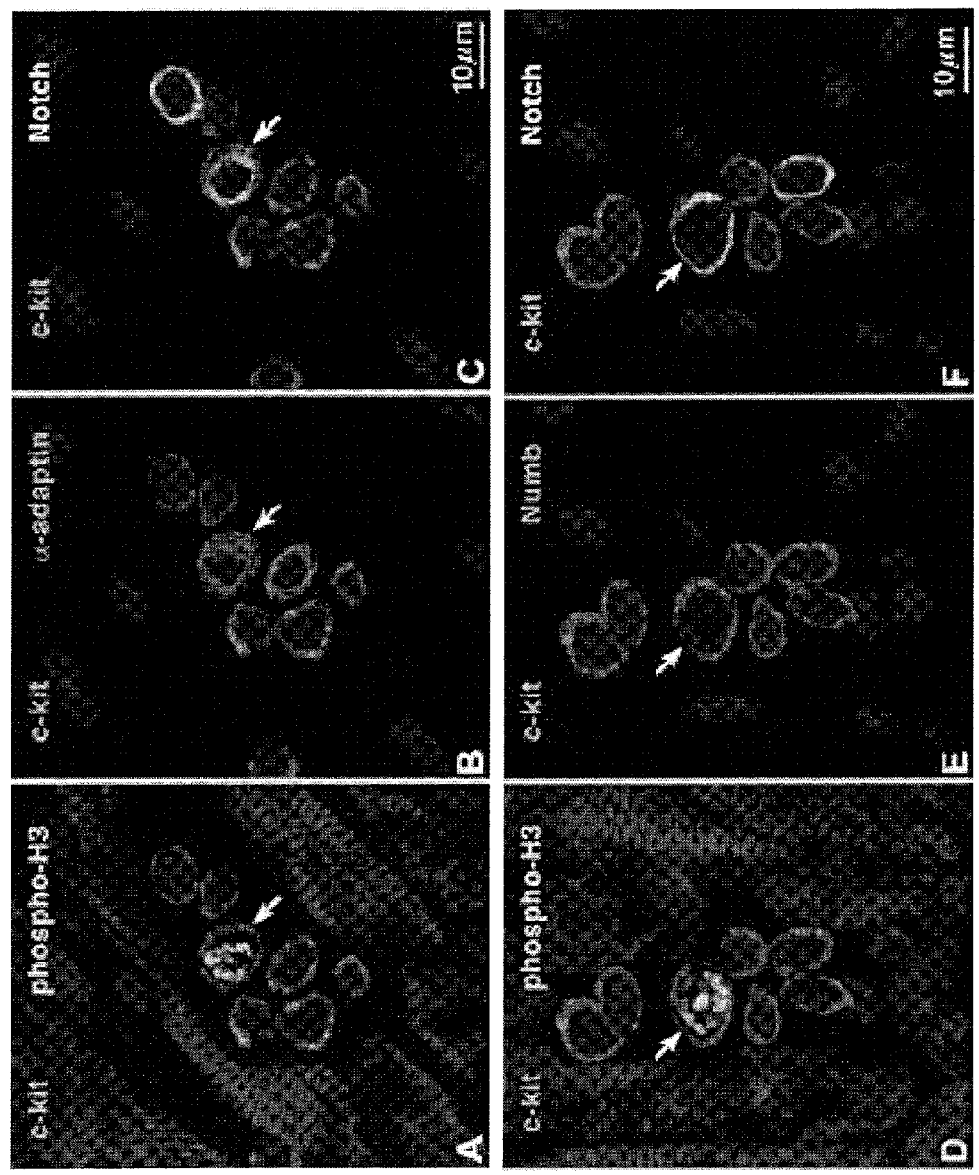
FIG. 9. MPC division. A-C: Myocardial niche with 7 MPCs (c-kit, green); 1 symmetrically dividing MPC (A: phospho- H3, yellow, arrow) shows α-adaptin (B: magenta, arrow) and internalized Notch (C: white, arrow) at both poles. D-F: Myocardial niche with 7 MPCs; 1 asymmetrically dividing MPC (D: phospho-H3, yellow, arrow) shows Numb (E: magenta, arrow) and Notch (F: white, arrow) at one pole of the cell.

The lack of epithelial organization in the heart together with the absence of a well-defined basal lamina surrounding the vascular and myocardial niches (FIGS. 4 and 5) makes it impossible to define an apical-basal axis and recognize the polarity of VPCs and MPCs. Similarly, the cleavage plane that dictates the orientation of the mitotic spindle is strictly related to the apical-basal polarity (84, 86-88, 90, 92). Thus, cell fate determinants are employed to characterize the pattern of VPC and MPC division as shown in our data (FIG. 9).

The inhomogeneous intracellular segregation of selective proteins in daughter cells at the time of mitosis may constitute the intrinsic determinant of VPC and MPC fate. Genes, including Numb, α-adaptin and members of the Notch pathway, interact to enable progenitor cells (i.e. stem cells) to produce differently destined sibling cells (80, 97-99). Notch signaling mediates numerous developmental cell decisions. Although some controversy exists (100), Notch preserves the pool of neural stem cells in the prenatal and adult brain (101-107). In the hematopoietic system, Notch often leads to transcriptional suppression of lineage-specific genes, restricting the number of cells that adopt a specific fate (108, 109). Numb can segregate to one of the two daughter cells or be equally distributed in the cytoplasm of both daughter cells (80, 97-99). Numb is expressed during mitosis, from late prophase to telophase, and in the early stages of life of the new daughter cell (110). Numb localizes to endocytic vesicles and binds to the endocytic protein α-adaptin inducing the internalization and inactivation of the Notch receptor (111). Therefore, asymmetric partitioning of gene products at mitosis conditions cell fate (FIG. 8): cells that receive Numb become unresponsive to Notch while Numb-negative cells retain their responsiveness to Notch and adopt the phenotype associated with Notch activation (80, 86, 112). Signaling through the Notch receptor can occur only between closely adjacent stem cells and supporting cells. Notch ligands are transmembrane proteins. Upon ligand binding, the Notch receptor is cleaved so that its intracellular domain is translocated to the nucleus where it forms complexes with transcription factors of the recombinant DNA binding protein (REP) family (113-115). This pathway may be operative in the heart and regulate stemness or commitment of VPCs and MPCs (116).

Figure 10:
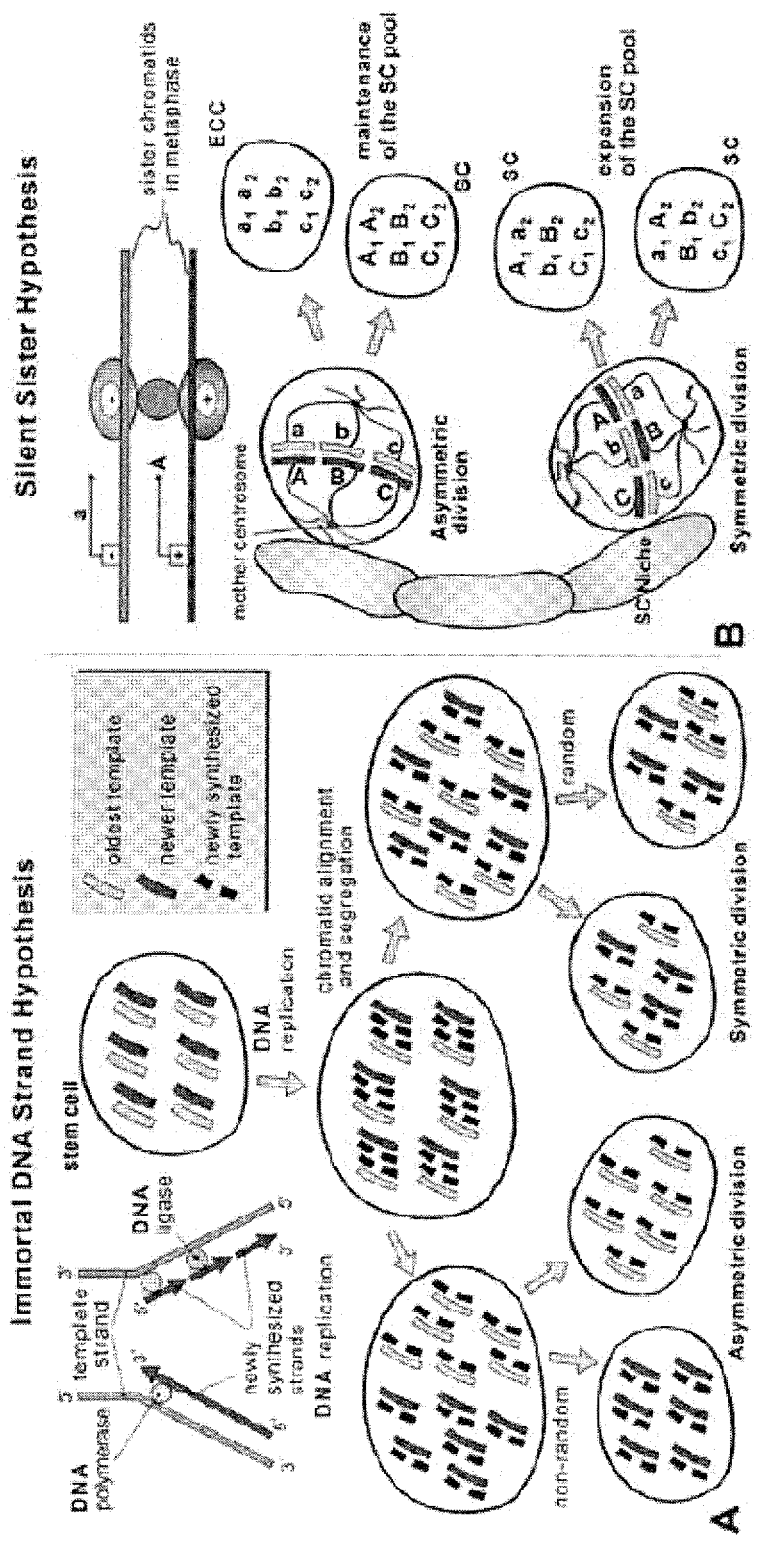
FIG. 10. Immortal strand and silent sister theories. (A) During mitosis, the oldest template (blue) and the newer DNA strands (red) randomly segregate in the daughter cells (blue and red) or the oldest template DNA strands co-segregate in the daughter stem cell (blue). (B) Chromatid-specific segregation of chromosomes during mitosis results in the silencing of stem-related genes in the daughter early committed cell (FCC). Copies of the parental genes are indicated by 1 and 2. With asymmetric division, the stem cell (SC) inherits active (ready to be transcribed) self-renewal genes (capital letters) while the ECC inherits repressed self-renewal genes (lower case letters). With symmetric division, two cells identical to the mother SC are formed. If these cells receive appropriate signals from the niche environment, they will restore the gene expression typical of SCs and acquire the SC phenotype (adapted from ref. 129).

A relevant aspect of asymmetric division of adult somatic stem cells is cosegregation of the template DNA strands ("oldest") in the "mother" cell (117, 118). Template DNA strands are duplicated during S phase when the new DNA strands are formed. During mitosis of non stem cells, original template and synthesized DNA strands are randomly segregated in the daughter cells (119). However, it has been suggested that adult somatic stem cells are capable of cosegregating the original template DNA strands ("oldest") in consecutive divisions (120) so that the daughter cell that inherits the "oldest" template DNA retains stem cell features while the daughter cell that acquires the "newer" DNA strands enters the transit amplifying pool (FIG. 10).

The role of VPCs in vascular cell turnover and growth, and the role of MPCs in cardiomyogenesis may be dictated by differences in their intrinsic properties or signals in the separate niche microenvironment, or both. Possibly, the inherent features of stem cell classes can be determined by characterizing their transcriptional profile with oligonucleotide microarray techniques (133-137). These methods provide the opportunity to compare gene expression between distinct progenitor cell types and possibly recognize genes or clusters of genes involved in self-renewal, multipotentiality and lineage specification (137-1139). The ability of VPCs and MPCs to self-renew and undergo asymmetric division may be linked to a common genetic signature of these cell classes. This shared core of genes may correspond to those highly expressed in all uncommitted cells: Oct4, Nanog and Sox2 (140-142). A signature set of VPC and MPC genes may also exist and help to define the different function of these cells in cardiac homeostasis. We have begun to use this approach for understanding the ability of bone marrow progenitor cells (BMPCs) to generate functional myocardium after infarction (66-68, 143-145). Progenitor cells resident in the bone marrow and the heart share a core of "stemness" genes but each progenitor cell appears to express tissue-restricted genes that may determine the efficiency of differentiation into specific lineages (FIG. 11).

Our data suggest that the Notch pathway is involved in the lineage specification of MPCs to myocytes. New myocytes, however, retain a poorly differentiated dividing phenotype (amplifying cells) and contribute to the expansion of the cardiac cell pool. Notch signaling may be equally relevant to the differentiation of VPCs and the generation of amplifying ECs and SMCs. In the search for the molecular control of MPC commitment, we have found that a perfect consensus site for the Notch effector protein, RBP-Jk, is present in the promoter region of Nkx2.5. This suggests that Nkx2.5 is a novel target gene of Notch. This possibility is supported by several initial studies which included immunohistochemistry, band-shift assay, chromatin immunoprecipitation and beta-galactosidase reporter assay. Notch inhibition in vivo attenuates cardiomyogenesis after infarction. In the acutely infarcted heart, there is a consistent localization of the active form of Notch in EC and SMC nuclei of newly formed coronary vessels (FIG. 12). The Notch ligand Delta 4 accumulates in the wall of these developing vascular structures, suggesting that this ligand receptor interaction in VPCs may promote vasculogenesis.

Example 2

Restoration of Vascular and Myocyte Niches May Reverse Heart Failure

Heart failure may be a stem cell disease. The alteration in coronary perfusion and muscle contractile behavior of the decompensated heart may result from depletion of functional VPCs and MPCs which become unable to form a number of vascular cells and cardiomyocytes required to counteract the abnormal hemodynamic load. Although multiple variables including defects in hormonal regulation, calcium metabolism, contractile regulatory proteins, and complex signal transduction pathways with upregulation or downregulation of a variety of gene products have been recognized, the initial triggering event of heart failure remains obscure (157, 236, 237).

Pressure loading induces concentric ventricular hypertrophy, in which wall thickness increases without chamber enlargement (148, 238-240). In its compensated form, mural thickening is the result of an increase in myocyte diameter and/or myocyte number in the absence of tissue injury (238-242). These events lead to an increase in ventricular mass-to-chamber volume ratio that normalizes the abnormal elevation in systolic stress. These adaptations constitute the anatomical counterpart of compensated concentric hypertrophy and are typically present in patients with aortic stenosis (15) or systemic hypertension (243) with modest ventricular dysfunction (243-245). However, the long-term effects of increased pressure loads result in expansion in cavitary diameter and relative wall thinning, altering the balance between ventricular mass and chamber volume, on the one hand, and afterload, on the other (246-248). These factors define concentric hypertrophy in its decompensated stage in which circumferential systolic and diastolic stress are increased. Multiple foci of myocardial damage represented by areas of replacement fibrosis across the ventricular wall become apparent and chamber volume expands with time (246). Chronic ventricular dilation is the critical determinant of the initiation of ventricular dysfunction and its progression to terminal failure (148). Systemic hypertension is one of the major causes of heart failure in humans (249).

To address the question of whether VPCs and MPCs can be used to alleviate hypertension-induced heart failure, we use two-kidney one-clip renal hypertension in which the increase in systolic blood pressure occurs gradually and worsens with time (250-253). The two-kidney one clip renal hypertension model mimics acquired systemic hypertension in humans (246-248, 254-257). Initially, the increase in systemic blood pressure is paralleled by a corresponding increase in the myocyte and vascular compartment; concentric hypertrophy is apparent and the pressure load is sustained by the expansion in the muscle mass (246, 247, 250-257). Chronically, myocardial damage develops, the chamber dilates, the thickness of the wall decreases and ventricular failure supervenes (246, 247, 257). Structurally, myocyte death, vascular rarefaction and collagen accumulation precede the decline in systemic blood pressure and the onset of ventricular decompensation; and the severity of tissue injury is strictly connected to the extent of functional impairment.

The evolution of hypertensive cardiomyopathy may be conditioned by the formation of dysfunctional vascular and myocardial niches and loss of functionally-competent VPCs and MPCs. Because VPCs and MPCs possess the inherent ability to regenerate an unlimited number of coronary vessels and myocytes, the heart should have the capacity to correct the anatomical changes produced by pathologic loads and sustain pump function indefinitely.

It may be possible to interfere with the etiology of hypertensive cardiomyopathy by repopulating dysfunctional niches and the progenitor cell pool with functionally-competent VPCs and MPCs or by creating new vascular and myocardial niches. Since EGFP-positive VPCs and MPCs are administered, the newly formed niche structures are easily identified and characterized. By definition, a niche has to contain at least one undifferentiated stem cell. In the hypertensive cardiomyopathic heart, old niches may host the new VPCs and MPCs, but putative new niches may be created as well. The presence of groups of engrafted EGFP-positive VPCs and MPCs together with EGFP-negative recipient progenitor cells connected by adherens junctions and gap junctions allows us to define expanded niches while pockets of EGFP-positive VPCs and MPCs only will reflect the generation of putative new niches.

Specific Methods

Figure 13:
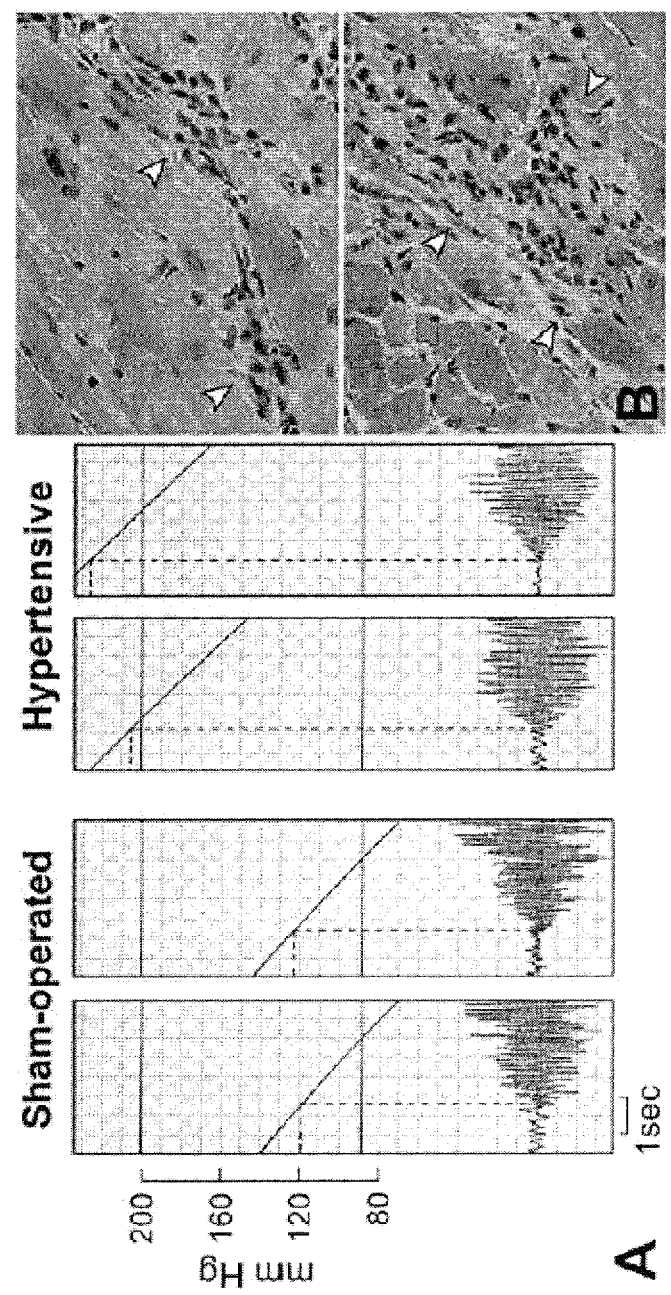
FIG. 13. Tail-cuff measurements of blood pressure in sham-operated mice and mice subjected to renal artery clipping (4 weeks). Renal artery stenosis is associated with a marked increase in arterial blood pressure (A) and multiple foci of replacement fibrosis (B).

Hypertension. Renal hypertension is produced in female mice at 4 months of age. Under anesthesia, a silver clip with an aperture of 70 µm is placed on the left renal artery while leaving the controlateral artery untouched (246, 247, 254). Blood pressure increases in 10-15 days after renal artery clipping and further with time. Sham-operated animals are used as control. Arterial blood pressure is measured by the tail-cuff method every 15 days. Systolic blood pressure greater that 150 mmHg is indicative of hypertension (FIG. 13).

Echocardiography. Echocardiography is performed every two weeks in un-anesthetized mice using a Sequoia 256c (Acuson) equipped with a 13-MHz linear transducer (15L8) (23, 33, 145).

Cell implantation. VPCs and MPCs are isolated from β-actin-EGFP male transgenic mice as described in Example 1 and injected in the myocardium of female hypertensive mice following the recognition of ventricular dysfunction established by echocardiography. This is expected to appear ~3 months after the onset of hypertension and to deteriorate further at 6 months. Six injections, two at the base two at the mid-region and two near the apex are performed. Each injection consists of 10,000 VPCs, 10,000 MPCs or 5,000 VPCs and 5,000 MPCs for a total of 60,000 cells in each case. Mice injected with PBS and untreated sham-operated mice are used as controls. Short-term studies at 1, 3 and 7 days after cell implantation evaluate homing and engraftment of donor VPCs and MPCs (145). The distribution of EGFP-positive male VPCs and MPCs in new niches and pre-existing niches is also established. At 1 and 2 months, the progeny of the injected cells is evaluated. Additionally, the morphometric approach discussed in Example 1 will be employed to define number, size and composition of VPC and MPC niches.

Ventricular performance. At sacrifice, animals are anesthetized and the right carotid artery cannulated with a microtip pressure transducer (Millar SPR-671). A 3 lead ECG is also obtained. A four channel 100 kHz 16-bit recorder with builtin isolated ECG amplifier (iWorks 1X-214) is used. The catheter is advanced into the LV for the evaluation of LV pressures and dP/dt (23, 33, 145). The heart is fixed by perfusion as described in Example 1.

Integration of regenerated myocardium with recipient myocardium. Calcium transient in newly formed EGFP-positive myocytes and resident pre-existing myocytes is determined by an ex vivo preparation and two-photon microscopy (33, 145). For cell physiology see refs. 33 and 145.

Coronary blood flow. This parameter is obtained with non-radioactive microspheres (see ref. 183).

Size, number and cellular composition of vascular and myocardial niches is determined as described in Example 1. Additionally, sections are stained with GFP and Y chromosome to identify the implanted cells and their progeny. Senescent VPCs and MPCs are identified by the expression of p53 and p16 and by measuring the length of telomeres by Q-FISH (16, 175, 258). Apoptotic VPCs and MPCs within the niches are determined by TdT assay.

PCR for GFP and Y-chromosome DNA. These protocols confirm the morphological data.

Cell fusion. Cell fusion between EGFP-positive donor cells and recipient cells are determined by FISH assay for sex-chromosomes (14, 33, 66, 68, 145). Also, VPCs and MPCs are infected with a lentivirus carrying Cre recombinase and injected in hypertensive loxP mice (33).

Data analysis. Hypertension is induced in female mice which will be divided in several subgroups: 2 times of treatment (3 month and 6 months), 4 modalities of treatment (VPCs, MPCs, VPCs and MPCs, and vehicle) and 5 time points at which mice are sacrificed. Each subgroup consists of 10 mice, for a total of 400 mice (2×4×5×10=400). Fifty sham-operated normotensive mice are used as controls. One thousand male β-actin-EGFP transgenic mice will be required to obtain the VPCs and MPCs to be implanted.

The results of this series of experiments are expected to show that the implanted VPCs and MPCs will engraft into the mouse heart both in established niches as well as newly established niches. Mice receiving progenitor cells (VPCs, MPCs, or VPCs and MPCs) will exhibit reduced symptoms of hypertensive cardiomyopathy and heart failure as compared to mice receiving vehicle only. Mice that receive both VPCs and MPCs are expected to show the greatest recovery from symptoms.

Example 3

Identification and Characterization of VPCs and MPCs in Dogs

There are several aims of this Example: (a) To demonstrate that the normal canine heart contains a population of lineage negative c-kit-positive flk1-positive cells, i.e., VPCs, which are located in the intima, media and adventitia of the coronary vasculature including the capillary network; (b) To demonstrate that VPCs are located in vascular niches present in the various segments of the dog coronary circulation; (c) To demonstrate that VPCs can be isolated and expanded from adult dog epicardial coronary arteries and small samples of atrial and ventricular myocardium; (d) To demonstrate that VPCs possess the properties of stem cells and differentiate into ECs and SMCs and only to a limited extent into myocytes; (e) To demonstrate that the canine heart contains a population of lineage negative c-kit-positive flk1-negative cells, i.e., MPCs, which are located in myocardial niches; (f) To demonstrate that MPCs can be isolated and expanded from small samples of atrial and ventricular myocardium; (g) To demonstrate that MPCs possess the properties of stem cells and differentiate into myocytes and only to a limited extent into ECs and SMCs; and (h) To demonstrate that the molecular signature of VPCs differs from that of MPCs.

To achieve these objectives, samples of dog coronary arteries and myocardium are studied. Following the documentation that VPCs and MPCs are present in the canine heart, the question is whether VPCs and MPCs reside in the coronary circulation and the myocardium or translocate from the bone marrow to the vessel wall. Stem cells possess critical properties that can be determined to establish the origin of VPCs and MPCs. Stem cells are stored in niches (370-374) and stem cell quiescence, activation, growth and differentiation are all modulated within the niche structure (375-377). For the documentation of niches within an organ, stem cells have to be found, the anchoring of stem cells to the supporting cells identified and the existence of a progenitor-product relationship established (374, 376, 378).

VPCs and MPCs are expected to be connected to supporting cells by junctional and adhesion proteins represented by connexins and cadherins (379, 381). Connexins are gap junction channel proteins that mediate passage of small molecules involved in cell-to-cell communication (381, 382). Cadherins are calcium-dependent transmembrane adhesion molecules, which have a dual function; they anchor stem cells to their microenvironment and promote cross talk between stem cells and between stem cells and supporting cells (380).

Additionally, the clonal efficiency of VPCs and MPCs is established together with their ability to form a differentiated progeny. This information is critical biologically and clinically. Stem cells have to be self-renewing, clonogenic and multipotent in order to be classified as stem cells (301-304, 311-313).

Finally, the transcriptional profile of VPCs and MPCs is determined to establish shared and distinct genotypic properties among these two populations of primitive cells (383, 386). By comparing global gene expression patterns, we can identify distinct genes or clusters of genes involved in self-renewal, multipotentiality and lineage specification (387, 389). Changes in gene expression is correlated with the phenotype (proteins) and functional state (differentiation) of the cells. Moreover, microarray technologies monitor the expression of thousands of genes offering a comprehensive view of the molecular signature of stem cells with separate roles in vivo (383-386).

The baseline gene expression of undifferentiated VPCs and MPCs is determined first. Moreover, the ability of both VPCs and MPCs to self-renew and undergo asymmetric division may be linked to a common genetic identity of the two cell categories. This shared core of genes may correspond to Oct4, Nanog and Sox2 which modulate self-renewal and multipotentiality (390-396). Also, previously unidentified genes may be recognized. During differentiation, the loss of PC multipotentiality may correlate with alterations in gene expression that regulate vascular and cardiomyocyte genomic identity. The analysis of gene expression profiles includes VPC and MPC clones grown in non-differentiating medium. Clonogenic VPCs and MPCs from individual clones are cultured in "generic" differentiating medium and in "predominantly" EC-producing, SMC-producing or myocyte-producing medium for a short (2 days), intermediate (10 days) and long (21 days) period. The gene expression profile of cells kept in generic medium is compared with that of cells exposed to specific media to determine: 1. Genes involved in unipotent and multipotent specification; 2. Genes involved in early and late commitment and terminal differentiation; and 3. Genes involved in the acquisition of functional competence. Expression profiles are examined by clustering analysis and this approach may identify putative differentiation pathways of VPCs into ECs and SMCs, and MPC into myocytes.

Figure 14:
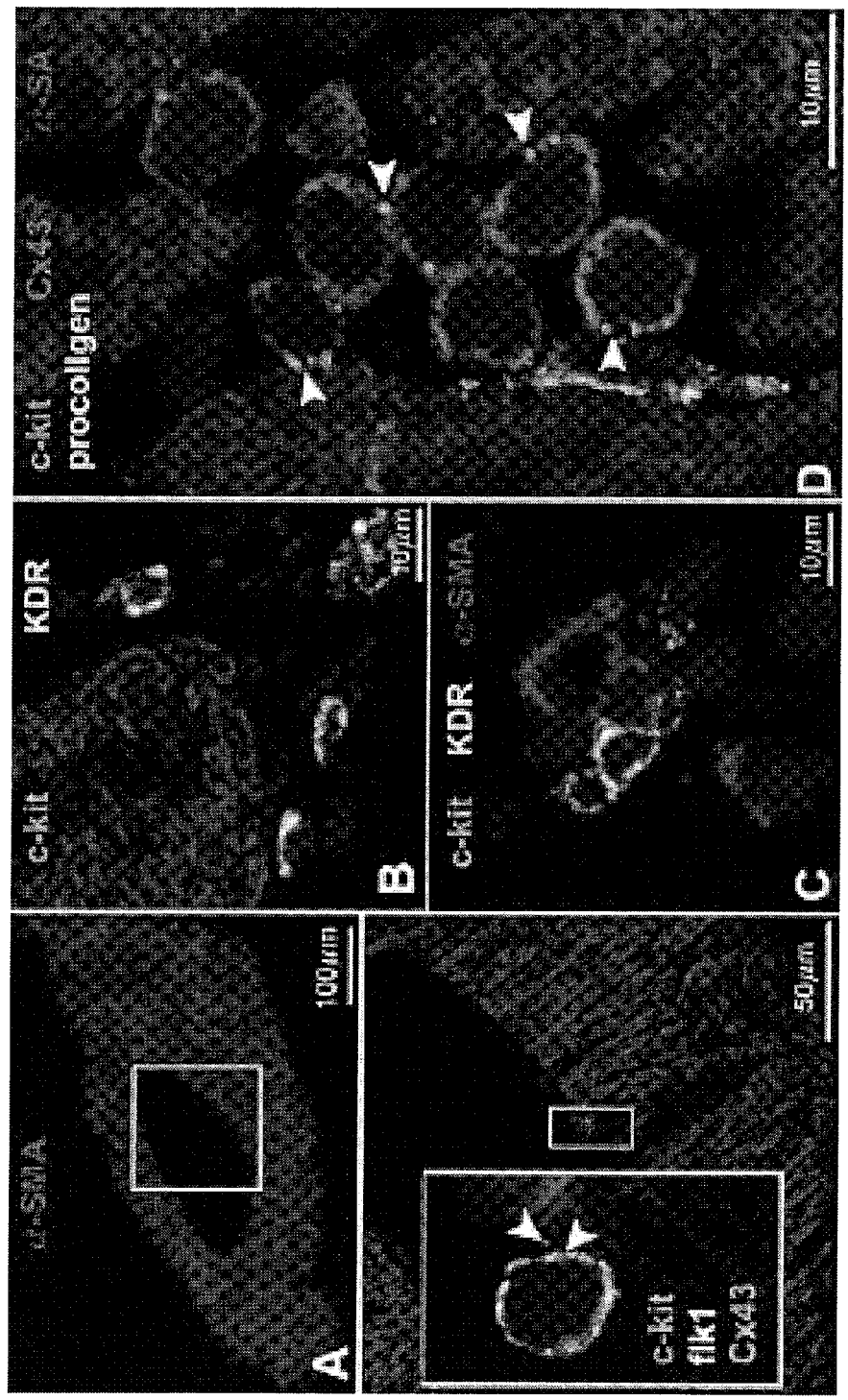
FIG. 14. Vascular and myocardial niches. A: Large section of a dog coronary artery. Area in the rectangle is shown at a higher magnification in the lower panel. One c-kit positive (green) and flk1-positive (white) cell is present in the intimal layer (not stained) of the vessel. The expression of connexin 43 (Cnx 43, magenta) at the interface between the VPCs and endothelial cells is shown in the inset. B, C: Transverse sections of human coronary arterioles (SMCs, α-SMA; red). Clusters of several c-kit positive (green) and flk1-positive (white) VPCs are present in the adventitia (not stained). D: Myocardial niche containing several c-kit positive (green) cells. These cells are flk1 negative; they correspond to MPCs. The expression of connexin 43 (magenta) is shown at the interface between two MPCs, between a MPC and a myocyte (α-SA, red), and between a MPC and a fibroblast (procollagen, yellow) is illustrated in the insets.

Our results have shown that the dog heart possesses a compartment of undifferentiated cells characterized by the expression of the stem cell antigen c-kit; canine c-kit-positive progenitor cells (PCs) are self-renewing, clonogenic and multipotent (301), which are the fundamental properties of stem cells (302, 303). Additionally, this population of c-kit-positive resident PCs can be activated after infarction to invade the damaged tissue and promote the formation of new myocardium which consists mostly of cardiomyocytes and to a limited extent of coronary vessels. In an effort to address the dramatic problem of coronary artery disease (CAD), data have been obtained in dogs and humans supporting the notion that the cardiac c-kit-positive PC pool is not homogeneous but consists of primitive cells distributed separately in the coronary vasculature and in the muscle compartment (FIG. 14).

Figure 15A:
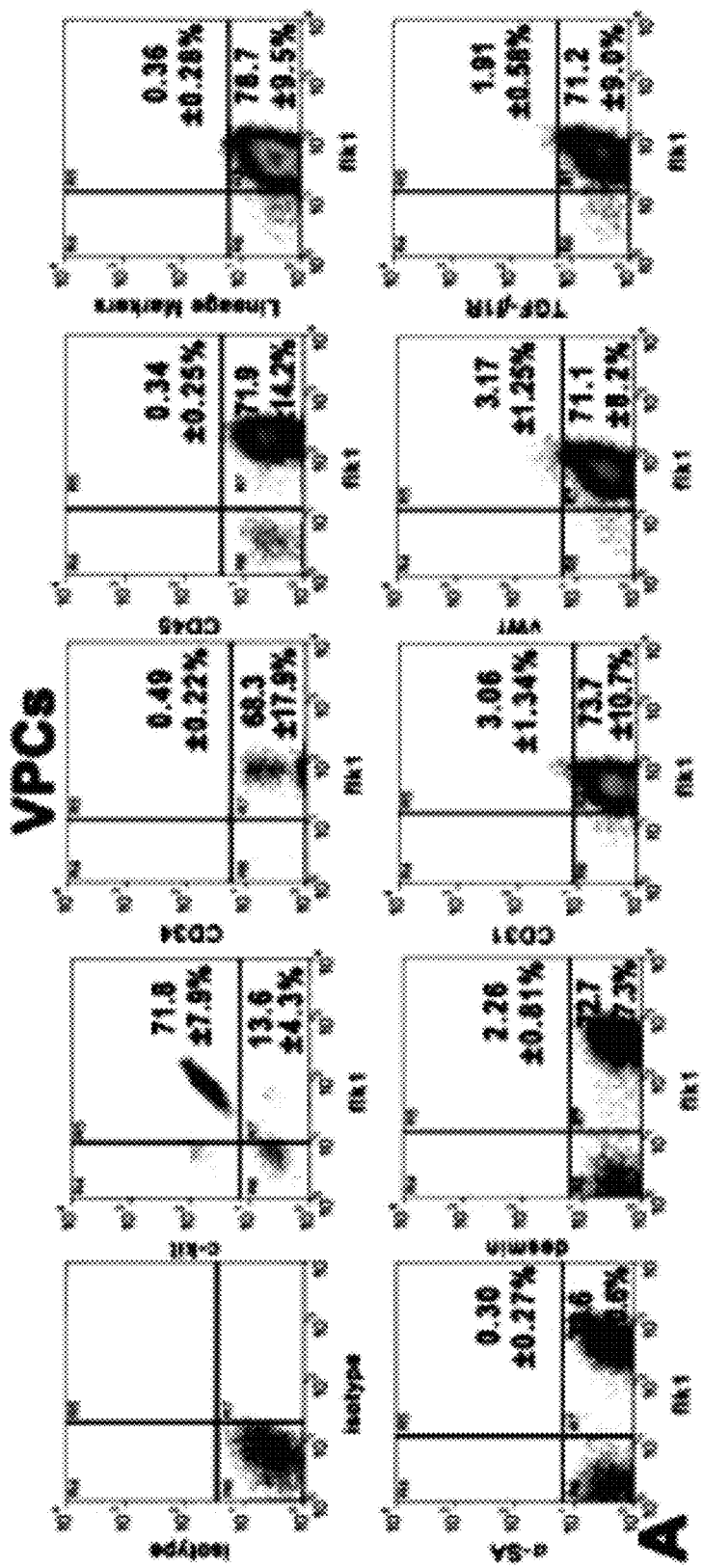
FIG. 15. Phenotypic characterization of VPCs and MPCs. Freshly isolated dog VPCs and MPCs were expanded in vitro (P3-P4) and analyzed by FACS. A: VPCs were negative for hematopoietic markers and α-SA and expresses at very low levels desmin, CD31, von Willebrand factor (vWf) and TGF-β1 receptor. B: MPCs were negative for hematopoietic markers. CD31, von Willebrand factor (vWf) and TGF-β1 receptor and expressed at low levels α-SA and desmin. C: Cytospin preparation of freshly sorted VPC shows the expression of c-kit (green) and flk1 (red), confirming the FACS data.
Figure 15B:
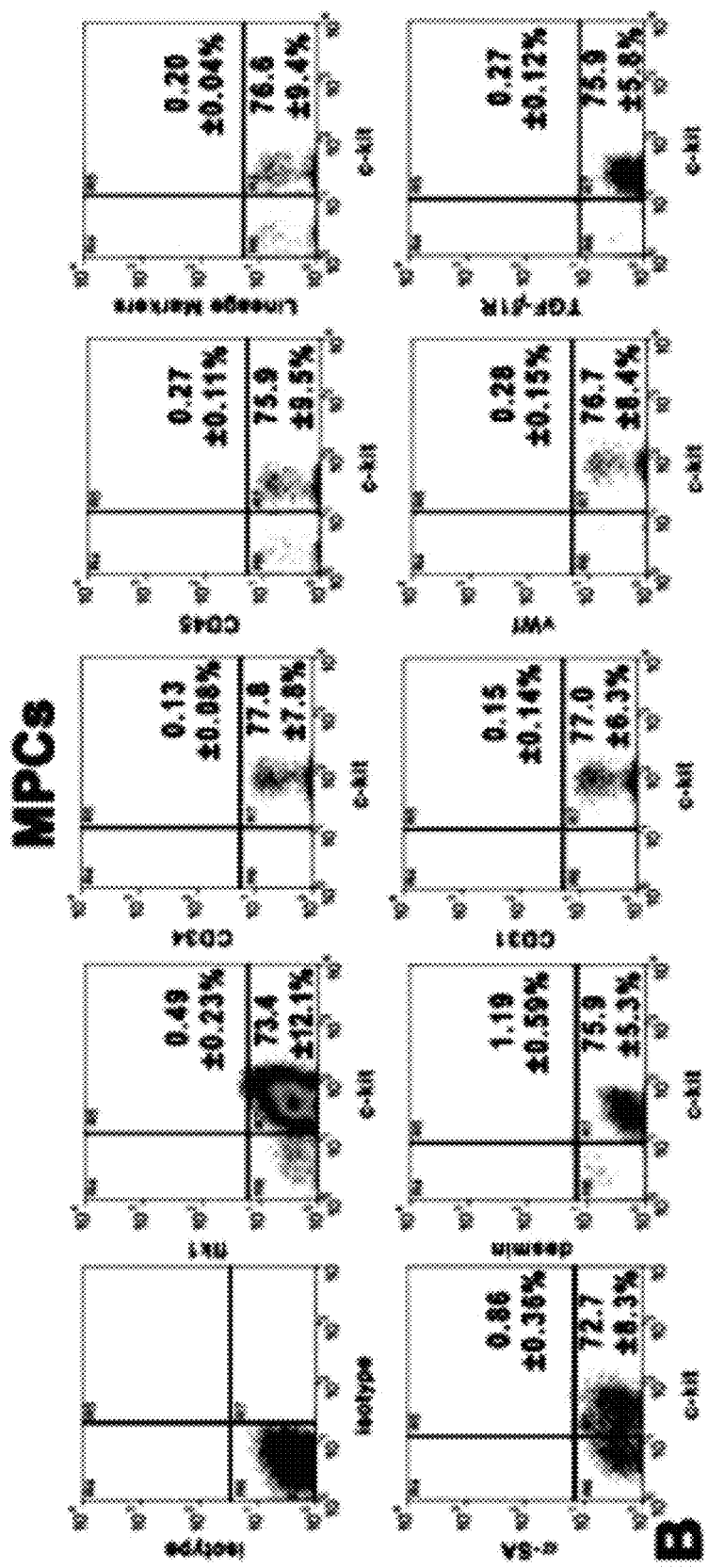
Figure 15C:
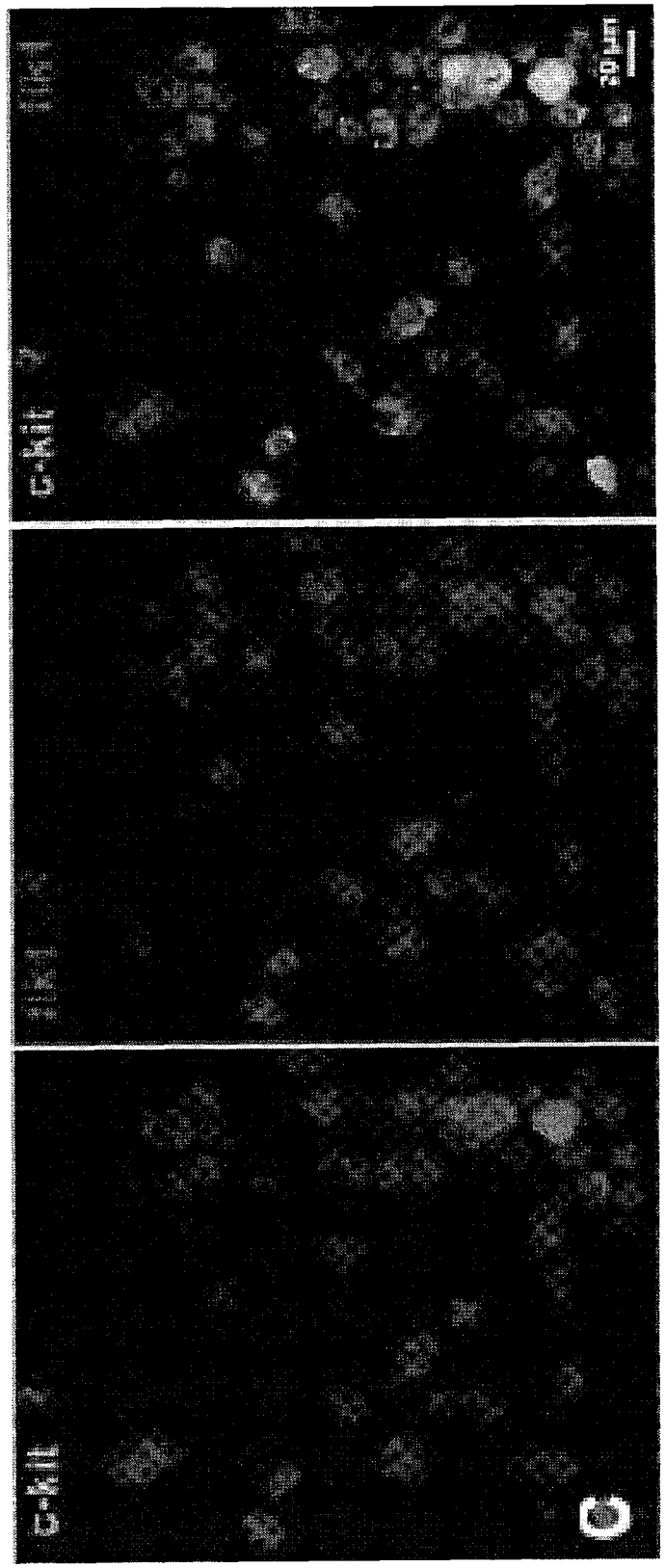

The expression of the VEGFR2/flk1 or kinase domain receptor (KDR) represents the earliest marker of angioblast precursors (305-309) and allows us to recognize and sort separately c-kit-positive PCs with powerful vasculogenic (flk1-positive) and cardiomyogenic (flk1-negative) potential. Our data (FIG. 15) indicate that flk1-positive c-kit-positive PCs are negative for markers of hematopoietic cell lineages including CD34, CD41, CD45, CD133 and a cocktail of antibodies against lineage markers of bone marrow derived cells: CD2 (T cells and natural killer cells), CD3 (T cells), CD8 (T cells), CD14 (monocytes), CD16 (neutrophils/monocytes), CD19 (B cells), CD20 (B cells), CD24 (B cells), CD56 (natural killer cells), CD66b (granulocytes) and glycophorin A (red blood cells). Also, only a small fraction of flk1-positive c-kit-positive cells is positive for the EC adhesion protein CD31 and the SMC TGF-$\beta$1 receptor protein; the myocyte contractile protein $\alpha$-sarcomeric actin is undetectable. Therefore, the dog heart contains a pool of lineage negative flk1-positive c-kit-positive cells that possess the phenotypic properties of multipotent precursors.

Figure 16:
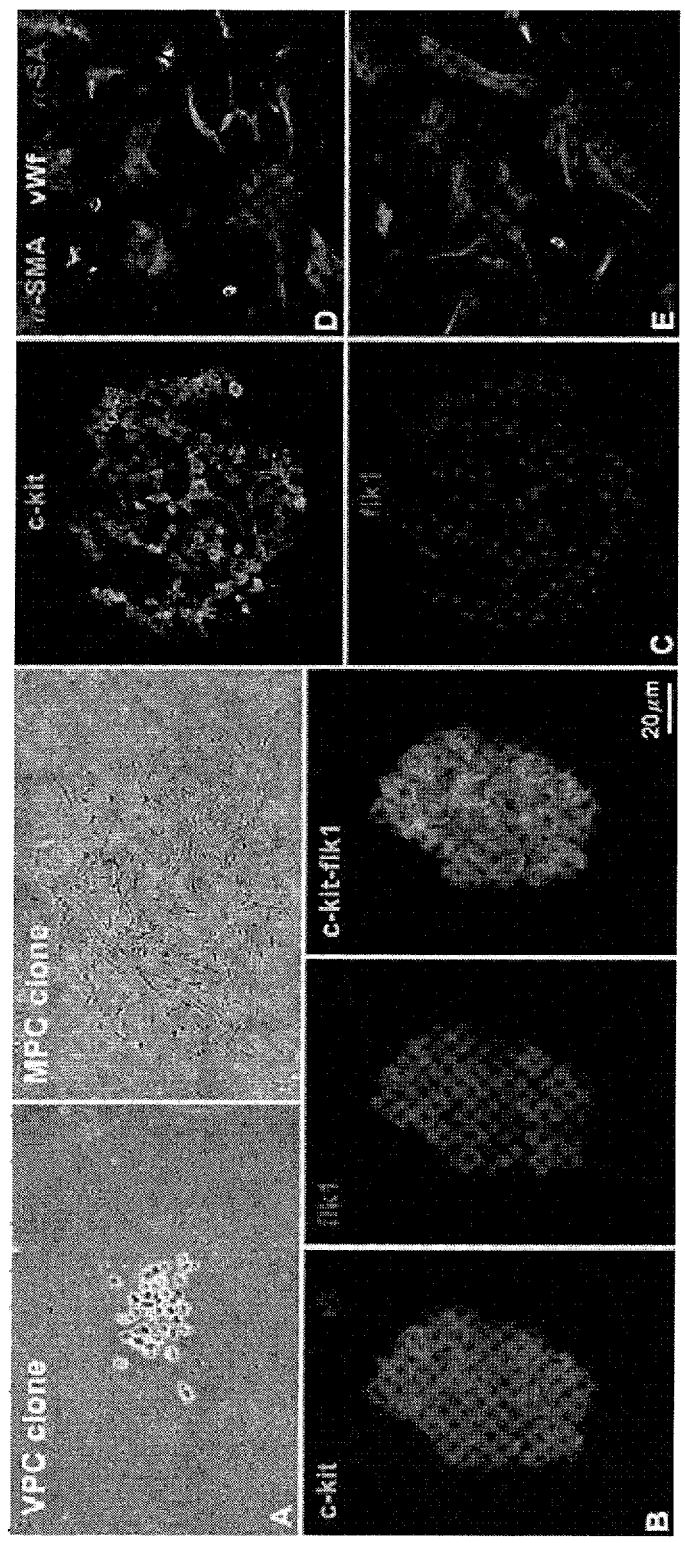
FIG. 16. VPCs and MPCs are self-renewing, clonogenic and multipotent. A: Clones derived from a single VPC and MPC obtained from a canine coronary artery (VPC clone) and myocardium (MPC clone) are shown by phase-contrast microscopy. B: The dog VPC clone is positive for c-kit (green), flk1 (red) and both c-kit and flk1 (yellow). C: The dog MPC clone is positive for c-kit (green) but is negative for flk1. D, E: In differentiating medium, VPCs (D) differentiate mostly into SMCs (α-SMA, green) and ECs (vWf, yellow), while MPCs (E) differentiate predominantly into myocytes (α-SA, red).

The possibility to sort cardiac PCs which express or do not express flk1 in dogs has posed the critical question whether these two categories of cells are self-renewing, clonogenic and multipotent (301-304, 311-316). The acquisition of this information is critical for the definition of these cell classes and characterization of their differentiation behavior. To address this problem, PCs were sorted and individual cells were deposited in single wells of Terasaki plates (301-304, 311-313). After ~3-4 weeks multicellular clones were obtained. Clonogenic flk1-positive c-kit-positive PCs exposed to differentiating medium acquired mostly the EC and SMC lineage and in minimal proportion the myogenic phenotype. Conversely, clonogenic flk1-negative c-kit-positive PCs generated predominantly myocytes and to a limited extent SMCs and ECs (FIG. 16). These results at the single cell level strongly suggest that the PC pool contains two distinct classes of PCs: coronary vascular progenitor cells (VPCs) and myocyte progenitor cells (MPCs). Additionally, these observations point to the presence of an unsuspected VPC located within the wall of coronary vessels distinct from the MPC distributed within the myocardium.

Figure 17:
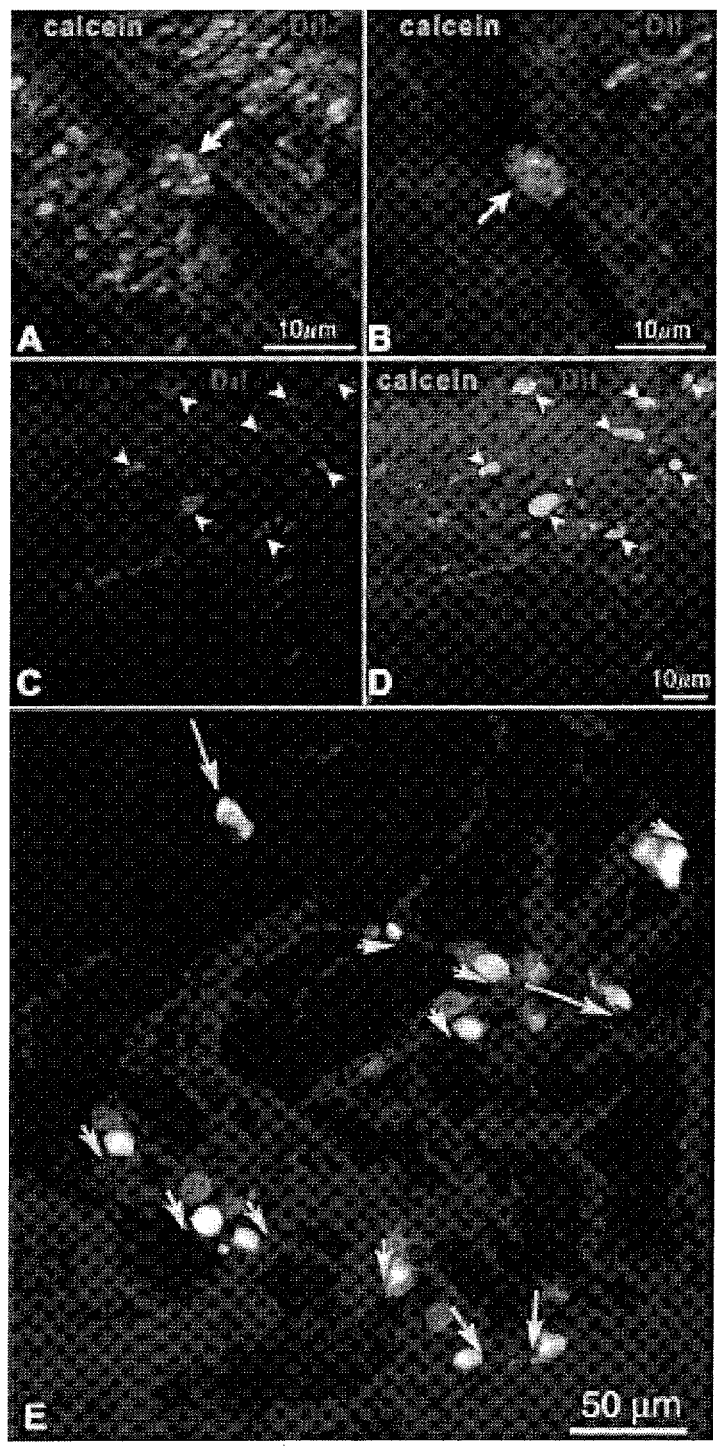
FIG. 17. Engraftment of VPCs into the vessel wall of coronary arteries. A and B: DiI-labeled VPCs (red) were placed on the endothelial surface of calcein-labeled dog coronary artery (green) and examined by two-photon microscopy. After 15 hours, the appearance of green fluorescence in the two DiI-labeled VPCs (arrow) indicates the transfer of calcein through functional gap junctions. C and D: DiI-labeled VPCs (C, red) were co-cultured with a segment of human right coronary artery loaded with calcein (D, green). Several DiI-labeled VPCs show yellow-green fluorescence (arrowheads) which indicates the transfer of calcein through functional gap junctions. Blue fluorescence corresponds to collagen. E: VPCs were co-cultured with a segment of a human coronary artery and their translocation within the vessel wall was followed for 8 hours by two-photon microscopy. This panel corresponds to the superimposition of two images of the same field taken one hour apart. The first corresponds to the position of VPCs in the vessel wall at 5 hours (red dots) and the second at 6 hours (white dots). Yellow arrows indicate the direction of migration. Blue fluorescence corresponds to collagen.

In an additional series of experiments, we have utilized a simplified in vitro preparation to collect information on the migratory behavior and homing properties of VPCs to determine whether a self-renewing, clonogenic and multipotent VPC stored in vascular niches is present in the dog heart and whether it possesses unique phenotypic and functional properties in vitro (FIG. 17). Segments of large coronary arteries isolated from the dog heart and from explanted and discarded human hearts were used. The results of these experiments show: (a) that VPCs have the ability to move from the lumen of intact large coronary arteries into the vessel wall and home to the intima, media and adventitia forming gap junctions and adherens junction with resident ECs, SMCs and adventitial cells; and (b) that VPCs implanted in proximity of the adventitia of intact large coronary arteries or large coronary arteries with endothelial-medial damage and/or adventitial damage home to the adventitia, form connection with fibroblasts, pericytes and myofibroblast-like cells in the adventitia and then migrate to the media and intima establishing junctional complexes with resident cells.

Specific Methods

Specimens for histology and immunocytochemistry. Samples of large coronary arteries together with specimens of myocardium containing intermediate- and small-sized coronary arteries and capillary profiles are examined to detect VPC niches and their distribution within the different portions of the coronary circulation and their localization in the vessel wall. Samples of myocardium from the atria and ventricles are analyzed for the recognition of putative myocardial niches and their distribution in the heart. Vascular niches are compared to MPC niches to establish differences in the phenotypic properties of VPCs, MPCs and supporting cells.

Samples for in vitro studies. Five specimens of canine coronary arteries and myocardium are collected. The in vitro characteristics of VPCs are compared with those of MPCs. VPCs and MPCs are harvested by enzymatic dissociation (304) and single cell suspension characterized by FACS to determine their surface phenotype. Sorted VPCs and MPCs are deposited in individual wells of Terasaki plates.

FACS. VPCs and MPCs are suspended at a concentration of ~100,000 cells/ml PBS. Aliquots of 100 µl of cell suspensions are incubated for 20 minutes at 4° C. with 1-5 µg/100 µl of primary antibody against c-kit and KDR and markers listed below. Primary antibodies are directly conjugated with FITC or Cy5 for FACS analysis (MoFlo, Dako; 304). Antigens studied are as follows: Bone marrow lineages=CD2 (T cells, Natural Killer cells), CD3 (T cells), CD8 (T cells), CD14 (monocytes), CD16 (neutrophils, monocytes), CD19 (B cells), CD20 (B cells), CD24 (B cells), CD34 (HSCs, EPCs), CD45 (leukocytes, mast cells), CD133 (HSCs, EPCs), glycophorin A (erythrocytes); Vascular lineage=GATA6 (SMC transcription factor), Ets1 (EC transcription factor), Tie-2 (angiopoietin receptors), VE-cadherin (cell adhesion molecule), CD62E/E-selectin (cell adhesion molecule), alpha-SM-actin (contractile protein), CD31 (PECAM-1), vWF (carrier of factor VIII); Myocyte lineage=GATA4 (cardiac transcription factor), Nkx2.5 and MEF2C (myocyte transcription factors), alpha-sarcomeric-actin (contractile protein). The specificity of the antibodies against bone marrow epitopes is tested on cells obtained from canine blood.

Clonogenicity and growth properties. Cloning efficiency (number of developed clones/number of seeded single cells) is determined (304). For subcloning, cells from a clone are plated in single wells and analyzed. Clonogenic cells are counted daily and population doubling time is calculated by linear regression analysis of log 2 values of cell number (402). To determine the fraction of cycling and non-cycling cells, BrdU (1 µg/ml) is added one week after plating in a restricted number of wells. In view of the long labeling period, BrdU positive and negative cells are considered cycling and non-cycling, respectively. Ki67 labeling provides the number of cycling cells at the time of observation (301, 304, 311).

VPC and MPC differentiation and immunocytochemistry. Clonogenic cells are grown in differentiating medium (DM, 10-8 M dexamethasone). The number and the relative fractions of cells committed to the SMC. EC and myocyte lineage is studied by FACS and immunocytochemistry (304). Antibodies for SMCs (GATA-6, TGFβ1 receptor, alpha-SM-actin, SM-heavy chain 22), ECs (Ets1, CD31, vWF, VE-cadherin) and myocytes (Nkx2.5. MEF2C, α-sarcomeric-actin, α-cardiac-actinin, troponin I, troponin T, cardiac myosin heavy chain, connexin 43, N-cadherin) are employed. For in vitro immunocytochemistry and later for in vivo immunohistochemistry, all antibodies are conjugated with quantum dots to exclude autofluorescence artifacts see (266, 270, 304).

Functional competence of VPCs. For SMC differentiation, cells are grown in collagen IV-coated dishes in DM supplemented with 1 ng/ml human recombinant TGFβ1 (403). Cells with electrophysiological properties of adult SMCs are defined. For EC differentiation, cells are seeded in methylcellulose plates with 100 ng/mL VEGF. Colonies taking up Di1-Ac-LDL and binding lectin are defined (404).

RNA extraction and array hybridization. Clonogenic VPCs and MPCs and BMPCs are resuspended in Trizol. RNA is extracted and ~1 μg of total RNA is converted to biotin-labeled cRNA using Gene Chip One-Cycle Target labeling kit and hybridized on the human genome array at the Affymetrix Facility of Albert Einstein College of Medicine. A minimum of 3-5 independent hybridizations is performed in triplicates for each condition (385, 405, 406). The MIAME (minimal information about a microarray experiment) guidelines are followed for data presentation (407). The Affymetrix software MicroArray Suite 5.0 (MAS 5.0) is used to generate absolute expression estimates (absent/present call) from the raw data. Software default thresholds are employed to determine the present (P) or absent (A) calls ($\alpha 1=0.04$, $\alpha 2=0.06$, and $\tau=0.015$). The data obtained from MAS 5.0 are then normalized and further analyzed in the Gene-Spring software version 6.2. Per-chip normalization is done as follows: values below 0.01 are set to 0.01, and then each measurement is divided by the 50th percentile of all measurements in that sample. Per-gene normalization is done as follows: each gene is divided by the median of its measurements in all samples. If the median of the raw values is less than 10, each measurement for that gene is divided by 10. Genes are considered to be differentially expressed in VPCs and MPCs only when three criteria are met: (a) Difference in expression is at least twofold; (b) The gene is identified by MAS 5.0 as present in two out of three replicates or present or marginal in all three replicates in the group with the highest expression level; and (c) Difference in expression is significant ($P<0.05$ in an unpaired t-test with Welch's correction). Classification of genes into functional clusters is done by collecting annotations and keywords with the Onto-Express Tool Affymetrix Net Affx, and the Simplified Gene Ontology Tool included in GeneSpring 6.2 Software (408). Microarray data are confirmed by real-time RT-PCR.

Real-time RT-PCR and Western blotting. RNA is isolated using Trizol from clonogenic VPCs and MPCs and BMPCs freshly isolated from the sternum of patients undergoing open heart surgery; 1 μg of RNA is employed for reverse transcription (RT) into cDNA using SuperScript III cDNA synthesis kit (304). RNA is incubated with 5'-phosphorylated oligo(dT) 20 primer. Real time RT-PCR analysis is performed on 7300 Real Time PCR System and run in duplicate using 1/20th of the cDNA per reaction. Gene sequences for primer design are obtained from the NCBI database. Primers are chosen (Primer3 software), and their specificity is tested with electronic PCR using human genome and human transcript database. Cycling conditions are established according to the designed primers. Data are analyzed using the Automatic Baseline of the Sequence Detection software, and the threshold is fixed at 0.05 manually for cycle threshold (Ct) determination. PCR efficiency is evaluated using a standard curve of five serial dilution points; quantified values are normalized against the input determined by the housekeeping gene GAPDH or beta-actin. Real-time RT-PCR products are run on 2% agarose/1×TBE gel. Amplified fragments are cut out, DNA is extracted and amplified and sequences are determined in sense and antisense directions. The expression of selected genes is confirmed at the protein level (301, 304, 311).

Example 4

Implantation of VPCs Generates a Biological Bypass in the Presence of a Stenotic or Occluded Coronary Artery The tight coupling of coronary blood flow to cardiac or myocyte function allows for increases in cardiac output to support normal physiologic function for instance in exercise or pregnancy (331, 342). However, due to the tight coupling and little potential overlap in mechanisms, the heart is left in the precarious position where a limitation in blood flow or loss of cardiac myocytes, together or separately, may have substantial consequences for cardiac pump function. During a limitation in coronary blood flow, due to stenosis or total occlusion of a blood vessel, there is an exponential relationship between flow and function (343) and the limited delivery of oxygen and substrates to contracting myocytes will limit contraction and may result in ischemic cell death. Unlike apoptotic cell death where the myocyte is essentially reabsorbed (344, 345, 346), ischemic cell death results in replacement fibrosis and scarring. If substantial, the scaring will lead to altered cardiac diastolic compliance and function. This can alter cardiac diastolic function (wall tension), and the time and distance over which oxygen diffusion primarily occurs in the heart. However, following myocardial ischemia, blood vessels are lost altering the architecture of the coronary circulation and the delivery of oxygen to support oxidative metabolism in cardiac myocytes. Myocyte contractile or systolic function is reduced or eliminated due to lack of oxygen and substrate, myocytes die leaving scar tissue which alters diastolic function and the diffusion distance for oxygen to the remaining myocytes. Thus remodeling of the heart occurs and this adds to the cardiac dysfunction.

The intimate relationship between the coronary circulation and the cardiac myocytes it perfuses supports the contention that there is an optimum relationship between the two and that both structures are needed to support cardiac performance. Classical therapeutic approaches to the treatment of myocardial ischemia have centered on drugs including clot busters or surgical interventions such as stenting and bypass surgery, for instance, to restore coronary blood flow. These have been largely effective in restoring cardiac function in an ischemic zone especially if the intervention is performed within a few hours after ischemia (347, 348). However if the ischemia lasts for a longer period of time, there may be limited benefit to restoring blood flow since the cardiac myocytes are already dead or have already begun an irreversible process leading to cell death (344). Exciting and still developing therapies address this limitation of cell death by attempting to replace cardiac myocytes in the ischemic zone using cell based approaches (267, 349, 350). In addition if the ischemia is maintained so that the area of the infarct remodels, the architecture of the heart changes so that blood vessels disappear (rarefaction). At that time, opening of or bypassing large arteries alone will be ineffective in restoring blood flow and function in the area of the ischemia since the small vessels including capillaries have been reabsorbed. At some point in time, reperfusion will be ineffective since blood flow will not get to the surviving myocytes and myocyte loss (mass) leads to reduced inotropic state. Thus, it is also necessary to grow a functional coronary vasculature, including large vessels and capillaries during the development of cell based therapies.

Currently attention is being paid to the ability to reverse remodel the chronically ischemic heart via methods to recruit or use stem cells. A recent study by Bearzi et al (304) has shown that injection of human cardiac stem cells labeled with GFP, which were expanded in vitro, at the time of infarction, results in the generation of labeled cardiac myocytes (84% of the cells) and blood vessel cells (8% of the cells). These cells were functionally integrated into the mouse heart and showed contractile function up to 2 weeks after injection. Furthermore, the restructured heart contained a myocyte to capillary ratio of 8/1 with a diffusion distance for oxygen of approximately 18 µm. This ratio is smaller than the 1/3 normally seen in the heart and may indicate an oxygen supply reserve in the newly regenerated heart. On the other hand, the size of the newly developed myocytes ranged from 100 to 1900 $\mu m^3$ somewhat smaller than the average mouse cardiomyocyte, 25000 $\mu m^3$, and this has to be factored into evaluation of the requirements of oxygen in those cells (the oxygen cost of growth and contraction) which is unknown. This study provides strong evidence that these therapies using cardiac derived adult stem cells grow both myocytes and capillaries and are potentially useful.

We have developed approaches to recruit cardiac stem cells to treat myocardial ischemia in the dog heart. There are a number of advantages to this approach including: a) the ability to study the dog in the conscious state free from the complications of anesthesia and recent surgery (353); b) the ability to measure regional and global cardiac function more precisely; c) the ability to design and carry out experiments in a longitudinal design where cardiac function is measured repeatedly over time in the same animal; d) the availability of classic well described models from the literature; and d) the ability to record cardiac function on line in real time and to accurately assess the evaluation the impact of loading conditions on contractility.

The objective of this experiment is to determine whether in the presence of a stenotic or occluded coronary artery catheter-delivered or locally injected VPCs generate a biological bypass which reestablishes blood flow to the distal myocardium restoring in part regional ventricular function.

Figure 18:
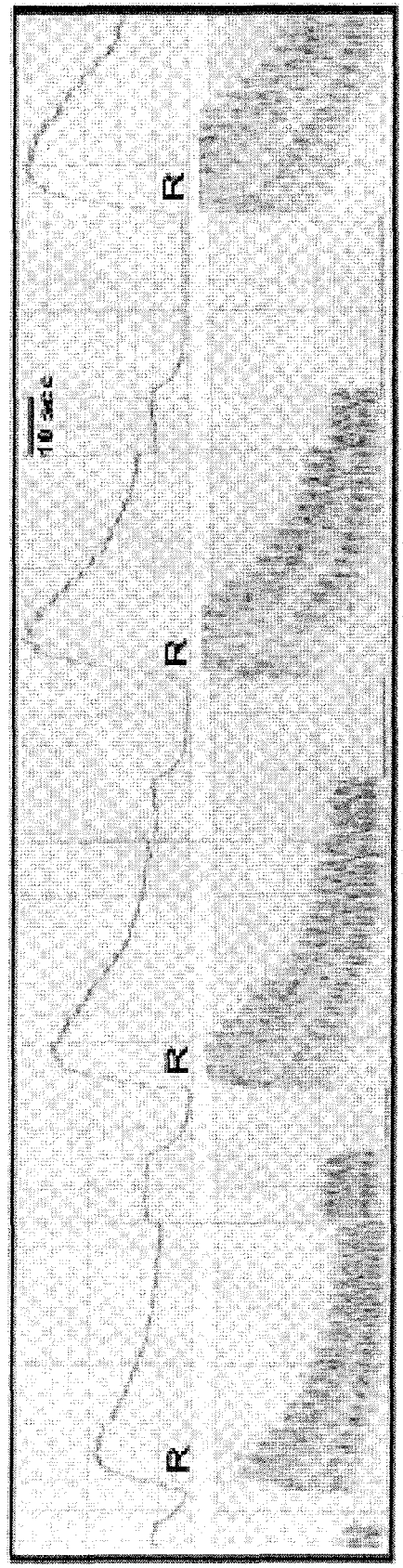
FIG. 18 shows the ensuing reactive hyperemia after (left to right) release (R) 5, 10, 15 and 30 second occlusion of the coronary artery. There is a large hyperemic response which will be used to assess the degree of coronary flow reserve.

Reactive hyperemia is used to assess the extent of the coronary stenosis (ranging from small to critical to producing an infarct). The ensuing hyperemia uses up the coronary reserve and results in characteristic 500% increase in blood flow (FIG. 18) (336-338). During maximum coronary dilation, relying on oxidative metabolism and having increased oxygen extraction from 80 to 85% the oxygen supply to the contracting myocytes also increases approximately 5 fold. Thus the geometry of the coronary circulation, the limitation of oxidative metabolism, an almost maximum oxygen extraction, and the ability to increase coronary blood flow almost 5 fold, account for increased oxygen delivery in the heart.

Cardiac myocytes contract at rates ranging from 40 to approximately 180 b/min in man (and in the conscious dogs that we use). A measure of cardiac contractility, for instance LV dP/dt, can increase about 5 fold in the conscious dog during maximum exercise (339, 340). Together with the tachycardia, this results in an approximate 5 fold increase in cardiac output or slightly greater in cardiac work due to the increase in arterial pressure which occurs during exercise (341). Thus heart rate can increase about 4 fold, contractility approximately 5 fold and cardiac work 5-6 fold during maximum cardiac performance. From this it should be obvious that the coronary circulation is able to accommodate a 5 fold increase in oxygen delivery and the heart is able to undertake about a 5 fold increase in cardiac performance, indicating that over a wide range of cardiac function, there is tight coupling between oxygen delivery and oxygen demand. In fact, when this tight coupling is altered due to altered blood flow regulation or a mismatch between oxygen delivery and consumption, myocyte dysfunction or death ensues resulting in cardiac pump dysfunction. If this dysfunction is large or long lasting heart failure may occur.

Three different protocols are employed in this series of experiments. They are as follows:

Protocol 1.

Rationale: If a coronary stenosis limits blood to a portion of the heart resulting in myocardial ischemia and dysfunction then restoration of blood flow will restore contractile function distal to the stenosis. Thus a therapy designed to selectively create a biological bypass would be unique and effective. The goal of this experiment is to determine if the injection of VPCs into the heart results in the formation of functional blood vessels and results in amelioration of the ischemia due to chronic coronary stenosis.

Specific methods: The dog is trained to lie on the laboratory table and then echocardiography is performed with special attention to the anterior wall. Dogs are instrumented for the measurement of cardiac function (segment crystals/contraction) and with a flow transducer, hydraulic occluder and critical stenosis on the distal LAD. At surgery the stenosis is adjusted to eliminate the reactive hyperemia following a 15 second coronary artery occlusion (a critical stenosis). The left atrial appendage is harvested from which VPCs are isolated and propagated. The chest is closed in layers and the dog allowed to recover. Ten days after surgery, hemodynamics are recorded, the reactive hyperemia examined, and echocardiography performed. This is repeated each week for 2-4 weeks (until the autologous canine stem cells proliferate, estimates are that $10 \times 10^6$/ml cells per animal are used). Once sufficient cells are available, hemodynamics (non radioactive microspheres injected through the left atrium to measure collateral flow) are recorded and then the dog anesthetized with sodium pentobarbital. The dog is taken to the fluoroscopy laboratory and the LAD catheterized for the injection of contrast (without and with occlusion of the LAD) to visualize the collateral circulation. Following this, a specially designed balloon-needle catheter (414) is advanced into the area of the stenosis. The needle is advanced from the catheter and injections of 250 µl of the VPC cell suspension is given 2-5 times. In some of the dogs the cell suspension is mixed with contrast media (414) to visualize the sites of injection. The catheter is removed and the dog is allowed to recover. The dog is studied each week for 4 weeks and microspheres injected with and without occlusion to measure collateral flow. Prior to sacrifice, the cardiac catheterization is repeated to visualize the collateral circulation. At that time, one half of the dogs are anesthetized and the heart perfusion fixed. In the other half, tissue is collected for in vitro studies of microvessel reactivity.

The injection of VPCs results in growth of GFP containing blood vessels, visualization of a well developed collateral circulation at catheterization, and increased deposition of microspheres in the ischemic zone distal to the stenosis. In isolated perfused coronary microvessels, there may be increased flow induced dilation (indicating functional endothelium) and increased agonist induced dilation (indicating enhanced smooth muscle and endothelial function). There may be a relationship between dilation in vitro and the site and amount of GFP staining. There may be an increase in segment contractile function in the ischemic zone that is proportional to the increase in blood flow.

Figure 19:
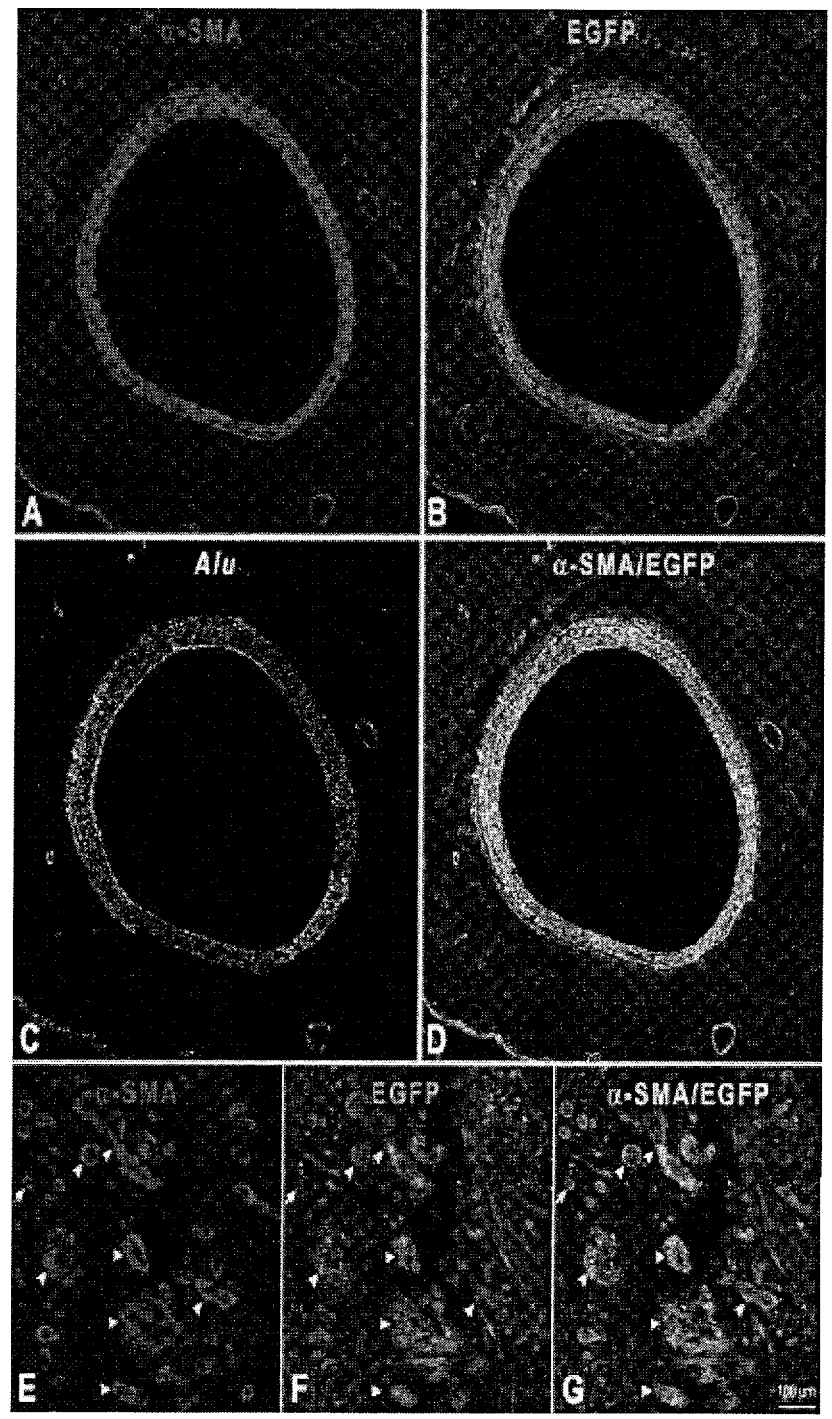
FIG. 19 shows that injection of VPCs resulted in formation of large coronary arteries, 1.5 mm in diameter which stain for A: α-smooth muscle actin (Red), B: green fluorescent protein (green), C: a marker for primate DNA (white, Alu) and, D: the merge of A & B. E, F & G: indicates staining of smooth muscle actin, green fluorescent protein and the merge of E & F, respectively on small coronary microvessels, less than 100 μm in diameter. Thus, the injection of VPCs resulted in formation of large coronary arteries and arterioles.

We have currently studied 6 dogs with a coronary stenosis and injection of vascular stem cells which were labeled with GFP prior to injection into the ischemic region of the dog heart. In these animals, we clearly identified coronary blood vessels labeled with GFP (FIG. 19).

The LAD coronary artery was catheterized and the coronary circulation visualized in three dogs using a fluoroscope. Those dogs were instrumented with a flow transducer, an occluder and a critical stenosis. Injection of contrast in all the dogs indicated the presence of a significant stenosis. One dog had injections of GFP labeled VPCs during the initial surgery (3 weeks prior to study). Most importantly, during occlusion of the LAD using the hydraulic occluder, injection of contrast did not appear in the distal LAD circulation in 2 of the dogs (i.e. there was little collateral blood flow), whereas there was a substantial and obvious appearance of contrast in the distal circulation in the one dog receiving VPCs (evidence of a newly developed circulation) as shown above in FIG. 20A. Hearts were perfusion fixed and tissue sections prepared to find evidence of GFP labeled small blood vessels.

In one dog we created a large infarct with the goal of severely compromising cardiac function to induce heart failure. By ligating the proximal LAD at the first diagonal branch, we reduced ejection fraction from 72% to 29% (FIG. 20B).

Protocol 2.

Rationale: The primary goal of acute cardiac catheterization/stenting and thrombolytics to treat myocardial infarction is to restore blood flow to the area of the infarction, particularly the border zone and thereby reduce or reverse the ischemic damage and contractile dysfunction. Thus, current therapies already are designed to selectively increase blood flow to the ischemic myocardium. There are no therapies designed to increase blood flow after a chronic infarction since the remodeling of the infarct includes disappearance of blood vessels. The goal of this study is to determine if the injections of VPCs into the border and ischemic zone of a distal (small infarct) LAD occlusion results in increased blood flow to the infarct and enhances contractile function. These studies use a small infarction so that the complications of heart failure are not present.

Specific methods: Surgery is performed using general anesthesia and sterile technique for the measurement of cardiac function (including segment function) and with an occluder and flow transducer on the LAD. The left atrial appendage is harvested for the collection of VPCs and MPCs. The dog is allowed to recover for 10 days. Hemodynamic studies, echocardiography and cardiac catheterization is performed and then the dog anesthetized, the distal LAD permanently occluded and the dog allowed 2-4 weeks to recover. After 2-4 weeks the LAD is catheterized to visualize blood flow to the area of the infarct and microspheres injected, then under general anesthesia using an echo-guided spinal needle or Mercator catheter, injections of VPCs (250 µl) are made into the middle of the infarct and then into the border zone (3-5 injections). The dog is allowed to recover and then hemodynamic recordings made each week for 4 weeks. At that time the dogs are anesthetized, cardiac catheterization performed, and microspheres injected and the heart perfusion fixed, or collected for in vitro studies of coronary microvessels.

The results are expected to show an increase in microsphere measured blood flow to the border zone of the infarct and a small increase in segment function (local contraction). There may be evidence of GFP containing blood vessels and in vitro these may have enhanced flow and agonist induced dilation.

Protocol 3.

Rationale: Myocardial infarction in man is often associated with the development of heart failure due to reduced inotropic state (myocyte loss). Furthermore, once a large infarct is established and heart failure evident, the heart failure progresses due to increased wall stress and subsequent remodeling. There are no current therapies which are targeted to the sequence of events leading to the progression of ischemic heart failure. The use of VPCs would be a unique approach to restoring blood flow to a large ischemic area of the LAD. The goal of these experiments is to determine the effectiveness of injection of VPCs as a therapy in the presence of a large established infarction.

Specific methods: In these studies we create a large infarct, sufficient to reduce ejection fraction acutely and permanently by occluding the proximal LAD. Dogs are trained to lie on the laboratory table and echocardiography performed. Dogs are instrumented for the measurement of cardiac function and segment function in the potentially ischemic zone. A flow transducer and hydraulic occluder are placed on the proximal LAD just distal to the first diagonal branch. The left atrial appendage is harvested. The dog is allowed to recover. After recovery and echocardiography, microspheres are injected to measure blood flow and then the dog anesthetized for permanent occlusion of the proximal LAD. The dog is allowed to recover and the size of the infarct determined by echo, following microsphere injection and hemodynamic measures. The infarct is visualized using fluoroscopy. After 2-4 weeks the dog is anesthetized and using an echo guided spinal needle or Mercator catheter, VPCs injected into the middle of the infarct and around the border zone. The dog is allowed 2-4 weeks during which hemodynamics and echocardiography is performed. At the terminal experiment, cardiac catheterization is performed to visualize blood flow to the infarct.

The results are expected to show some increase in GFP labeled blood vessels, in microsphere measured blood flow, and visualized blood flow to the ischemic region and some increase in cardiac function at best proportional to the increase in blood flow.

Example 5

Implantation of MPCs Replaces the Scar with Functionally Competent Myocardium in the Presence of a Stenotic or Occluded Coronary Artery The objective of this series of experiments is to determine whether in the presence of a stenotic or occluded coronary artery catheter-delivered or locally injected MPCs replace the scar with functionally competent myocardium restoring in part regional ventricular function.

Three different protocols are employed in this series of experiments. They are as follows:

Protocol 1.

Rationale: The inability of reperfusion therapy to increase contractile function distal to a chronic coronary artery stenosis is due to the lack of functioning cardiac myocytes and not to the ability to increase blood flow to the ischemic zone. The goal of this experiment is to determine if the injection of MPCs into the heart results in the formation of functional cardiac myocytes and results in amelioration of the ischemia due to chronic coronary stenosis.

Specific methods: The dog is trained to lie on the laboratory table and then echocardiography is performed with special attention to the anterior wall. Dogs are instrumented for the measurement of global and segmental cardiac function and with a flow transducer, hydraulic occluder and critical stenosis on the distal LAD. At surgery the stenosis is adjusted to eliminate the reactive hyperemia following a 15 second coronary artery occlusion (a critical stenosis). The left atrial appendage is harvested from which MPCs are isolated and propagated. The chest is closed in layers and the dog allowed to recover. Ten days after surgery hemodynamics are recorded, the reactive hyperemia examined, and echocardiography performed. This is repeated each week for 2-4 weeks (until the autologous canine stem cells proliferate, estimates are that $10 \times 10^6$/ml cells per animal are used). Once sufficient cells are available, hemodynamics (non radioactive microspheres injected through the left atrium to measure collateral flow) are recorded and then the dog anesthetized with sodium pentobarbital. The dog is taken to the fluoroscopy laboratory and the LAD catheterized to visualize the collateral circulation and to inject MPCs using a specially designed balloon-needle catheter (414). The needle is advanced from the catheter and injections of 250 µl of the MPC cell suspension is given 2-5 times. In some of the dogs, the cell suspension is mixed with contrast media (414) to visualize the sites of injection. The catheter is removed and the dog allowed to recover. The dog is studied each week for 4 weeks and microspheres injected to measure collateral flow. At that time the cardiac catheterization is repeated to visualize collateral blood flow and one half the dogs is anesthetized and the heart perfusion fixed. In the other half, tissue is collected for in vitro studies of microvessel reactivity.

The results of these experiments are expected to show that the injection of MPCs results in a partially developed collateral circulation (fluoroscope) growth of GFP containing cardiac myocytes and few GFP labeled blood vessels. There may be minimal increased deposition of microspheres in the ischemic zone distal to the stenosis. There may be a relationship between increased cardiac function and the site and number of GFP staining MPCs.

Figure 21:
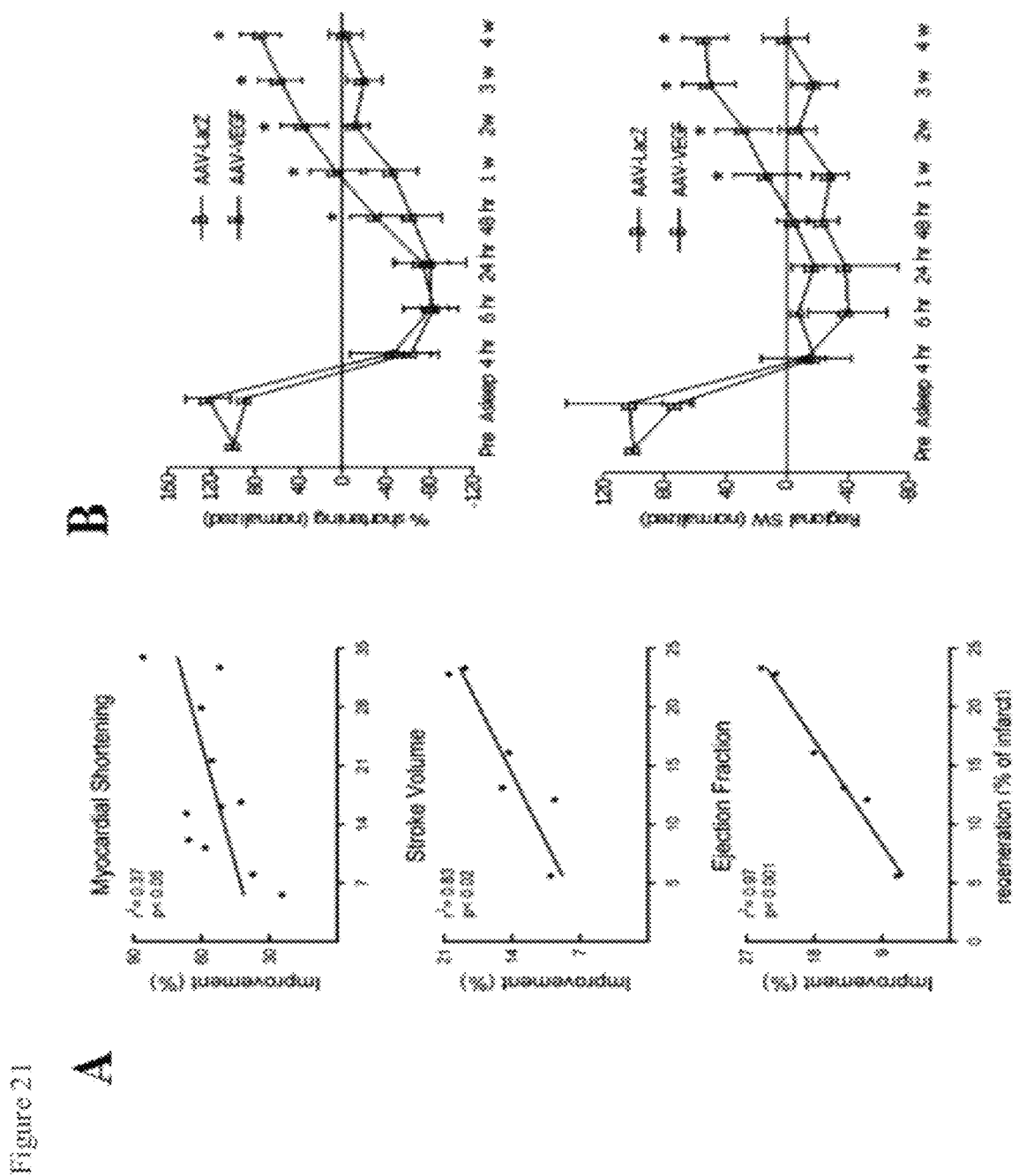
FIG. 21. A. Injection of HGF or IGF results in an increase in contractile function in the ischemic zone following 4 hours of total occlusion of the LAD (301). In addition, evidence of newly generated cardiac myocytes and an increase in ejection fraction, stroke volume (figure from Linke et al (301)) and shortening (panel A) that was proportional to the regeneration of the myocardium was observed. B. In another set of experiments (panel B) designed to use an adeno-associated virus containing VEGF to grow new blood vessels in the area of an infarction (small LAD infarct as proposed), an increase in segment function and segment work in segments that were either paradoxical to begin with or in those that had reduced shortening (310) was observed. This was associated with an increase in the number of cardiomyocytcs in the area of the infarct.

We have previously published (301) that injection of HGF or IGF results in an increase in contractile function in the ischemic zone following 4 hours of total occlusion of the LAD. In addition, we found evidence of newly generated cardiac myocytes and an increase in ejection fraction, stroke volume (301) and shortening (right FIG. 21, panel A) that was proportional to the regeneration of the myocardium.

In another set of experiments (FIG. 21, panel B) designed to use an adeno-associated virus containing VEGF to grow new blood vessels in the area of an infarction (small LAD infarct as proposed), we also found an increase in segment function and segment work in segments that were either paradoxical to begin with or in those that had reduced shortening (310). This was associated with an increase in the number of cardiomyocytes in the area of the infarct.

Protocol 2.

Rationale: It is not the ability to increase blood flow during reperfusion injury to the border zone of a small infarct that limits recovery, rather it is the lack of functioning myocytes. This is important since a small infarct may enlarge or extend with time if wall stress increases resulting in additional ischemic damage. The goal of this study is to determine if the injections of MPCs into the border and ischemic zone of a distal (small infarct) LAD occlusion results in increased blood flow and contractile function. These studies use a small infarction so that complications of heart failure are not present.

Specific methods: Surgery is performed using general anesthesia and sterile technique for the measurement of cardiac function (including segment function) and with an occluder and flow transducer on the LAD. The left atrial appendage is harvested for the collection of MPCs. The dog is allowed to recover for 10 days. Hemodynamics studies and echocardiography are performed and then the dog anesthetized, the distal LAD permanently occluded and the dog allowed 2-4 weeks to recover. Hemodynamic recordings are made after 2-4 weeks, and then under general anesthesia, cardiac catheterization performed, and catheter injections of MPCs (250 µl) using an echo-guided spinal needle or Mercator are made into the middle of the infarct and then into the border zone (3-5 injections). The dog is allowed to recover and then hemodynamic recordings made each week for 4 weeks. At that time microspheres are injected, the dogs are anesthetized for cardiac catheterization, and the heart perfusion fixed or collected for in vitro studies of coronary microvessels.

The results are expected to show an increase in local contraction in the border zone of the infarct. There may be no increase in microsphere measured blood flow to the border zone of the infarct but a demonstable increase in segment function (local contraction). It is also expected that there will be evidence of GFP containing MPCs.

Protocol 3.

Rationale: Myocardial infarction in man is often associated with the development of heart failure due to reduced inotropic state (myocyte loss). Furthermore, once a large infarct is established and heart failure evident, the heart failure progresses due to increase wall stress and subsequent remodeling. There are no current therapies which are targeted to the sequence of events leading to the progression of ischemic heart failure. The use of MPCs would be a unique focused approach to restoring contractile function to a large ischemic area perfused by the LAD. The goal of these experiments is to determine the effectiveness of injection of MPCs as a therapy in the presence of a large established infarction.

Specific methods: In these studies we create a large infarct, sufficient to reduce ejection fraction acutely and chronically by occluding the proximal LAD. Dogs are trained to lie on the laboratory table and echocardiography performed. Dogs are instrumented for the measurement of cardiac function and segment function in the potentially ischemic zone. A flow transducer and hydraulic occluder are placed on the proximal LAD just distal to the first diagonal branch. The left atrial appendage is harvested. The dog is allowed to recover. After recovery and echocardiography, microspheres are injected to measure blood flow and then the dog anesthetized for cardiac catheterization and induction of a permanent occlusion of the proximal LAD. The dog is allowed to recover and the size of the infarct determined by echo, following a second microsphere injection and hemodynamic measures. After 2-4 weeks, the dog is anesthetized, cardiac catheterization performed and using an echo guided spinal needle or Mercator catheter, MPCs are injected into the middle of the infarct and around the border zone. The dog is allowed 2-4 weeks recovery during which hemodynamics and echocardiography are performed.

There may be some increase in GFP-MPCs and perhaps some increase in cardiac function proportional to the increase in MPCs. There may be little increase in blood flow using microspheres or contrast media.

Example 6

Implanted VPCs and MPCs Generate a Biological Bypass and Functionally Competent Myocardium in the Presence of a Stenotic or Occluded Coronary Artery To address the use of strategies to recruit stem cells into the ischemic dog heart, we have performed two studies in dogs with anterior wall infarction following permanent occlusion of the LAD coronary artery. In the first study (301), 6 hours after permanent occlusion, a time point during which there is no recovery of function during reperfusion (347, 348), through an echo guided spinal needle we injected a combination of hepatocyte growth factor (HGF) and insulin like growth factor (IGF), based on previous studies (363-365), into the center of the infarct (as determined by paradoxical motion using the echo) and into the border zone (as identified by reduced systolic function on the echo). We then recorded hemodynamics in the conscious dog each week for 4 weeks and harvested the heart to identify newly formed myocytes and blood vessels. In the conscious dog, injection of IGF and HGF caused recovery in contractile function in both the center of the infarct and in the border zone. This was proportional to the number of newly formed cardiac myocytes and blood vessel cells of stem cell origin. Importantly these cells were derived from adult resident cardiac stem cells based on cell specific markers. Of some significance is the fact that we found increased numbers of both blood vessels and newly formed myocytes leading to the speculation that both cell types are needed to re-establish the relationship between coronary blood flow and contractile function.

We performed studies using the same model and injected an adeno-associated virus containing the human VEGF165 gene into the center and border zone 4 hours after permanent occlusion of the LAD coronary artery (310). Again the dogs were studied in the conscious state for 4 weeks before tissues were collected. In those studies, designed to grow blood vessels using VEGF, we found expression of human VEGF in the dog heart and its receptors in the infarct and found recovery of segment function in both the center of the infarct and in the border zone. Importantly, we also found cardiomyocytes of stem cell origin. Thus using two different strategies in the same model we found recovery of function associated with new cardiomyocytes and new blood vessels again supporting the concept that re-establishment of the flow/function relationship is required for a new therapy to be effective. Importantly, Bearzi et al. (304) also found both newly formed blood vessels and cardiomyocytes in the mouse heart suggesting that development of an integrated myocardium is required to restore function in the ischemic heart.

Three studies using swine as a model for altered cardiac function and stem cell repair during ischemia have been published. The first by Liu et al. (366) examined the effects of autologous bone marrow stem cell administration via a jell patch placed on the ischemic area 60 minutes after release of a coronary artery occlusion. The acute application of stem cell therapy resulted in both neovascularization and new myocyte formation and proliferation. Together, approximately 3 weeks after infarction there was a substantial increase in systolic wall thickening, approximately 40%, and of neovascularization near the patch, including evidence of both coronary arteries and capillaries. These studies using autologous bone marrow stem cells acutely after infarction, support our conclusion that it is best to remodel the heart creating both new blood vessels and myocytes. The same authors (367) recently performed studies designed to examine the effect of allogeneic bone marrow stem cells administered at the time of infarction in the pig. That study indicated an increase in vascular density in treated animals 4 weeks after infarction, however, they also concluded that the contractile effect, decreasing ejection fraction from 55 to 30% with a return to 41% in the treated group, was not due to new myocytes but rather to "patchy spared myocytes." Another study by Suzuki et al. (368) puzzles over the lack of new blood vessel formation and a flow/function relationship in hibernating myocardium transfected with FGF-5 (fibroblast growth factor given in an adenovirus). In that study, there was an increase in shortening in the hibernating myocardium from 2.4 to 4.6 mm 14 days after administration of FGF and only a small increase in blood flow. Furthermore, the authors discuss the possibility that the lack of new blood vessel growth may limit the functional recovery of the heart, again pointing out that the proper coupling of flow and function may result in development of optimum therapies. Therefore strategies which produce both new myocytes and a corresponding circulation may be most efficacious in the treatment and consequences of myocardial ischemia.

The objective of the experiments described in this Example is to determine whether in the presence of a stenotic or occluded coronary artery catheter-delivered or locally injected VPCs and MPCs generate a biological bypass and functionally competent myocardium, which together restore blood flow and regional ventricular function.

Three different protocols are employed in this series of experiments. They are as follows:

Protocol 1.

Rationale: The myocardium normally functions with a specific ratio of blood vessels to myocytes and the loss of that relationship in the process of myocardial ischemia is partially responsible for cardiac contractile dysfunction. The reestablishment of the optimum ratio of cardiac myocytes and blood vessels is most effective in restoring cardiac contractile function. The goal of this experiment is to determine if the injection of both MPCs and VPCs into the heart results in the formation of functional cardiac myocytes and blood vessels and results in salvage of the ischemia due to chronic coronary stenosis.

Specific methods: The dog is trained to lie on the laboratory table and then echocardiography is performed with special attention to the anterior wall. Dogs are instrumented for the measurement of cardiac function and with a flow transducer, hydraulic occluder and critical stenosis on the distal LAD. At surgery, the stenosis is adjusted to eliminate the reactive hyperemia following a 15 second coronary artery occlusion (a critical stenosis). The left atrial appendage is harvested from which both MPCs and VPCs are isolated and propagated. The chest is closed in layers and the dog is allowed to recover. Ten days after surgery hemodynamics are recorded, the reactive hyperemia examined and echocardiography performed. This is repeated each week for 2-4 weeks (until the autologous canine stem proliferate, estimates are that $2 \times 10^6$ cells per ml per animal are used, of combination of VPCs and MPCs). Once sufficient cells are available, hemodynamics (non radioactive microspheres are injected through the left atrium to measure collateral flow) are recorded and then the dog anesthetized with sodium pentobarbital. The dog is taken to the fluoroscopy laboratory and the LAD catheterized to visualize the collateral circulation and then for use of a specially designed balloon-needle catheter (414). The needle is advanced from the catheter and injections of 250 µl of the mixture of VPC and MPCs cell suspension is given 2-5 times each. In some of the dogs the cell suspension is mixed with contrast media (Mercator paper) to visualize the sites of injection. The catheter is removed and the dog allowed to recover. The dog is studied each week for 4 weeks and microspheres injected to measure blood flow. On the last day, under general anesthesia cardiac catheterization is performed to visualize the collateral circulation. At that time one half the dogs are anesthetized and the heart perfusion fixed. In the other half, tissue is collected for in vitro studies of microvessel reactivity.

The injection of the mixture of MPCs and VPC may result in growth of GFP containing myocytes and blood vessels, increased deposition of microspheres in the ischemic zone distal to the stenosis, and importantly increased regional contractile function. There may be a large collateral network by fluoroscopy. In isolated perfused coronary microvessels there may be increased flow induced dilation (indicating functional endothelium) and increased agonist induced dilation (indicating enhanced smooth muscle and endothelial function). There may be a relationship between dilation in vitro and the site and amount of GFP staining in microvessels. There may be an increase in contractile function in the ischemic zone that is greater than can be accounted for by the increase in blood flow, indicating the important role played by MPCs in recovery of contractile function in the ischemic heart. It is possible that the ratio of enhanced blood flow (VPCs) and enhanced contraction (MPCs) is critical to the recovery of the ischemic heart and that adjusting the number of each VPC and MPC (an optimal ratio) may have to be performed to optimize salvage for each particular condition or subject. It may be possible to inject VPCs to grow blood vessels first and then MPCs to grow myocytes once the circulation has developed sufficiently to support MPC differentiation, growth and function.

Protocol 2.

Rationale: The lack of restoration of blood flow to the border zone of the ischemic heart may limit the survival of myocytes that have survived the initial ischemia. On the other hand, the reduced number of myocytes may doom the ischemic area due to the reduction in inotropic state and cardiac contractile function. Thus, solving only one of these two problems, reduced blood flow or reduced myocyte mass, is not sufficient to restore cardiac function. The goal of this study is to determine if the injections of both MPCs and VPCs into the border and ischemic zone of a distal (small infarct) LAD occlusion results in increased blood flow and contractile function. These studies use a small infarction so that the complications of heart failure are not present.

Specific methods: Surgery is performed using general anesthesia and sterile technique for the measurement of cardiac function (including segment function) and with an occluder and flow transducer on the LAD. The left atrial appendage is harvested for the collection of VPCs and MPCs. The dog is allowed to recover for 10 days. Hemodynamic studies and echocardiography are performed and then the dog anesthetized, the distal LAD permanently occluded and the dog allowed 2-4 weeks to recover. After 2-4 weeks, under general anesthesia the LAD is catheterized to visualize the circulation to the infarct and then using an echo-guided spinal needle or Mercator catheter injections of MPCs and VPCs (250 each) are made into the middle of the infarct and then into the border zone (3-5 injections). The dog is allowed to recover and then hemodynamic recordings made each week for 4 weeks. For the last experiment, microspheres are injected and the dog anesthetized for catheterization of the LAD and contrast injection. At that time the heart is perfusion fixed or tissues collected for in vitro studies of coronary microvessels.

There may be an increase in microsphere measured blood flow and delivery of contrast (catheterization) to the border zone of the infarct. There may be evidence of GFP containing cardiac myocytes and blood vessels and in vitro these will have enhanced flow and agonist induced dilation. There may be a substantial increase in local segment function due to the growth and proliferation of MPCs. It may be beneficial to alter the number of MPCs and VPCs to optimize the ratio that governs flow and function to increase segment function and to fully restore contractile function of the anterior wall. In addition it may be possible to inject VPCs first to support the differentiation, growth and function of MPCs once the coronary circulation has developed.

Protocol 3

Rationale: Myocardial infarction in man is often associated with the development of heart failure due to reduced inotropic state and for instance large reductions in ejection fraction. Furthermore, once a large infarct is established with loss of both myocytes and blood vessels and heart failure evident, the heart failure progresses due to increase wall stress and subsequent remodeling. There are no current therapies which are targeted to the sequence of events leading to the progression of ischemic heart failure. The use of both MPCs and VPCs would be a unique combinatorial approach to restoring blood flow and contractile function to a large ischemic area perfused by the LAD. The goal of these experiments is to determine the effectiveness of injection of both MPCs and VPCs as a therapy in the presence of a large established infarction.

Specific methods: In these studies, we create a large infarct, sufficient to reduce ejection fraction acutely and chronically by occluding the proximal LAD. Dogs are trained to lie on the laboratory table and echocardiography performed. Dogs are instrumented for the measurement of cardiac function and segment function in the potentially ischemic zone. A flow transducer and hydraulic occluder are placed on the proximal LAD just distal to the first diagonal branch. The left atrial appendage is harvested. The dog is allowed to recover. After recovery and echocardiography, microspheres are injected to measure blood flow and then the dog anesthetized for cardiac catheterization to visualize the circulation and for permanent occlusion of the proximal LAD. The dog is allowed to recover and the size of the infarct determined by echo, following microsphere injection and hemodynamic measures. After 2-4 weeks the dog is anesthetized, the cardiac catheterization repeated and using an echo guided spinal needle of Mercator catheter, MPCs and VPCs injected into the middle of the infarct (initially at the same time and at an initial ratio of 1/1) and around the border zone. The dog is allowed 2-4 weeks during which hemodynamics and echocardiography are performed. On the final day, the dog is anesthetized and cardiac catheterization performed to visualize the circulation.

There may be a substantial increase in GFP labeled blood vessels and myocytes, in microsphere measured blood flow to the ischemic region, an increase in visualized blood flow by contrast injection, and a marked increase in cardiac function which is greater than would be predicted by the increase in blood flow alone supporting the important role of MPCs. To achieve an ejection fraction similar to that before infarction, the ratio of the injected MPCs/VPCs may be adjusted or optimized. Alternatively or additionally, the timing of injection of the VPCs and MPCs may be adjusted.

Having thus described in detail preferred embodiments of the present invention, it is to be understood that the invention defined by the appended claims is not to be limited by par- ticular details set forth in the above description as many apparent variations thereof are possible without departing from the spirit or scope thereof.

Those skilled in the art will recognize, or be able to ascertain using no more than routine experimentation, many equivalents to the specific embodiments of the invention described herein. Such equivalents are intended to be encompassed by the following claims.

References

1. Fishman M C, Chien K R: Fashioning the vertebrate heart: earliest embryonic decisions. Development. 124:2099-2117, 1997.
2. Mikawa T: Cardiac lineages. In: RP Harvey, N Rosenthal, eds: Heart Development. Academic Press, San Diego, pp. 19-33, 1999.
3. Srivastava D, Olson E N: A genetic blueprint for cardiac development. Nature. 407: 221-226, 2000.
4. Bruneau B G: Transcriptional regulation of vertebrate cardiac morphogenesis. Circ Res. 90:509-519, 2002.
5. Harvey R P: Patterning the vertebrate heart. Nat Rev Genet. 3:544-556, 2002.
6. Mikawa T: Early embryonic vascular development. Cardiovasc Res. 31:E34-E45, 1996.
7. Reese D E, Mikawa T, Bader D M: Development of the coronary vessel system. Circ Res. 91:761-768, 2002.
8. Olivey H E, Compton L A, Barnett J V: Coronary vessel development: the epicardium delivers. Trends Cardiovasc Med. 14:247-251, 2004.
9. Mikawa T, Fischman D A: Retroviral analysis of cardiac morphogenesis: discontinuous formation of coronary vessels. Proc Natl Acad Sci USA. 89:9504-9508, 1992.
10. Mikawa T, Gourdie R G: Pericardial mesoderm generates a population of coronary smooth muscle cells migrating into the heart along with ingrowth of the epicardial organ. Dev Biol. 174:221-232, 1996.
11. Wessels A, Perez-Pomares J M: The epicardium and epicardially derived cells (EPDCs) as cardiac stem cells. Anat Rec A Discov Mol Cell Evol Biol. 276:43-57, 2004.
12. Anversa P, Leri A, Beltrami C A, Guerra S, Kajstura J: Myocyte death and growth in the failing heart. Lab Invest. 78:767-786, 1998.
13. Beltrami A P, Urbanek K, Kajstura J, Yao S-M, Finato N, Bussani R, Nadal-Ginard B, Silvestri F, Leri A, Beltrami C A, Anversa P: Evidence that human cardiac myocytes divide after myocardial infarction. N Engl J. Med. 344: 1750-1757, 2001.
14. Quaini F, Urbanek K, Beltrami A P, Finato N, Beltrami C A, Nadal-Ginard B, Kajstura J, Leri A, Anversa P: Chimerism of the transplanted heart. N Engl J. Med. 346:5-15, 2002.
15. Urbanek K, Quaini F, Tasca G, Torella D, Castaldo C, Nadal-Ginard B, Leri A, Kajstura J, Quaini E, Anversa P: Intense myocyte formation from cardiac stem cells in human cardiac hypertrophy. Proc Natl Acad Sci USA. 100: 10440-10445, 2003.
16. Urbanek K, Torella D, Sheikh F, De Angelis A, Nurzynska D, Silvestri F, Beltrami C A, Bussani R, Beltrami A P, Quaini F, Bolli R, Leri A, Kajstura J, Anversa P: Myocardial regeneration by activation of multipotent cardiac stem cells in ischemic heart failure. Proc Natl Acad Sci USA. 102:8692-8697, 2005.
17. Anversa P, Leri A, Rota M, Hosoda T, Bearzi C, Urbanek K, Kajstura J, Bolli R: Concise review: stem cells, myocardial regeneration, and methodological artifacts. Stem Cells. 25:589-601, 2007.
18. Leri A, Kajstura J, Anversa P: Cardiac stem cells and mechanisms of myocardial regeneration. Physiol Rev. 85:1373-1416, 2005.
19. Anversa P, Kajstura J, Leri A, Bolli R: Life and death of cardiac stem cells: a paradigm shift in cardiac biology. Circulation. 113:1451-1463, 2006.
20. Anversa P, Leri A, Kajstura J: Cardiac regeneration. J Am Coll Cardiol. 47:1769-1776, 2006.
21. Beltrami A P, Barlucchi L, Torella D, Baker M, Limana F, Chimenti S, Kasahara H, Rota M, Musso E, Urbanek K. Leri A, Kajstura J, Nadal-Ginard B, Anversa P: Adult cardiac stem cells are multipotent and support myocardial regeneration. Cell. 114:763-776, 2003.
22. Linke A, Muller P, Nurzynska D, Casarsa C, Torella D, Nascimbenc A, Castaldo C, Cascapera S, Bohm M, Quaini F, Urbanek K, Leri A, Hintze T H, Kajstura J, Anversa P: Stem cells in the dog heart are self-renewing, clonogenic, and multipotent and regenerate infarcted myocardium, improving cardiac function. Proc Natl Acad Sci USA. 102: 8966-8971, 2005.
23. Urbanek K, Rota M, Cascapera S, Bearzi C, Nascimbene A, De Angelis A, Hosoda T, Chimenti S, Baker M, Limana F, Nurzynska D, Torella D, Rotatori F, Rastaldo R, Musso E, Quaini F, Leri A, Kajstura J, Anversa P: Cardiac stem cells possess growth factor-receptor systems that after activation regenerate the infarcted myocardium, improving ventricular function and long-term survival. Circ Res. 97:663-673, 2005.
24. Hierlihy A M. Seale P, Lobe C G, Rudnicki M A, Megeney L A: The post-natal heart contains a myocardial stem cell population. FEBS Lett. 530:239-243, 2002.
25. Oh H, Bradfute S B, Gallardo T D, Nakamura T, Gaussin V, Mishina Y, Pocius J, Michael L H, Behringer R R, Garry D J, Schneider M D: Cardiac progenitor cells from adult myocardium: horning, differentiation, and fusion after infarction. Proc Natl Acad Sci USA. 100:12313-12318, 2003.
26. Matsuura K, Nagai T. Nishigaki N, Oyama T, Nishi J, Wada H, Sano M, Toko H, Akazawa H, Sato H, Nakaya H, Kasanuki H, Komuro I: Adult cardiac Sca-1-positive cells differentiate into beating cardiomyocytes. J Biol Chem. 279:11384-11391, 2004.
27. Martin C M, Meeson A P, Robertson S M, Hawke T J, Richardson J A, Bates S, Goetsch S C, Gallardo T D, Garry D J: Persistent expression of the ATP-binding cassette transporter, Abcg2, identifies cardiac SP cells in the developing and adult heart. Dev Biol. 265:262-275, 2004.
28. Messina E, De Angelis L, Frati G, Morrone S, Chimenti S, Fiordaliso F, Salio M, Battaglia M. Latronico M V G, Coletta M. Vivarelli E, Frati L, Cossu G, Giacomello A: Isolation and expansion of adult cardiac stem cells from human and murine heart. Circ Res. 95:911-921, 2004.
29. Pfister O, Mouquet F, Jain M, Summer R, Helmes M, Fine A, Colucci W S, Liao R: CD31− but not CD31+ cardiac side populations cells exhibit functional cardiomyogenic differentiation. Circ Res. 97:52-61, 2005.
30. Laugwitz K L, Moretti A, Lam J, Gruber P, Chen Y, Woodard S, Lin L Z, Cai C L, Lu M M, Reth M, Platoshyn O, Yuan J X, Evans S, Chien K R: Postnatal isl1+ cardioblasts enter fully differentiated cardiomyocyte lineages. Nature. 433:585-587, 2005.
31. Rosenblatt-Velin N, Lepore M G, Cartoni C, Beermann F, Pedrazzini T: FGF-2 controls the differentiation of resident cardiac precursors into functional cardiomyocytes. I Clin Invest. 115:1724-1733, 2005.
32. Tomita Y, Matsumura K, Wakamatsu Y, Matsuzaki Y, Shibuya I, Kawaguchi H, Ieda M, Kanakubo S. Shinmazaki T, Ogawa S, Osumi N, Okano H, Fukuda K: Cardiac neural crest cells contribute to the dormant multipotent stem cell in the mammalian heart. J Cell Biol. 170: 1135-1146, 2005.
33. Bearzi C, Rota M, Hosoda T, Tillmanns J, Nascimbene A, De Angelis A, Yasuzawa-Amano S, Trofimova I, Siggins R W, Cascapera S, Beltrami A P, Zias E, Quaini F, Urbanek K, Michler R E, Bolli R, Kajstura J, Leri A, Anversa P: Human cardiac stem cells. Proc Natl Acad Sci USA. 104:14068-14073, 2007.
34. Carmeliet P: Angiogenesis in life, disease and medicine. Nature. 438:932-936, 2005.
35. Carmeliet P, Jain R K: Angiogenesis in cancer and other diseases. Nature. 407:249-257, 2000.
36. Carmeliet P: Angiogenesis in health and disease. Nat Med. 9:653-660, 2003.
37. Asahara T, Murohara T, Sullivan A, Silver M, van der Zee R, Li T, Witzenbichler B, Schatteman G, Isner J M: Isolation of putative progenitor endothelial cells for angiogenesis. Science. 275:964-967, 1997.
38. Aicher A, Heeschen C, Mildner-Rihm C, Urbich C, Ihling C, Technau-Ihling K, Zeiher A M, Dimmeler S: Essential role of endothelial nitric oxide synthase for mobilization of stem and progenitor cells. Nat Med. 9:1370-1376, 2003.
39. Urbich C, Dimmeler S: Endothelial progenitor cells: characterization and role in vascular biology. Circ Res. 95: 343-353, 2004.
40. Asahara T. Kawamoto A: Endothelial progenitor cells for postnatal vasculogenesis. Am J. Physiol. 287:C572-579, 2004.
41. Carmeliet P: Mechanisms of angiogenesis and arteriogenesis. Nat Med. 6:389-395, 2000.
42. Hirschi K K, Goodell M A: Hematopoietic, vascular and cardiac fates of bone marrow-derived stem cells. Gene Then 9:648-652, 2002.
43. Deb A, Skelding K A, Wang S, Reeder M, Simper D, Caplice N M: Integrin profile and in vivo homing of human smooth muscle progenitor cells. Circulation. 110:2673-2677, 2004.
44. Hu Y, Zhang Z, Torsney E, Afzal A R, Davison F, Metzler B, Xu Q: Abundant progenitor cells in the adventitia contribute to atherosclerosis of vein grafts in ApoE-deficient mice. J Clin Invest. 113:1258-1265, 2004.
45. Mayr U, Mayr M, Yin X, Begum S, Tarelli E, Wait R, Xu Q: Proteomic dataset of mouse aortic smooth muscle cells. Proteomics. 5:4546-4557, 2005.
46. Torsney E, Mandal K, Halliday A, Jahangiri M, Xu Q: Characterisation of progenitor cells in human atherosclerotic vessels. Atherosclerosis. 191:259-264, 2007.
47. Mandal K, Jahangiri M, Xu Q: Progenitor cells and vascular repair. In *Cardiovascular Regeneration and Stem Cell Therapy*. Eds. A. Leri, P. Anversa, W. H. Frishman, Blackwell Futura 2007, Malden, Mass., pp. 57-66.
48. Minasi M G, Riminucci M, De Angelis L, Borello U, Berarducci B, Innocenzi A, Caprioli A, Sirarella D, Baiocchi M, De Maria R, Boratto R, Jaffredo T, Broccoli V, Bianco P, Cossu G: The meso-angioblast: a multipotent, self-renewing cell that originates from the dorsal aorta and differentiates into most mesodermal tissues. Development. 129:2773-2783, 2002.
49. Sampaolesi M, Blot S, D'Antona G, Granger N, Tonlorenzi R, Innocenzi A, Mognol P, Thibaud J L, Galvez B G, Barthelemy I, Perani L, Mantero S, Guttinger M, Pansarasa O, Rinaldi C, Cusella De Angelis M G, Torrente Y, Bordignon C, Bottinelli R. Cossu G: Mesoangioblast stem cells ameliorate muscle function in dystrophic dogs. Nature. 444:574-579, 2006.
50. Dellavalle A, Sampaolesi M, Tonlorenzi R. Tagliafico E, Sacchetti B, Perani L, Innocenzi A, Galvez B G, Messina G, Morosetti R, Lis S, Belicchi M, Peretti G, Chamberlain J S, Wright W E, Torrente Y, Ferrari S, Bianco P, Cossu G: Pericytes of human skeletal muscle are myogenic precursors distinct from satellite cells. Nat Cell Biol. 9: 255-267, 2007.
51. Zengin E, Chalajour F, Gehling U M, Ito W D, Treede H, Lauke H, Weil J, Reichenspurner H, Kilic N, Ergun S: Vascular wall resident progenitor cells: a source for postnatal vasculogenesis. Development. 133:1543-1551, 2006.
52. Aicher A, Rentsch M, Sasaki K, Ellwart J W, Fandrich F, Siebert R, Cooke J P, Dimmeler S, Heeschen C: Nonbone marrow-derived circulating progenitor cells contribute to postnatal neovascularization following tissue ischemia. Circ Res. 100:581-589, 2007.
53. Urbanek K, Cesselli D, Rota M, Nascimbene A, De Angelis A, Hosoda T, Bearzi C, Boni A, Bolli R, Kajstura J, Anversa P, Leri A: Stem cell niches in the adult mouse heart. Proc Natl Acad Sci USA. 103:9226-9231, 2006.
54. Coultas L, Chawengsaksophak K. Rossant J: Endothelial cells and VEGF in vascular development. Nature. 438:937-945, 2005.
55. Huber T L, Kouskoff V, Fehling H J, Palls J, Keller G: Haemangioblast commitment is initiated in the primitive streak of the mouse embryo. Nature. 432:625-630, 2004.
56. Shalaby F, Ho J, Stanford W L, Fischer K D, Schuh A C, Schwartz L, Bernstein A, Rossant J: A requirement for Flk1 in primitive and definitive hematopoiesis and vasculogenesis. Cell. 89:981-990, 1997.
57. Shalaby F, Rossant J, Yamaguchi T P, Gertsenstein M, Wu X F, Breitman M L, Schuh A C: Failure of blood-island formation and vasculogenesis in Flk-1-deficient mice. Nature. 376:62-66, 1995.
58. Yamashita J, Itoh H, Hirashima M, Ogawa M, Nishikawa S, Yurugi T. Naito M. Nakao K, Nishikawa S: Flk1-positive cells derived from embryonic stem cells serve as vascular progenitors. Nature. 408:92-96, 2000.
59. Kaltman S J, Huber T L, Keller G M: Multipotent flk-1+ cardiovascular progenitor cells give rise to the cardiomyocyte, endothelial, and vascular smooth muscle lineages. Dev Cell. 11:723-732, 2006.
60. Wu S M, Fujiwara Y, Cibulsky S M, Clapham D E, Lien C L, Schultheiss T M, Orkin S H: Developmental origin of a bipotential myocardial and smooth muscle cell precursor in the mammalian heart. Cell. 127:1137-1150, 2006.
61. Moretti A, Caron L, Nakano A, Lam J T, Bernshausen A, Chen Y, Qyang Y, Bu L, Sasaki M, Martin-Puig S, Sun Y, Evans S M, Laugwitz K L, Chien K R: Multipotent embryonic isl1+ progenitor cells lead to cardiac, smooth muscle, and endothelial cell diversification. Cell. 127:1151-1165, 2006.
62. Kataoka H, Takakura N, Nishikawa S, Tsuchida K, Kodama H, Kunisada I. Risau W, Kita I, Nishikawa I S: Expressions of PDGF receptor alpha, c-Kit and Flk1 genes clustering in mouse chromosome 5 define distinct subsets of nascent mesodermal cells. Dev Growth Differ. 39:729-740, 1997.
63. Nishikawa S I, Nishikawa S, Hirashima M, Matsuyoshi N, Kodama H: Progressive lineage analysis by cell sorting and culture identifies FLK 1+VE-cadherin+ cells at a diverging point of endothelial and hemopoietic lineages. Development. 125:1747-1757, 1998.
64. Bertrand J Y, Giroux S, Golub R, Klaine M, Jalil A, Bouconet L, Godin I, Cumano A: Characterization of puri- 64. fied intraembryonic hematopoietic stem cells as a tool to define their site of origin. Proc Natl Acad Sci USA. 102: 134-139, 2005.
65. Samokhvalov I M, Samokhvalova N I, Nishikawa S: Cell tracing shows the contribution of the yolk sac to adult haematopoiesis. Nature. 446:1056-1061, 2007.
66. Orlic D, Kajstura J, Chimenti S, Jakoniuk I, Anderson S M, Li B, Pickel J, McKay R, Nadal-Ginard B, Bodine D M, Leri A, Anversa P: Bone marrow cells regenerate infarcted myocardium. Nature. 410:701-705, 2001.
67. Orlic D, Kajstura J, Chimenti S. Limana F, Jakoniuk I, Quaini F, Nadal-Ginard B, Bodine D M, Leri A, Anversa P: Mobilized bone marrow cells repair the infarcted heart improving function and survival. Proc Natl Acad Sci USA. 98:10344-10349, 2001.
68. Kajstura J, Rota M, Whang B, Cascapera S, Hosoda T, Bearzi C, Nurzynska D. Kasahara H, Zias E. Bonafe' M, Nadal-Ginard B, Torella D. Nascimbene A, Quaini F, Urbanek K, Leri A, Anversa P: Bone marrow cells differentiate in cardiac cell lineages after infarction independently of cell fusion. Circ Res. 96:127-137, 2005.
69. Murasawa S, Kawamoto A, Horii M, Nakamori S, Asahara T: Niche-dependent translineage commitment of endothelial progenitor cells, not cell fusion in general, into myocardial lineage cells. Arterioscler Thromb Vase Biol. 25:1388-1394, 2005.
70. Koyanagi M, Brandes R P, Haendeler J, Zeiher A M, Dimmeler 5: Cell-to-cell connection of endothelial progenitor cells with cardiac myocytes by nanotubes: a novel mechanism for cell fate changes? Circ Res. 96:1039-1041, 2005.
71. Jan Y N, Jan L Y: Asymmetric cell division. Nature. 392:775-778, 1998.
72. Lu B, Jan L, Jan Y N: Control of cell divisions in the nervous system: symmetry and asymmetry. Annu Rev Neurosci. 23:531-556, 2000.
73. Noctor S C, Martinez-Cerdeno V, Ivic L, Kriegstein A R: Cortical neurons arise in symmetric and asymmetric division zones and migrate through specific phases. Nat Neurosci. 7:136-144, 2004.
74. Roegiers F, Jan Y N: Asymmetric cell division. Curr Opin Cell Biol. 16:195-205, 2004.
75. Faubert A, Lessard J, Sauvageau G: Are genetic determinants of asymmetric stem cell division active in hematopoietic stem cells? Oncogene. 23:7247-55, 2004.
76. Gotz M, Huttner W B: The cell biology of neurogenesis. Nat Rev Mol Cell Biol. 6: 777-788, 2005.
77. Huttner W B, Kosodo Y: Symmetric versus asymmetric cell division during neurogenesis in the developing vertebrate central nervous system. Curr Opin Cell Biol. 17:648-657, 2005.
78. Lechler T, Fuchs E: Asymmetric cell divisions promote stratification and differentiation of mammalian skin. Nature. 437:275-280, 2005.
79. Clevers H: Stem cells, asymmetric division and cancer. Nat Genet. 37:1027-1028, 2005.
80. Verdi J M, Bashirullah A, Goldhawk D E, Kubu C J, Jamali M, Meakin S O, Lipshitz H D: Distinct human NUMB isoforms regulate differentiation vs. proliferation in the neuronal lineage. Proc Natl Acad Sci USA. 96:10472-10476, 1999.
81. Braun K M, Niemann C, Jensen, U B, Sundberg, J P, Silva-Vargas V, Watt F M: Manipulation of stem cell proliferation and lineage commitment: visualization of label-retaining cells in whole mounts of mouse epidermis. Development. 130:5241-5255, 2003.
82. Tumbar T, Guasch G, Greco V, Blanpain C, Lowry W E, Rendl M, Fuchs E: Defining the epithelial stem cell niche in skin. Science. 303:359-363, 2004.
83. Aaku-Saraste E, Oback B, Hellwig A, Huttner W B: Neuroepithelial cells downregulate their plasma membrane polarity prior to neural tube closure and neurogenesis. Mech Dev. 69:71-81, 1997.
84. Huttner W B, Brand M: Asymmetric division and polarity of neuroepithelial cells. Curr Opin Neurobiol. 7:29-39, 1997.
85. Halfter W, Dong S, Yip Y P, Willem M, Mayer U: A critical function of the pial basement membrane in cortical histogenesis. J Neurosci. 22:6029-6040, 2002.
86. Malicki J: Cell fate decisions and patterning in the vertebrate retina: the importance of timing, asymmetry, polarity and waves. Curr Opin Neurohiol. 14:15-21, 2004.
87. Cowan C R, Hyman A A: Asymmetric cell division in C. elegans: cortical polarity and spindle positioning. Annu Rev Cell Dev Biol. 20:427-453, 2004.
88. Wodarz A: Molecular control of cell polarity and asymmetric cell division in Drosophila neuroblasts. Curr Opin Cell Biol. 17:475-481, 2005.
89. Strome S, Wood W B: Generation of asymmetry and segregation of germ-line granules in early C. elegans embryos. Cell. 35:15-25, 1983.
90. Chenn A, McConnell S K: Cleavage orientation and the asymmetric inheritance of Notch1 immunoreactivity in mammalian neurogenesis. Cell. 82:631-641, 1995.
91. Kaltschmidt J A, Davidson C M, Brown N H, Brand A H: Rotation and asymmetry of the mitotic spindle direct asymmetric cell division in the developing central nervous system. Nat Cell Biol. 2:7-12, 2000.
92. Roegiers F, Younger-Shepherd S, Jan L Y, Jan Y N: Two types of asymmetric divisions in the Drosophila sensory organ precursor cell lineage. Nat Cell Biol. 3:58-67, 2001.
93. Kusch J, Liakopoulos D, Barral Y: Spindle asymmetry: a compass for the cell. Trends Cell Biol. 13:562-569, 2003.
94. Grava S, Schaerer F, Faty M. Philippsen P, Barral Y: Asymmetric recruitment of dynein to spindle poles and microtubules promotes proper spindle orientation in yeast. Dev Cell. 10:425-439, 2006.
95. Shen C P, Jan L Y, Jan Y N: Miranda is required for the asymmetric localization of Prospero during mitosis in Drosophila. Cell. 90:449-458, 1997.
96. Shen C P, Knoblich J A, Chan Y M, Jiang M M, Jan L Y, Jan Y N: Miranda as a multidomain adapter linking apically localized Inscuteable and basally localized Staufen and Prospero during asymmetric cell division in Drosophila. Genes Dev. 12:1837-1846, 1998.
97. Shen Q, Zhong W, Jan Y N, Temple S: Asymmetric Numb distribution is critical for asymmetric cell division of mouse cerebral cortical stem cells and neuroblasts. Development. 129:4843-4853, 2002.
98. Shen Q, Temple S: Creating asymmetric cell divisions by skewing endocytosis. Sci STKE. 162:PE52, 2002.
99. Li H S, Wang D, Shen Q, Schonemann M D, Gorski J A, Jones K R, Temple S, Jan L Y, Jan Y N: Inactivation of Numb and Numblike in embryonic dorsal forebrain impairs neurogenesis and disrupts cortical morphogenesis. Neuron. 40:1105-1118, 2003.
100. Androutsellis-Theotokis A, Leker R R, Soldner F, Hoeppner D J, Ravin R, Poser S W, Rueger M A, Bae S K, Kittappa R, McKay R D: Notch signaling regulates stem cell numbers in vitro and in vivo. Nature. 442:823-826, 2006.
101. Wang Y, Chan S L, Miele L, Yao P J, Mackes J, Ingram D K, Mattson M P, Furukawa K: Involvement of Notch 101. signaling in hippocampal synaptic plasticity. Proc Natl Acad Sci USA. 101:9458-9462, 2004.
102. Hatakeyama J, Bessho Y, Katoh K, Ookawara S, Fujioka M, Guillemot F, Kageyama R: Hes genes regulate size, shape and histogenesis of the nervous system by control of the timing of neural stem cell differentiation. Development. 131:5539-5550, 2004.
103. Kageyama R, Ohtsuka T, Hatakeyama J, Ohsawa R: Roles of bHLH genes in neural stem cell differentiation. Exp Cell Res. 306:343-348, 2005.
104. Yu F, Kuo C T, Jan Y N: Drosophila neuroblast asymmetric cell division: recent advances and implications for stem cell biology. Neuron. 51:13-20, 2006.
105. Hatakeyama J, Kageyama R: Notch1 expression is spatiotemporally correlated with neurogenesis and negatively regulated by Notch1-independent Hes genes in the developing nervous system. Cereb Cortex. 16 (Suppl. 1):132-137, 2006.
106. Alexson T O, Hitoshi S, Coles B L, Bernstein A, van der Kooy D: Notch signaling is required to maintain all neural stem cell populations—irrespective of spatial or temporal niche. Dev Neurosci. 28:34-48, 2006.
107. Hatakeyama J, Sakamoto S, Kageyama R: Hes1 and Hes5 regulate the development of the cranial and spinal nerve systems. Dev Neurosci. 28:92-101, 2006.
108. Lehar S M, Dooley J, Farr A G, Bevan M J: Notch ligands Delta 1 and Jagged1 transmit distinct signals to T-cell precursors. Blood. 105:1440-1447, 2005.
109. Maillard I, Schwarz B A, Sambandam A, Fang T, Shestova O, Xu L, Bhandoola A, Pear W S: Notch-dependent T-lineage commitment occurs at extrathymic sites following bone marrow. Blood. 107:3511-3519, 2006.
110. Rhyu M S, Jan L Y, Jan Y N: Asymmetric distribution of numb protein during division of the sensory organ precursor cell confers distinct fates to daughter cells. Cell. 76:477-491, 1994.
111. Berdnik D, Torok T, Gonzalez-Gaitan M, and Knoblich J A: The endocytic protein α-adaptin is required for numb-mediated asymmetric cell division in Drosophila. Dev Cell. 3:221-231, 2002.
112. Guo M, Jan L Y, Jan Y N: Control of daughter cell fates during asymmetric division: interaction of Numb and Notch. Neuron. 17:27-41, 1996.
113. Zhu J, Zhang Y, Joe G J, Pompetti R, Emerson S G: NF-Ya activates multiple hematopoietic stem cell (HSC) regulatory genes and promotes HSC self-renewal. Proc Natl Acad Sci USA. 102:11728-11733, 2005.
114. Vercauteren S M, Sutherland H J: Constitutively active Notch4 promotes early human hematopoietic progenitor cell maintenance while inhibiting differentiation and causes lymphoid abnormalities in vivo. Blood. 104:2315-2322, 2004.
115. Gustafsson M V, Zheng X, Pereira T, Gradin K, Jin S, Lundkvist J, Ruas J L, Poellinger L, Lendahl U, Bondesson M: Hypoxia requires notch signaling to maintain the undifferentiated cell state. Dev Cell. 9:575-576, 2005.
116. Boni A, Nascimbene A, Urbanek K, Delucchi F, Gonzalez A, Siggins R, Amano K, Yasuzawa-Amano S, Ojaimi C, Rota M, Hosoda T, Anversa P, Kajstura J, Leri A: Notch1 receptor enhances myocyte differentiation of cardiac progenitor cells and myocardial regeneration after infarction. Submitted, 2007.
117. Smith G H: Label-retaining epithelial cells in mouse mammary gland divide asymmetrically and retain their template DNA strands. Development. 132:681-687, 2004.
118. Karpowicz P, Morshead C, Kam A, Jervis E, Ramunas J, Cheng V, van der Kooy D: Support for the immortal strand hypothesis: neural stem cells partition DNA asymmetrically in vitro. J Cell Biol. 170:721-732, 2005.
119. Merok J R, Lansita J A, Tunstead J R, Sherley J L: Cosegregation of chromosomes containing immortal DNA strands in cells that cycle with asymmetric stem cell kinetics. Cancer Res. 62:6791-6795, 2002.
120. Cairns J: Mutation selection and the natural history of cancer. Nature. 255:197-200, 1975.
121. Kiel M J, He S, Ashkenazi R, Gentry S N, Teta M, Kushner J A, Jackson T L, Morrison S J: Haematopoietic stem cells do not asymmetrically segregate chromosomes or retain BrdU. Nature. Epub ahead of print, 2007.
122. Zhang J, Niu C, Ye L, Huang H, He X, Tong W G, Ross J, Haug J, Johnson T, Feng J Q, Harris S, Wiedemann L M, Mishina Y, Li L: Identification of the haematopoietic stem cell niche and control of the niche size. Nature. 425:836-841, 2003.
123. Armakolas A, Klar A J: Cell type regulates selective segregation of mouse chromosome 7 DNA strands in mitosis. Science. 311:1146-1149, 2006.
124. Watt F M, Hogan B L: Out of Eden: stem cells and their niches. Science 287:1427-1438, 2000.
125. Potten C S, Owen G. Booth D: Intestinal stem cells protect their genome by selective segregation of template DNA strands. J Cell Sci. 115:2381-2388, 2002.
126. Potten C S, Flume W J, Reid P, Cairns J: The segregation of DNA in epithelial stem cells. Cell. 15:899-906, 1978.
127. Welm B E, Tepera S B, Venezia T, Graubert T A, Rosen J M, Goodell M A: Sca-1(pos) cells in the mouse mammary gland represent an enriched progenitor cell population. Dev Biol. 245:42-56, 2002.
128. Shinin V, Gayraud-Morel B, Gomes D, Tajbakhsh S: Asymmetric division and cosegregation of template DNA strands in adult muscle satellite cells. Nat Cell Biol. 8:677-687, 2006.
129. Lansdorp P M: Immortal strands? Give me a break. Cell. 129:1244-1247, 2007.
130. Kawamoto A, Murayama T, Kusano K, Ii M, Tkebuchava T, Shintani S, Iwakura A, Johnson I, von Samson P, Hanley A, Gavin M, Curry C, Silver M, Ma H, Kearney M, Losordo D W: Synergistic effect of bone marrow mobilization and vascular endothelial growth factor-2 gene therapy in myocardial ischemia. Circulation. 110:1398-1405, 2004.
131. Ii M, Nishimua H, Iwakura A, Wecker A, Eaton E, Asahara T, Losordo D W: Endothelial progenitor cells are rapidly recruited to myocardium and mediate protective effect of ischemic preconditioning via "imported" nitric oxide synthase activity. Circulation. 111:1114-1120, 2005.
132. Asai J, Takenaka H, Kusano K F, Ii M, Luedemann C, Curry C, Eaton E, Iwakura A, Tsutsumi Y, I lamada H, Kishimoto S, Thorne T, Kishore R, Losordo D W: Topical sonic hedgehog gene therapy accelerates wound healing in diabetes by enhancing endothelial progenitor cell-mediated microvascular remodeling. Circulation. 113:2413-2424, 2006.
133. Lockhart D J, Dong H, Byrne M C, Follettie M T, Gallo M V, Chee M S, Mittmann M, Wang C, Kobayashi M, Horton H, Brown E L: Expression monitoring by hybridization to high-density oligonucleotide arrays. Nat Biotechnol. 14:1675-1680, 1996.
134. Li C, Wong W H: Model-based analysis of oligonucleotide arrays: expression index computation and outlier detection. Proc Natl Acad Sci USA. 98:31-36, 2001.
135. Bhattacharya B, Miura T, Brandenberger R, Mejido J, Luo Y, Yang A X, Joshi B H, Ginis I, Thies R S, Amit M, Lyons I, Condie B G, Itskovitz-Eldor J, Rao M S, Puri R K:

Gene expression in human embryonic stem cell lines: unique molecular signature. Blood. 103:2956-2964, 2004.
136. Bruno L, Hoffmann R, McBlane F, Brown J, Gupta R, Joshi C, Pearson S, Seidl T, Heyworth C, Enver T: Molecular signatures of self-renewal, differentiation, and lineage choice in multipotential hemopoietic progenitor cells in vitro. Mol Cell Biol. 24:741-756, 2004.
137. Ivanova N B, Dimos J T, Schaniel C, Hackney J A, Moore K A, Lemischka I R: A stem cell molecular signature. Science. 298:601-604, 2002.
138. Ramalho-Santos M S, Yoon Y, Matsuzaki R. Mulligan C, Melton D A: "Stemness" transcriptional profiling of embryonic and adult stem cells. Science. 298:597-600, 2002.
139. Stuns A, Quackenbush J, Trajanoski Z: Genesis: cluster analysis of microarray data. Bioinformatics. 18:207-208, 2002.
140. Kuroda T, Tada M, Kubota H, Kimura H, Hatano S Y, Suemori N, Nakatsuji N, Tada T: Octamer and Sox elements are required for transcriptional cis regulation of Nanog gene expression. Mol Cell Biol. 25:2475-2485, 2005.
141. Rodda D J, Chew J L, Lim L H, Loh Y H, Wang B, Ng H H, Robson P: Transcriptional regulation of nanog by OCT4 and SOX2. J Biol Chem. 280:24731-24737, 2005.
142. Player A, Wang Y, Bhattacharya B, Rao M, Puri R K, Kawasaki E S: Comparisons between transcriptional regulation and RNA expression in human embryonic stem cell lines. Stem Cells Dev. 15:315-323, 2006.
143. Yoon Y S, Wecker A, Ileyd L, Park J S, Tkebuchava T, Kusano K, Hanley A, Scadova H, Qin G, Cha D H, Johnson K L, Aikawa R, Asahara T, Losordo D W: Clonally expanded novel multipotent stem cells from human bone marrow regenerate myocardium after myocardial infarction. J Clin Invest. 115:326-338, 2005.
144. Murasawa S, Kawamoto A, Horii M. Nakamori S, Asahara T: Niche-dependent translineage commitment of endothelial progenitor cells, not cell fusion in general, into myocardial lineage cells. Arterioscler Thromb Vasc Biol. 25:1388-1394, 2005.
145. Rota M, Kajstura J, Hosoda T, Bearzi C, Vitale S, Esposito G, Iaffaldano G, Padin-Ireguas M E, Gonzalez A, Rizzi R, Small N, Muraski J, Alvarez R, Chen X, Urbanek K, Bolli R, Houser S R, Leri A, Sussman M A, Anversa P: Bone marrow cells adopt the cardiomyogenic fate in vivo. Proc Natl Acad Sci USA. In press, 2007.
146. Jessup M, Brozena S: Heart failure. N Engl J. Med. 348:2007-2018, 2003.
147. Courville K A, Ventura H: Hypertension and heart failure: diagnosis and management. Curr Hypertens Rep. 8:185-190, 2006.
148. Anversa P, Olivetti G: Cellular basis of physiological and pathological myocardial growth. Handbook of Physiology: the Cardiovascular System. The Heart. New York: Oxford University Press. pp. 75-144, 2002.
149. Rakusan K: Assessment of cardiac growth of the heart in health and disease. New York: Raven Press. pp. 25-40, 1984.
150. Anversa P, Ricci R, Olivetti G: Quantitative structural analysis of the myocardium during physiologic growth and induced cardiac hypertrophy: a review. J Am Coll Cardiol. 7:1140-1149, 1986.
151. Anversa P, Kajstura J: Ventricular myocytes are not terminally differentiated in the adult mammalian heart. Circ Res. 13:1-14, 1998.
152. Rakusan K: Cardiac growth maturation and aging. Growth of the heart in health and disease. New York: Raven Press. pp 131-64, 1984.
153. MacLellan W R, Schneider M D: Death by design. Programmed cell death in cardiovascular biology and disease. Circ Res. 81:137-144, 1997.
154. Anversa P, Leri A, Beltrami C A, Guerra S, Kajstura J: Myocyte death and growth in the failing heart. Lab Invest. 78:767-786, 1998.
155. Haunstetter A, Izumo S: Apoptosis: basic mechanisms and implications for cardiovascular disease. Circ Res. 82:1111-1129, 1998.
156. Kang P M, Izumo S: Apoptosis and heart failure: A critical review of literature. Circ Res. 86:1107-1113, 2000.
157. Heineke J, Molkentin J D: Regulation of cardiac hypertrophy by intracellular signaling pathways. Mol Cell Biol. 7:589-600, 2006.
158. Wijns W. Vatner S F, Camici P G: Hibernating myocardium. N Engl J. Med. 339:173-181, 1998.
159. Hsieh P C H, Segers V F M, Davis M E, MacGillivray C, Gannon J, Molkentin J D, Robbins 0.1, Lee RT: Evidence from a genetic fate-mapping study that stem cells refresh adult mammalian cardiomyocytes after injury. Nature Med. 13:970-974, 2007.
160. Adams J W, Sakata Y, Davis M G, Sah V P, Wang Y, Liggett S B, Chien K R, Brown J H, Dorn G W: Enhanced Gαq signaling: A common pathway mediates cardiac hypertrophy and apoptotic heart failure. Proc Natl Acad Sci USA. 95:10140-10145, 1998.
161. Spees J L, Olson S D, Whitney M, Prockop D J: Mitochondrial transfer between cells can rescue aerobic respiration. Proc Natl Acad Sci USA. 103:1283-1288, 2006.
162. Moore K A, Lemischka I R: Stem cells and their niches. Science. 311:1880-1885, 2006.
163. Yin T, Li L: The stem cell niches in bone. J Clin Invest. 116:1195-1201, 2006.
164. Scadden D T: The stem-cell niche as an entity of action. Nature. 441:1075-1079, 2006.
165. Blau H M, Brazelton T R, Weimann J M: The evolving concept of a stem cell: entity or function? Cell. 105:829-841, 2001.
166. Spradling A, Drummond-Barbosa D, Kai T: Stem cells find their niche. Nature 414: 98-104, 2001.
167. Lin H: The stem cell niche theory: lessons from flies. Nat Rev Genet. 3:931-940, 2002.
168. Song X, Zhu C H, Doan C, Xie T: Germline stem cells anchored by adherens junctions in the Drosophila ovary niches. Science. 296:1855-1857, 2002.
169. Chen D, McKearin D: Dpp signaling silences barn transcription directly to establish asymmetric divisions of germline stem cells. Curr Biol. 13:1786-1791, 2003.
170. Zhu C H, Xie T: Clonal expansion of ovarian germline stem cells during niche formation in Drosophila. Development. 130:2579-2588, 2003.
171. Song X, Xie T: DE-cadherin-mediated cell adhesion is essential for maintaining somatic stem cell in the Drosophila ovary. Proc Natl Acad Sci USA. 99:14813-14818, 2002.
172. Kulessa H, Turk G, Hogan B L: Inhibition of Bmp signaling affects growth and differentiation in the anagen hair follicle. EMBO J. 19:6664-6674, 2000.
173. Stappenbeck T S, Mills J C, Gordon J I: Molecular features of adult mouse small intestinal epithelial progenitors. Proc Natl Acad Sci USA. 100:1004-1009, 2003.
174. Fuchs E, Tumbar T, Guasch G: Socializing with the neighbors: stem cells and their niche. Cell. 116:769-778, 2004.

175. Torella D, Rota M, Nurzynska D, Musso E, Monsen A, Shiraishi I, Zias E, Walsh K, Rosenzweig A, Sussman M A, Urbanek K, Nadal-Ginard B, Kajstura J, Anversa P, Leri A: Cardiac stem cell and myocyte aging, heart failure and IGF-1 overexpression. Circ Res. 94:514-524, 2004.

176. Perez-Moreno M, Jamora C, Fuchs E: Sticky business: orchestrating cellular signals at adherens junctions. Cell. 121:535-548, 2003.

177. Goldberg G S, Valiunas V, Bring P R: Selective permeability of gap junction channels. Biochim Biophys Acta. 1662:96-101, 2004.

178. Mitsunaga K, Araki K, Mizusaki H, Morohashi K, Haruna K, Nakagata N, Giguere V. Yamamura K, Abe K: Loss of PGC-specific expression of the orphan nuclear receptor ERR-beta results in reduction of germ cell number in mouse embryos. Mech Dev. 121: 237-246, 2004.

179. Pevny L, Placzek M: SOX genes and neural progenitor identity. Curr Opin Neurobiol. 15:7-13, 2005.

180. Loh Y H, Wu Q, Chew J L, Vega V B, Mang W, Chen X, Bourque G, George J, Leong B, Liu J, Wong K Y, Sung K W, Lee C W, Zhao X D, Chiu K P, Lipovich L, Kuznetsov V A, Robson P, Stanton L W, Wei C L, Ruan Y, Lim B, Ng H H: The Oct4 and Nanog transcription network regulates pluripotency in mouse embryonic stem cells. Nat Genet. 38:431-440, 2006.

181. Ivanova N, Dobrin R, Lu R, Kotenko J, Levorse J, DeCoste C, Xenia S, Lun Y, Lemischka I R: Dissecting self-renewal in stem cells with RNA interference. Nature. 444: 533-538, 2006.

182. Cairns L A, Moroni E, Levantini E, Giorgetti A, Klinger F G, Ronzoni S, Tatangelo L, Tiveron C, De Felici M, Dolci S, Magli M C, Giglioni B, Ottolenghi S: Kit regulatory elements required for expression in developing hematopoietic and germ cell lineages. Blood. 102:3954-3962, 2003.

183. Tillmanns J, Rota M, Hosoda T. Rotatori F, DeAngelis A, Amano K, Amano S, LeCapitaine N, Esposito G, Loredo M. Misao Y, Vitale S, Bearzi C, Urbanek K, Bolli R, Leri A, Kajstura J, Anversa P: Formation of large coronary arteries by cardiac stem cells: a biological bypass. Proc Natl Acad Sci USA. In revision, 2007.

184. Thyberg J, Hedin U, Sjolund M, Palmberg L, Bottger B A: Regulation of differentiated properties and proliferation of arterial smooth muscle cells. Arteriosclerosis. 10:966-990, 1990.

185. Brown K E, Kindy M S, Sonenshein G E: Expression of the c-myb proto-oncogene in bovine vascular smooth muscle cells. J Biol Chem. 267:4625-4630, 1992.

186. Wang J, Chen D, Walsh K: Regulation of Cdk2 activity in proliferating versus contact-inhibited endothelial cells: The role of the p27 cyclin kinase inhibitor. Circulation. 94: 1-524, 1996.

187. Hsiao R, Sharma H W, Ramakrishnan S, Keith E, Narayanan R: Telomerase activity in normal endothelial cells. Anticancer Res. 17:827-832, 1997.

188. Spyridopoulos I, Andres V: Control of vascular smooth muscle and endothelial cell proliferation and its implication in cardiovascular disease. Front Biosci. 1:d269-287, 1998.

189. Mahmud N, Devine S M, Weller K P, Parmar S, Sturgeon C, Nelson M C, Hewett T, Hoffman R: The relative quiescence of hematopoietic stem cells in nonhuman primates. Blood 97:3061-3068.

190. Savill N J: Mathematical models of hierarchically structured cell populations under equilibrium with application to the epidermis. Cell Prolif. 36:1-26, 2003.

191. Baserga R, Wiebel F: The cell cycle of mammalian cells. Int Rev Exp Pathol. 7:1-30, 1969.

192. Chen S, Lechleicder R J: Transforming growth factor-beta-induced differentiation of smooth muscle from a neural crest stem cell line. Circ Res. 94:1195-1202.

193. Urbich C, Heeschen C, Aicher A, Dernbach E, Zeiher A M, Dimmeler S: Relevance of monocytic features for neovascularization capacity of circulating endothelial progenitor cells. Circulation. 108:2511-2516, 2003.

194. Potente M, Urbich C, Sasaki K, Hofmann W K, Heeschen C, Aicher A, Kollipara R, DePinho R A, Zeiher A M, Dimmeler S: Involvement of Foxo transcription factors in angiogenesis and postnatal neovascularization. J Clin Invest. 115:2382-2392, 2005.

195. Lamagna C, Bergers G: The bone marrow constitutes a reservoir of pericyte progenitors. 0.1 Leukoc Biol. 26:677-681, 2006.

196. Lindskog H, Athley E, Larsson E, Lundin S, Hellstrom M, Lindahl P: New insights to vascular smooth muscle cell and pericyte differentiation of mouse embryonic stem cells in vitro. Arterioscler Thromb Vase Biol. 26:1457-1464, 2006.

197. Berenson M L, Levine D M, Rindskopf D: Applied statistics. Prentice Hall, Englewood Cliffs, N.J. pp. 557.

198. Souilhol C, Cormier S, Monet M, Vandormael-Poumin S, Joutel A, Babinet C, Cohen-Tannoudji M: NAS transgenic mouse line allows visualization of Notch pathway activity in vivo. Genesis. 44:277-286, 2006.

199. Dimmeler S, Zeiher A M, Schneider M D: Unchain my heart: the scientific foundations of cardiac repair. J Clin Invest. 115:572-583, 2005.

200. Rubart M, Field L T: Cardiac regeneration: repopulating the heart. Annu Rev Physiol. 68:29-49, 2006.

201. Murry C E, Soonpaa M H, Reinecke H, Nakajima H, Nakajima H O, Rubart M, Pasumarthi K B, Virag J I, Bartehnez S H, Poppa V, Bradford G, Dowell J D, Willaims D A, Field L J: Haematopoietic stem cells do not transdifferentiate into cardiac myocytes in myocardial infarcts. Nature. 428:664-668, 2004.

202. Nygren J M, Jovinge S, Breitbach M, Sawen P, Roll W. Hescheler J, Taneera J, Fleishcmann B K, Jacobsen S E: Bone marrow-derived hematopoietic cells generage cardomyocytes at a low frequency through cell fusion, but not transdifferentaiation. Nat Med. 10:494-501, 2004.

203. Balsam L B, Wagers A J, Christensen J L, Kofidis T, Weissman I L, Robbins R C: Haematopoietic stem cells adopt mature haematopoietic fates in ischemic myocardium. Nature. 428:668-673, 2004.

204. Tosh D, Slack J M: How cells change their phenotype. Nat Rev Mol Cell Biol. 3: 187-194, 2002.

205. Pomerantz J, Blau H M: Nuclear reprogramming: a key to stem cell function in regenerative medicine. Nat Cell Biol. 6:810-816, 2004.

206. Leri A, Kajstura J, Anversa P: Identity deception: not a crime for a stem cell. Physiology. 20:162-168, 2005.

207. Kajstura J, Leri A, Bolli R, Anversa P: Endothelial progenitor cells: neovascularization or more? J Mol Cell Cardiol. 40:1-8, 2006.

208. Schroeder T, Fraser S T, Ogawa M, Nishikawa S, Oka C, Bornkamm G V, Nishikawa S, Honjo T, Just U: Recombination signal sequence-binding protein Jkappa alters mesodermal cell fate decisions by suppressing cardiomyogenesis. Proc Natl Acad Sci USA. 100:4018-4023, 2003.

209. Han H, Tanigaki K, Yamamoto N, Kuroda K, Yoshimoto M, Nakahata T, Ikuta K, Honjo T: Inducible gene knockout of transcription factor recombination signal binding protein-J reveals its essential role in T versus B lineage decision. Int Immunol. 14:637-645, 2002.

210. Okada S, Nakauchi H, Nagayoshi K, Nishikawa S, Nishikawa S, Miura Y, Suda T: Enrichment and characterization of murine hematopoietic stem cells that express c-kit molecule. Blood. 78:1706-1712, 1991.

211. Orlic D, Fischer R, Nishikawa S, Nienhuis A W, Bodine D M: Purification and characterization of heterogeneous pluripotent hematopoietic stem cell populations expressing high levels of c-kit receptor. Blood. 82:762-770, 1993.

212. Balazs A B, Fabian A J, Esmon C T, Mulligan R C: Endothelial protein C receptor (CD201) explicitly identifies hematopoietic stem cells in murine bone marrow. Blood. 107:2317-2321, 2006.

213. Dumble M, Moore L, Chambers S M, Geiger H, Van Zant G, Goodell M A, Donehower L A: The impact of altered p53 dosage on hematopoietic stem cell dynamics during aging. Blood. 109:1736-1742, 2007.

214. Kawada H, Fujita J, Kinjo K, Matsuzaki Y, Tsuma M, Miyatake H, Muguruma Y, Tsuboi K, Itabashi Y, Ikeda Y, Ogawa S, Okano H. Hotta T, Ando K, Fukuda K: Nonhematopoietic mesenchymal stem cells can be mobilized and differentiate into cardiomyocytes after myocardial infarction. Blood. 104:3581-3587, 2004.

215. Kopan R: All good things must come to an end: how is Notch signaling turned off? Sci STKE. PEE 1999.

216. Kopan R: Notch: a membrane-bound transcription factor. 1 Cell Sci. 115:1095-1097, 2002.

217. Iwatsubo T: The gamma-secretase complex: machinery for intramembrane proteolysis. Curr Opin Neurobiol. 14:379-393, 2004.

218. Quesenberry P J: The continuum model of marrow stem cell regulation. Curr Opin Hematol. 13:216-221, 2006.

219. Quesenberry P J, Colvin G A, Abedi M, Dooner G, Dooner M, Aliotta J, Keaney P, Luo L, Demers D, Peterson A, Foster B, Greer D: The stem cell continuum. Ann NY Acad Sci. 1044:228-235, 2005.

220. Lemischka I R: Microenvironmental regulation of hematopoietic stem cells. Stem Cells. 15:63-68, 1997.

221. Hackney J A, Charbord P, Brunk B P, Stoeckert C J, Lemischka I R, Moore K A: A molecular profile of a hematopoietic stem cell niche. Proc Natl Acad Sci USA. 99:13061-13066, 2002.

222. Juan G, Gruenwald S, Darzynkiewicz Z: Phosphorylation of retinoblastoma susceptibility gene protein assayed in individual lymphocytes during their mitogenic stimulation. Exp Cell Res. 239:104-110, 1998.

223. Darzynkiewicz Z, Juan G, Traganos F: Cytometry of cell cycle regulatory proteins. Prog Cell Cycle Res. 5:533-542, 2003.

224. Juan G, Darzynkiewicz Z: Detection of cyclins in individual cells by flow and laser scanning cytometry. Methods Mol Biol. 91:67-75, 1998.

225. Cheng L C, Tavazoie M, Doetsch F: Stem cells: from epigenetics to microRNAs. Neuron. 46:363-367, 2005.

226. Ko M S, McLaren A: Epigenetics of germ cells, stem cells, and early embryos. Dev Cell. 10:161-166, 2006.

227. Shivdasani R A: MicroRNAs: regulators of gene expression and cell differentiation. Blood. 108:3646-3653, 2006.

228. Lee M S, Jun D H, Hwang C I, Park S S, Kang J J, Park H S, Kim J, Kim J H, Seo J S, Park W Y: Selection of neural differentiation-specific genes by comparing profiles of random differentiation. Stem Cells. 24:1946-1955, 2006.

229. Fazel S, Cimini M, Chen L, Li S, Angoulvant D, Fedak P, Velma S, Weisel R D, Keating A, Li R K: Cardioprotective c-kit+ cells are from the bone marrow and regulate the myocardial balance of angiogenic cytokines. J Clin Invest. 116:1865-1877, 2006.

230. Weissman I L, Anderson D J, Gage F: Stem and progenitor cells: origins, phenotypes, lineage commitments and transdifferentiations. Annu Rev Cell Dev Biol. 17:387-403, 2001.

231. Bhattacharya B, Miura T, Brandenberger R, Mejido J, Luo Y, Yang A X, Joshi B H, Ginis I, Thies R S, Amit M, Lyons 1, Condie B G, Itskovitz-Eldor J, Rao M S, Puri R K: Gene expression in human embryonic stem cell lines: unique molecular signature. Blood. 103:2956-2964, 2004.

232. Brandenberger R, Wei H, Zhang S, Lei S, Murage J, Fisk G J, Li Y, Xu C, Fang R, Gueglar K, Rao M S, Mandalam R, Lebkowski J, Stanton L W: Transcriptome characterization elucidates signaling networks that control human ES cell growth and differentiation. Nat Biotechnol. 22:707-716, 2004.

233. Ginis I, Luo Y, Miura T, Thies S, Brandenberger R, Gerecht-Nir S, Amit M, Hoke A, Carpenter M K, Itskovitz-Eldor J, Rao M S: Differences between human and mouse embryonic stem cells. Dev Biol. 269:360-380, 2004.

234. Brazma A, Hingamp P, Quackenbush J, Sherlock G, Spellman P, Stoeckert C, Aach J, Ansorge W, Ball C A, Causton H C, Gaasterland T, Glenisson P, Holstege F C, Kim I F, Markowitz V, Matese J C, Parkinson H, Robinson A, Sarkans U, Schulze-Kremer S, Stewart J, Taylor R, Vilo J, Vingron M: Minimum information about a microarray experiment (MIAME)-toward standards for microarray data. Nat Genet. 29:365-371, 2001.

235. Draghici S, Khatri P, Bhaysar P, Shah A, Krawetz S A, Tainsky M A: Onto-Tools, the toolkit of the modern biologist: Onto-Express, Onto-Compare, Onto-Design and Onto-Translate. Nucleic Acids Res. 31:3775-3781, 2003.

236. Olson E N, Schneider M D: Sizing up the heart: development redux in disease. Genes Dev. 17:1937-1956, 2003.

237. Chien K R, Olson E N: Converging pathways and principles in heart development and disease: CV@CSH. Cell. 110:153-162, 2002.

238. Grossman W, Jones D, McLaurin L P: Wall stress and patterns of hypertrophy in the human left ventricle. J Clin Invest. 56:56-64, 1975.

239. Blake J, Devereux R B, Herrold E M, Jason M, Fisher J, Borer J S, Laragh J H: Relation of concentric left ventricular hypertrophy and extracardiac target organ damage to supranormal left ventricular performance in established essential hypertension. Am J. Cardiol. 62:246-252, 1988.

240. Devereux R B, Roman M J, Palmieri V, Okin P M, Boman K, Gerdts E, Nieminen M S, Papademetriou V, Wachtell K, Dahlof B: Left ventricular wall stresses and wall stress-mass-heart rate products in hypertensive patients with electrocardiographic left ventricular hypertrophy: the LIFE study. J. Hypertens. 18:1129-1138, 2000.

241. Olivetti G, Ricci R, Anversa P: Hyperplasia of myocyte nuclei in long-term cardiac hypertrophy in rats. J Clin Invest. 80:1818-1821, 1987.

242. Olivetti G, Ricci R, Lagrasta C, Manica E, Sonnenblick E H, Anversa P: Cellular basis of wall remodeling in long-term pressure overload-induced right ventricular hypertrophy in rats. Circ Res. 63:648-657, 1988.

243. Olivetti G, Melissari M, Balbi T, Quaini F, Cigola E, Sonnenblick E H, Anversa P: Myocyte cellular hypertrophy is responsible for ventricular remodeling in the hypertrophied heart of middle aged individuals in the absence of cardiac failure. Cardiovasc Res. 28:1199-1208, 1994.

244. Haider A W, Larson M G, Benjamin E J, Levy D: Increased left ventricular mass and hypertrophy are associated with increased risk for sudden death. J Am Coll Cardiol. 32: 1454-1459, 1998.

245. Berenji K, Drazner M H, Rothermel B A, Hill J A: Does load-induced ventricular hypertrophy progress to systolic heart failure? Am J Physiol Heart. 289:H8-H16, 2005.

246. Capasso J M, Palackal T, Olivetti G, Anversa P: Left ventricular failure induced by long-term hypertension in rats. Circ Res. 66:1400-1412, 1990.

247. Anversa P, Palackal T, Sonnenblick E H, Olivetti G, Capasso J M: Hypertensive cardiomyopathy. Myocyte nuclei hyperplasia in the mammalian rat heart. J Clin Invest. 85:994-997, 1990.

248. Olivetti (3, Melissari M Baibi T, Quaini F, Sonnenblick E H, Anversa P: Myocyte nuclear and possible cellular hyperplasia contribute to ventricular remodeling in the hypertrophic senescent heart in humans. J Am Coll Cardiol. 24:140-149, 1994.

249. Gradman A H, Alfayoumi F: From left ventricular hypertrophy to congestive heart failure: management of hypertensive heart disease. Prog Cardiovasc Dis. 48:326-341, 2006.

250. Wiesel P, Mazolai L, Nussberger J, Pedrazzini T: Two-kidney, one clip and one-kidney, one clip hypertension in mice. Hypertension. 29:1025-1030, 1997.

251. Yang X P, Liu Y H, Rhaleb N E, Kurihara N, Kim H E, Carretero O A: Echocardiographic assessment of cardiac function in conscious and anesthetized mice. Am J. Physiol. 277:111967-H1974, 1999.

252. Murat A, Pellieux C, Brunner H R, Pedrazzini T: Calcineurin blockade prevents cardiac mitogen-activated protein kinase activation and hypertrophy in renovascular hypertension. J Biol Chem. 275:40867-40873, 2000.

253. Mazzolai L, Pedrazzini T, Nicoud F, Gabbiani G, Brunner H R, Nussberger J: Increased cardiac angiotensin II levels induce right and left ventricular hypertrophy in normotensive mice. Hypertension. 35:985-991, 2000.

254. Anversa P, Capasso J M: Loss of intermediate-sized coronary arteries and capillary proliferation after left ventricular failure in rats. Am J. Physiol. 260:H1552-1560, 1991.

255. Capasso J M, Puntillo E, Halpryn B, Olivetti G, Li P, Anversa P: Amelioration of effects of hypertension and diabetes on myocardium by cardiac glycoside. Am J. Physiol. 262:13734-742, 1992.

256. Anversa P, Li P, Malhotra A, Zhang X, Herman M V, Capasso J M: Effects of hypertension and coronary constriction on cardiac function, morphology and contractile proteins in rats. Am J. Physiol. 265:H713-724, 1993.

257. Li P, Zhang X, Capasso J M, Meggs L G, Sonnenblick E H, Anversa P: Myocyte loss and left ventricular failure characterize the long term effects of coronary artery narrowing or renal hypertension in rats. Cardiovasc Res. 27:1066-1075, 1993.

258. Rota M, LeCapitaine N, Hosoda T, Boni A, De Angelis A, Padin-Iruegas M E, Esposito G, Vitale S, Urbanek K, Casarsa C, Giorgio M, Luscher T F, Pelicci P G, Anversa P, Leri A, Kajstura J: Diabetes promotes cardiac stem cell aging and heart failure, which are prevented by deletion of the p66shc gene. Circ Res. 99:42-52, 2006.

259. Beltrami C A, Di Loreto C, Finato N, Rocco M, Artico D, Cigola E, Gambert S R, Olivetti G. Kajstura J, Anversa P. Proliferating cell nuclear antigen (PCNA), DNA synthesis and mitosis in myocytes following cardiac transplantation in man. J Mol Cell Cardiol. 29: 2789-2802, 1997.

260. Kajstura J, Leri A, Finato N, Di Loreto C, Beltrami C A, Anversa P. Myocyte proliferation in end-stage cardiac failure in humans. Proc Natl Acad Sci USA. 95: 8801-8805, 1998

261. Anversa P, Leri A, Beltrami C A, Guerra S, Kajstura J. Myocyte death and growth in the failing heart. *Lab Invest.* 1998; 78:767-86.

262. Beltrami A P, Urbanek K, Kajstura J, Yan S M, Finato N. Bussani R, Nadal-Ginard B, Silvestri F, Leri A, Beltrami C A, Anversa P. Evidence that human cardiac myocytes divide after myocardial infarction. *N Eng J Med.* 2001; 344:1750-7.

263. Anversa P, Nadal-Ginard B. Myocyte renewal and ventricular remodeling. *Nature.* 2002; 415:240-3.

264. Anversa P, Leri A, Kajstura J, Nadal-Ginard B. Myocyte growth and cardiac repair. *J Mol Cell Cardiol.* 2002; 34:91-105.

265. Anversa P, Leri A. Myocardial regeneration. In: Zipes, Libby, Bonow, Braunwald eds. *Braunwald's Heart Disease A Textbook of Cardiovascular Medicine* 7th Edition. Elsevier Saunders, Philadelphia, Pa. 2005; 1911-1923.

266. Leri A, Kajstura J, Anversa P. Cardiac stem cells and mechanisms of myocardial regeneration. *Physiol Rev.* 2005; 85:1373-416.

267. Urbanek K, Torella D, Sheikh F, De Angelis A, Nurzynska D, Silvestri F, Beltrami C A, Bussani R, Beltrami A P, Quaini F, Bolli R, Leri A, Kajstura J, Anversa P. Myocardial regeneration by activation of multipotent cardiac stem cells in ischemic heart failure. *Proc Natl Acad Sci USA.* 2005; 102:8692-7.

268. Anversa P, Kajstura J, Leri A, Bolli R. Life and death of cardiac stem cells: a paradigm shift in cardiac biology. *Circulation.* 2006; 113:1451-63.

269. Anversa P, Leri A, Kajstura J. Cardiac regeneration. *J Am Coll Cardiol.* 2006; 47:1769-76.

270. Anversa P, Leri A, Rota M, Bearzi C. Urbanek K, Kajstura J, Bolli R. Stem Cells, Myocardial regeneration and methodological artifacts. *Stem Cells.* 25: 589-601, 2007.

271.13. Wicker P, Tarazi R C. Coronary blood flow in left ventricular hypertrophy: a review of experimental data. *Eur Heart J.* 1982; 3 Suppl A:111-8.

272. Harrison D G, Barnes D H, Hiratzka L F, Eastham C L, Kerber R E, Marcus M L. The effect of cardiac hypertrophy on the coronary collateral circulation. *Circulation.* 1985; 71:1135-45.

273. Bache R J. Effects of hypertrophy on the coronary circulation. *Prog Cardiovasc Dis.* 1988: 30:403-40.

274. Karam R, Healy B P, Wicker P. Coronary reserve is depressed in postmyocardial infarction reactive cardiac hypertrophy. *Circulation.* 1990; 81:238-46.

275. Myocardial reperfusion imaging: basic principals and clinical applications. *Am J Card Imaging.* 1993; 7:11-23.

276. Giordano A, Trani C, Lombardo A. Maseri A. Detection of hibernated myocardium using intracoronary technetium-99m-sestamibi. *Q J Nucl Med.* 1997; 41:46-50.

277. Hansen C L, Rastogi A, Sangrigoli R. On myocardial perfusion, metabolism, and viability. *J Nucl Cardiol.* 1998; 502-5.

278. Mari C, Strauss W H. Detection and characterization of hibernating myocardium. *Nucl Med Comun.* 2002; 23:311-22.

279. Chin B B, Esposito G. Kraitchman D L. Myocardial contractile reserve and perfusion defect severity with rest and stress dobutamine (99m)Tc-sestamibi SPECT in canine stunning and subendocardial infarction. *J Nucl Med.* 2002; 43:540-50.

280. Paeng J C, Lee D S, Cheon G J, Kim K B, Yeo J S, Chung J K, Lee M C. Consideration of perfusion reserve in viability assessment by myocardial T1-201 rest-redistribution SPECT: a quantitative study with dual-isotope SPECT. *J Nucl Cardiol.* 2002; 9:68-74.

281. Sciagra R, Leoncini M, Mennuti A, Dabizzi R P, Pupi A. Classification of ischemic dysfunctional myocardium combining perfusion quantification and contractile reserve evaluation using nitrate-enhanced gated single photon emission computed tomography with dobutamine test. *Q J Nucl Med Mol Imaging.* 2004; 48:4-11.

282. Anversa P and Olivetti G. Cellular basis of physiological and pathological myocardial growth. In: *Handbook of Physiology. The Cardiovascular System. The Heart.* Bethesda, Md., 2002, sect. 2 chapter 2:75-144.

283. Lefkowitz R J, Caron M G, Stiles G L. Mechanisms of membrane-receptor regulation. Biochemical, physiological, and clinical insights derived from studies of the adrenergic receptors. *N Engl J Med.* 1984; 310:1570-9.

284. Schrier R W, Abraham W T. Hormones and hemodynamics in heart failure. *N Engl J Med.* 1999; 341:577-85.

285. Klein I, Ojamaa K. Thyroid hormone and the cardiovascular system. *N Engl J. Med.* 2001; 344:501-9.

286. Weber K T. Aldosterone in congestive heart failure. *N Engl J Med.* 2001; 345:1689-97.

287. Jessup M, Brozena S. Heart failure. *N Engl J Med.* 2003; 348:2007-18.

288. Aurigemma G P, Gaasch W H. Clinical practice. Diastolic heart failure. *N Engl J Med.* 2004; 351:1097-1105.

289. www.americanheart.org/statistics

290. Libby P, Aikawa M. Stabilization of atherosclerotic plaques: new mechanisms and clinical targets. *Nat Med.* 2002; 8:1257-62.

291. Libby P, Theroux P. Pathophysiology of coronary artery disease. *Circulation.* 2005; 111:3481-8.

292. Ross R. Atherosclerosis—an inflammatory disease. *N Engl J Med.* 1999; 340:115-26.

293. Hansson G K. Inflammation, atherosclerosis, and coronary artery disease. *N Engl J Med.* 2005; 352:1685-95.

294. Weber C. Platelets and chemokines in atherosclerosis: partners in crime. *Circ Res.* 2005; 96:612-6.

295. Libby P, Ridker R. Inflammation and atherothrombosis from population biology and bench research to clinical practice. *J Am Coll Cardiol.* 2006; 48:A33-46.

296. Croce K, Libby P. Intertwining of thrombosis and inflammation in atherosclerosis. *Curr Opin Hematol.* 2007; 14:55-61.

297. Maseri A, Luster V. Is there a vulnerable plaque? *Circulation.* 2003; 107:2076-71.

298. Slager C J, Wentzel J J, Gijsen F J, thury A, van der Wal A C, Schaar J A, Serruys P W. The role of shear stress in the destabilization of vulnerable plaques and related therapeutic implications. *Nat Clin Pract Cardiovasc Med.* 2005; 2:456-64.

299. Fuster V, Moreno P R, Fayad Z A, Corti R, Badimon J J. Atherothrombosis and high-risk plaque: part I: evolving concepts. *J Am Coll Cardiol.* 2005; 46:937-54.

300. Kolodgie F D, Burke A P, Farb A, Gold H K, Yuan J, Narula J, Finn A V, Virmani R. the thin-cap fibroatheroma: a type of vulnerable plaque: the major precursor lesion to acute coronary syndromes. *Curr Opin Cardiol.* 2001; 16:285-92.

301. Linke A, Muller P, Nurzynska D, Casarsa C, Torella D, Nascimbene A, Castaldo C, Cascapera S, Bohm M, Quaini F, Urbanek K, Leri A, Hintze T H, Kajstura J, Anversa P. Stem cells in the dog heart are self-renewing, clonogenic, and multipotent and regenerate infracted myocardium, improving cardiac function. *Proc Natl Acad Sci USA.* 2005; 102:8966-8971.

302. Melton D A, Cowen C. "Stemness": Definitions, Criteria, and Standards. In: Lanza R, Blau H, Melton D, Moore M, Thomas E D, Verfaillie C, Weissman I, West M. eds. *Handbook of Stem Cells Volume 2. Adult and Fetal* Elsevier Academic Press. 2004; 136:xxv-xxx.

303. Verfaillie C M. "Adult" stem cells: tissue specific or not? In: Lanza R, Blau H, Melton D, Moore M, Thomas E D, Verfaillie C, Weissman I, West M. eds. *Handbook of Stem Cells. Volume 2. Adult and Fetal Stem Cells.* Elsevier Academic Press. 2004; 137:13-20.

304. Bearzi C, Rota M, Hosoda T, Tillmanns J, Nascimbene A, De Angelis A, Yasuzawa-Amano S, Trofimova 1, Siggins R W, Cascapera S, Beltrami A P, Zias E, Quaini F, Urbanek K, Michler R E, Bolli R, Kajstura J, Leri A, Anversa P: Human cardiac stem cells. Proc Natl Acad Sci USA. 104: 14068-14073, 2007.

305. Fehling H J, Lacaud G, Kubo A, Kennedy M, Robertson S, Keller G and Kouskoff V. Tracking mesoderm induction and its specification to the hemangioblast during embryonic stem cell differentiation. *Development.* 2003; 130: 4217-4227.

306. Kouskoff V, Lacaud G, Schwantz S, Fehling H J and Keller G. Sequential development of hematopoietic and cardiac mesoderm during embryonic stem cell differentiation. *Proc Natl Acad Sci USA.* 2005; 102:13170-13175.

307. Carmeliet P. Angiogenesis in life, disease and medicine. *Nature.* 2005; 438:932-936.

308. Coultas L, Chawengsaksophak K and Rossant J. Endothelial cells and VEGF in vascular development. *Nature.* 2005; 438:937-945.

309. Kattman S J, Huber T L, Keller G M. Multipotent Flk-1+ cardiovascular progenitor cells give rise to the cardiomyocyte, endothelial, and vascular smooth muscle lineages. *Developmental Cell.* 2006; 11:723-732.

310.52 Ferrarini M, Arsic N, Recchia F A, Zentilin L, Zacchigna S, Xu X, Linke A, Giacca M, Hintze T H. Adeno-associated virus-mediated transduction of VEGF165 improves cardiac tissue viability and functional recovery after permanent coronary occlusion in conscious dogs. *Circ Res.* 14; 98(7):954-61, 2006

311. Beltrami A P, Barlucchi L, Torella D, Baker M, Limana F, Chimenti S, Kasahara H, Rota M, Musso E, Urbanek K, Leri A, Kajstura J, Nadal-Ginard B, Anversa P. Adult cardiac stem cells are multipotent and support myocardial regeneration. Cell 114:1-20, 2003.

312. Bearzi C, Muller P, Amano K, Tang X-L, Loredo M, Mosna F, Gatti A, Esposito G, Leri A, Kajstura J, Anversa P, Rimoldi O, Bolli R: Identification and characterization of cardiac stem cells in the pig heart. Circulation. 114: 11-125, 2006.

313. Bolli R, Jneic H, Tang X-L, Rimoldi O, Mosna F, Loredo M, Gatti A, Kajstura J, Leri A, Bearzi C, Abdel-Latit A, Anversa P. Intracoronary administration of cardiac stem cells improves cardiac function in pigs with old infarction. *Circulation.* 2006; 114:11-239.

314. Reya T, Morrison S J, Clarke M F, Weissman I L. Stem cells, cancer, and cancer stem cells. *Nature.* 2001: 414:105-11.

315. Fuchs E, Raghavan S. Getting under the skin of epidermal morphogenesis. *Nat Rev Genet.* 2002; 3:199-209.

316. Alonso L, Fuhs E. Stem cells of the skin epithelium. *Proc Natl Acad Sci USA.* 2003; 100 Suppl:11830-5.

317. Lapidot T, Petie I. Current understanding of stem cell mobilization: the roles of chemokines, proteolytic enzymes, adhesion molecules, cytokines, and stromal cells. *Exp Hematol.* 2002; 30:973-981.

318. Quesenberry P J, Colvin G, Abedi M. Perspective: fundamental and clinical concepts on stem cell homing and engraftment: a journey to niches and beyond. *Exp Hematol.* 2005; 33:9-19.

319. Dawn B, Stein A B, Urbanek K, Rota M, Whang B, Rastaldo R, Torella D, Tang X L, Rezazadeh A, Kajstura J, Leri A, Hunt G, Varma J, Prabhu S D, Anversa P, Bolli R. Cardiac stem cells delivered intravascularly traverse the vessel barrier, regenerate infracted myocardium, and improve cardiac function. *Proc Natl Acad Sci USA.* 2005; 102:3766-3771.

320. Wei C-J, Xu X, Lo C W. Connexins and cell signaling in development and disease. *Annu Rev Cell Dev Biol* 2004; 20:811-38.

321. Doetsch F. A niche for adult neural stem cells. *Curr Opin Genet Dev.* 2003; 13:543-50.

322. Li L, Xie T. Stem cell niche: structure and function. *Annu Rev Cell Dev Biol.* 2005; 21:605-31.

323. Kopp H-G, Avecilla S T, Hooper A T, Rafii S. The bone marrow vascular niche: home of HSC differentiation and mobilization. *Physiology.* 2005; 20:349-356.

324. Hayashi R, Yamato M, Sugiyaa H, Sumide T, Yang J, Okano T. Tano Y, Nishida K. N-cadherin is expressed by putative stem/progenitor cells and melanocytes in the human limbal epithelial stem cell niche. *Stem Cells.* 2006. [Epub ahead of print].

325. Frisch S M, Ruoslahti E. Integrins and anoikis. *Curr Opin Cell Biol.* 1997; 9:701-706.

326. Frisch S M, Screaton R A. Anoikis mechanisms. *Curr Opin Cell Biol.* 2001; 13:555-562.

327. Melendez J, Turner C, Avraham H, Steinberg S F, Schaefer E, Sussman M A. Cardiomyocyte apoptosis triggered by RAFTK/pyk2 via Src kinase is antagonized by paxillin. *J Biol Chem.* 2004; 279:53516-23.

328. Reddig P J, Juliano R L. Clinging to life: cell to matrix adhesion and cells survival. *Cancer Metastasis Rev.* 2005; 24:425-439.

329. Patel, M., J. M. Stewart, A. V. Loud, P. Anversa, J. Wang, L. Fiegel and T. H. Hintze. Altered function and structure of the heart in dogs with chronic elevation in plasma norepinephirne. *Circulation* 84:2091-2100, 1991.

330. Hintze, T. H. and Vatner, S. F.: Comparison of effects of nifedipine and nitroglycerin on large and small coronary arteries and cardiac function in conscious dogs. *Circ. Res.* (Suppl 1) 52: 139-146, 1983

331. Bernstein K W, Ochoa F Y, Xu X, Forfia P, Shen W, Thompson C I and Hintze T H. Function and production of nitric oxide in the coronary circulation of the conscious dog during exercise. *Circ Res* 79:840-848, 1996

332. Wang J, Wolin M S and Hintze T H. Chronic exercise enhances endothelium-mediated dilation of epicardial coronary artery in conscious dogs. *Circ. Res* 73:829-838, 1993.

333. Sessa W C, Pritchard K, Seyedi N, Wang J and Hintze T H. Chronic exercise in dogs increases coronary vascular nitric oxide production and endothelial cell nitric oxide synthase gene expression. *Circ Res* 74:349-353, 1994.

334. Shen W Q, Zhang X P, Zhao G, Wolin M S, Sessa W and Hintze T H. Nitric oxide production and upregulation of NO synthase gene expression contribute to vascular regulation during exercise and may be responsible for the beneficial vascular effects of aerobic exercise training. *Med Sci Sports Exer* 27:1125-1134, 1994.

335. Stanley W C, Recchia F A, Lopashuk G D. Myocardial substrate metabolism in the normal and failing heart. *Physiol Rev* 85:1093-1129, 2005.

336. Ollson R A, Gregg D E. Myocardial reactive hyperemia in the unanesthetized dog. *Am J Physiol* 208:224-230, 1965

337. Hintze, T H., Kaley, G.: Prostaglandins and the control of blood flow in the canine myocardium. *Circ Res.* 40: 313-320, 1977.

338. Hintze, T. H., Vatner, S. F.: Reactive dilation of large coronary arteries following brief coronary occlusion in conscious dogs. *Circ. Res.* 54: 50-57, 1984.

339. Vatner S F, Franklin D, Higgins C B, Patrick T, Braunwald E. Left ventricular response to severe exertion in untethered dogs. *J Clin Invest* 51:3052-3060, 1972.

340. Vatner S F, Pagani M. Cardiovascular adjustments to exercise: hemodynamics and mechanisms. *Prog Cardiovasc Dis* 19:91-108, 1976.

341. Van Citters R L, Franklin D. Cardiovascular performance of Alaska sled dogs during exercise. *Circ Res* 24:33-42, 1969.

342. Williams J G, Rincon-Skinner I, Sun D, Wang X, Zhang S, Zhang X, Hintze T H. Role of NO in coupling myocardial oxygen consumption and coronary vascular dynamics during pregnancy in the dog. *Am J Physiol* (In Press 2007)

343. Vatner S F, Correlation between acute reductions in myocardial blood flow and function in conscious dogs. *Circ Res* 47:201-207, 1980

344. Kajstura J, Bolli R, Sonnenblick E H, Anversa P. Cause of death: suicide. *J Molec Cardiol* 40:425-437, 2006

345. Beltrami A P, Urbanek K, Kajstura J, Yan S M, Finato N, Bussani R, Nadal-Ginard B, Silvestri F, Led A, Beltrami C A, Anversa P. Evidence that human cardiac myocytes divide after myocardial infarction. *N Engl J Med.* 344: 1785-1787, 2001.

346. Anversa P, Leri A, Kajstura J. Cardiac regeneration. *J Am Coll Cardiol* 47:1769-1776, 2006.

347. Lavallee M, Cox D, Patrick T A, Vatner S F. Salvage of myocardial function by coronary artery reperfusion 1, 2, and 3 hours after occlusion in conscious dogs. *Circ Res* 53:235-247, 1983.

348. Gallagher K P. W(h)ither myocardial reperfusion injury. *J Thromb Thrombolysis* 4:137-139, 1997.

349. Leri A, Kajstura J, Anversa P. Cardiac stem cells and mechanisms of cardiac regeneration. *Physiol Rev* 85:1373-1416, 2005.

350. Nadal-Ginard, Kajstura J, Anversa P. Myocyte death, growth, and regeneration in cardiac hypertrophy and failure. *Circ Res* 92:139-150, 2003.

351. Li W, Mital S, Ojaimi C, Csiszar A, Kaley G, Hintze T H. Premature death and age-related cardiac dysfunction in male eNOS-knockout mice. *J. Mol. Cell Cardiol.* 37(3): 671-90, 2004.

352. Quinones M A, Gaassch W H, Alexander J K. Influence of acute changes in preload, afterload, contractile state and heart rate on ejection and isovolumic indices of myocardial contractility in man. *Circulation* 53: 293-302, 1976

353. Vatner S F. Effects of anesthesia on cardiovascular control mechanisms. Environ Health Perspect. 26:193-206, 1978.

354. Kajstura J, Zhang X, Liu Y, Szoke E, Cheng W, Olivetti G, Hintze T H and Anversa P. Cellular basis of pacing-induced dilated myopathy:myocyte cell loss and myocyte cellular hypertrophy. *Circulation* 92:2306-2317, 1995.

355. Liu Y, Cignola E, Cheng W. Kajstura J, Olivetti G, Hintze T H and Anversa P. Myocyte nuclear mitotic division and programmed cell death characterize the cardiac myopathy induced by rapid ventricular pacing in dogs. *Lab Invest* 73:771-787, 1995.

356. Cheng W, Sheng B. Kajstura J. Li P, Wolin M S, Sonnenblick E, Hintze T H, Olivetti G and Anversa P. Stretch-induced programmed myocyte cell death. *J Clin Invest* 96:2247-2259, 1995.

357. Leri A, Malhotra A, Li Q, Stiegler P, Claudio P P, Giordano A, Kajstura J, Hintze T H and Anversa P. Pacing-induced heart failure in dogs enhances the expression of p53 and p53-dependent genes in ventricular myocytes. *Circulation* 97:194-203, 1998

358. Setoguchi M, Leri A, Wang S, Liu Y, DeLuca A, Giordano A, Hintze T H, Kajstura J and Anversa P. Activation of cyclins and cyclin-dependent kinases, DNA replication and myocyte proliferation in pacing-induced heart failure in dogs. *Lab Invest* 79:1545-1558, 1999.

359. Barlucci L, Leri A, Dostal D E, Fiordaliso F, Tada H, Hintze T H, Kajstura J, Nadal-Ginard B, Anversa P. Canine ventricular myocytes possess a renin-angiotensin system which is upregulated with heart failure. *Circ Res* 2001; 88: 298-304.

360. Cesselli D. I Jakoniuk, L Barlucchi, A P Beltrami, T H Hintze, B Nadal-Ginard. Oxidative stress-mediated cardiac cell death is a major determinant of ventricular dysfunction and failure in dog dilated cardiomyopathy. *Circ Res*. 89:279-86, 2001.

361. Leri A, L Barlucchi, F Limana, A Deptala, Z Darzynkiewicz, T H Hintze, J Kajstura, B Nadal-Ginard, P Anversa. Telomerase expression and activity are coupled with myocyte proliferation a preservation of telomeric length in the failing heart. *Proc Natl Aca Sci*. 98:8626-31, 2001.

362. Post H, Kajstura J, Lei B, Sessa W B, Byrne B, Anversa P, Hintze T H, Recchia F A. Adeno-associated virus medicated gene delivery into coronary microvessels of chronically instrumented dogs. *J Appl Physiol* 95:1688-1694, 2003.

363. Davis M E, Hsieh P C, Takashi T, Song Q, Zhang S, Kamm R D, Grodz A J, Anversa P, Lee R T. Local myocardial insulin-like growth factor 1 (IGF-1) delivery with biotinylated peptide nanofibers improves cell therapy for myocardial infarction. *Proc Nat Acad Sci USA* 103:8155-8160, 2006

364. Torella D, Rota M, Nurzynska D, Musso E, Monsen A, Shiraishi 1, Zias E, Walsh K, Rosenzweig A, Sussman M A, Urbanek K, Nadal-Ginard B, Kajstura J, Leri A, Anversa P. Cardiac stem cell and myocyte aging, heart failure, and insulin like growth factor-1 overexpression. *Circ Res* 94:411-413, 2004.

365. Dawn B, Guo Y, Rezazzadeh A, Huang Y, Stein A B, Hunt G. Tiwari S, Varma J, Gu Y, Prabhu S D, Kajstura J, Anversa P, Ildstad S T, Bolli R. Postinfarction cytokine therapy regenerates cardiac tissue and improves left ventricular function. *Circ Res* 28:990-992, 2006.

366. Liu J, Hu Q, Wang Z, Xu C, Wang X, Gong G, Mansoor A, Lee J, Hou M, Zeng L, Zhang J R, Jerosch-Herold M, Guo T, Bache R J, Zhang J. Autologous stem cell transplantation for myocardial repair. *Am J Physiol* 287:H501-H511, 2004.

367. Zeng L, Hu Q, Wang X, Mansoor A, Lee J, Feygin J, Zhang G, Suntharalingam P, Boozer S, Mhashilkar A, Panetta C J, Swingen C, Deans R, From A H L, Bache R J, Verfaille C M, Zhang J. Bioenergetic and functional consequences of bone marrow-derived multipotent progenitor cell transplantation in hearts with postinfarction left ventricular remodeling. *Circulation* 115:1866-1875, 2007.

368. Suzuki G, Lee T C, Fallviollitta J A, Canty J M. Adenoviral gene transfer of FGF-5 to hibernating myocardium improves function and stimulates myocytes to hypertrophy and reenter the cell cycle. *Circ Res* 96:767-775, 2005.

369. Tillmanns J, Rota M. Hosoda T, Rotatori F, DeAngelis A, Amano K, Amano S, LeCapitaine N, Esposito G, Loredo M, Misao Y, Vitale S, Bearzi C, Urbanek K. Bolli R, Leri A, Kajstura J, Anversa P: Formation of large coronary arteries by cardiac stem cells: a biological bypass. Proc Natl Acad Sci USA. In revision, 2007.

370. Moore K A, Lemischka I R. Stem cells and their niches. *Science*. 2006; 311:1880-1885.

371. Yin T, Li L. The stem cell niches in bone. *J Clin Invest*. 2006; 116:1195-1201.

372. Scadden D T. The stem-cell niche as an entity of action. *Nature*. 2006; 441:1075-1079.

373. Braun K M, Niemann C, Jensen U B, Sundberg P, Silva-Vargas V, Watt F M. Manipulation of stem cell proliferation and lineage commitment: visualization of label-retaining cells in whole mounts of mouse epidermis. Development. 2003; 130:5241-5255.

374. Tumbar T, Guasch G, Greco V, Blanpain C. Lowry W E, Rendl M, Fuchs E. Defining the epithelial stem cell niche in skin. *Science*. 2004; 303:359-363.

375. Watt F M, Hogan B L M. Out of Eden: stem cells and their niches. *Science*. 2000; 287:1427-1438.

376. Spradling A, Drummond-Barbosa D, Kai T. Stem cells find their niche. *Nature*. 2001; 414:98-104.

377. Gotz M, Huttner W B. The cell biology of neurogenesis. *Nat Rev Mol Cell Biol*. 2005; 6:777-788.

378. Fuchs E, Tumbar T, Guasch G. Socializing with the neighbors: stem cells and their niche. *Cell*. 2004; 116:769-778.

379. Urbanek K, Cesselli D, Rota M, Nascimbene A, De Angelis A, Hosoda T, Bearzi C, Boni A, Bolli R, Kajstura J, Anversa P, Leri A. Stem cell niches in the adult mouse heart. *Proc Natl Acad Sci USA*. 2006; 103:9226-31.

380. Perez-Moreno M, Jamora C, Fuchs E. Sticky business: orchestrating cellular signals at adherens junctions. *Cell*. 2003; 121:535-548.

381. Goldberg G S, Valiunas V, Bring P R. Selective permeability of gap junction channels. *Biochim Biophys Acta*. 2004; 1662:96-101.

382. Wei C-J, Xu X, Lo C W. Connexins and cell signaling in development and disease. *Annu Rev Cell Dev Biol* 2004; 20:811-38.

383. Lockhart D J, Dong H, Byrne M C. Follettie M T, Gallo M V, Chee M S, Mittmann M, Wang C, Kobayashi M, Horton H, Brown E L. Expression monitoring by hybridization to high-density oligonucleotide arrays. *Nat Biotechnol*. 1996; 14:1675-80.

384. Li C, Wong W H. Model-based analysis of oligonucleotide arrays: expression index computation and outlier detection. *Proc Natl Acad Sci USA*. 2001; 98:31-36.

385. Bhattacharya B, Miura T, Brandenberger R, Mejido J, Luo Y, Yang A X, Joshi B H, Ginis I, Thies R S, Amit M, Lyons I, Condie B G, Itskovitz-Eldor J, Rao M S, Puri Rk. Gene expression in human embryonic stem cell lines: unique molecular signature. *Blood*. 2004; 103:2956-64.

386. Bruno L, Hoffmann R, McBlane F. Brown J, Gupta R, Joshi C, Pearson S, Seidl T, Heyworth C, Enver T. Molecular signatures of self-renewal, differentiation, and lineage choice in multipotential hemopoietic progenitor cells in vitro. *Mol Cell Biol*. 2004; 24:741-56.

387. Ivanova N B, Dimos J T, Schaniel C, Hackney J A, Moore K A, Lemischka I R. A stem cell molecular signature. *Science*. 2002; 298:601-604.

388. Ramalho-Santos M S, Yoon Y, Matsuzxaki R, Mulligan C, Melton D A. "Stemness" transcriptional profiling of embryonic and adult stem cells. *Science*. 2002; 298:597-600.

389. Sturn A, Quackenbush J, Trajanoski. Genesis: cluster analysis of microarray data. *Bioinformatics*. 2002; 18:207-08.

390. Kuroda T, Tada M, Kubota H, Kimura H, Hatano S Y, Suemori H, Nakatsuji N, Tada T. Octamer and Sox elements are required for transcriptional cis regulation of Nanog gene expression. *Mol Cell Biol.* 2005; 25:2475-85.

391. Rodda D J, Chew J L, Lim L H, Loh Y H, Wang B, Ng H H, Robson P. Transcriptional regulation of nanog by OCT4 and SOX2. *J Biol Chem.* 2005; 280:24731-7.

392. Player A, Wang Y, Bhattacharya B, Rao M, Puri R K, Kawasaki E S. Comparisons between transcriptional regulation and RNA expression in human embryonic stem cell lines. *Stem Cells Dev.* 2006: 15:315-23.

393. Stains J P, Civitelli R. Genomic approaches to identifying transcriptional regulators of osteoblast differentiation. *Genome Biol.* 2003; 4:222.

394. Rao R R, Stice F L. Gene expression profiling of embryonic stem cells leads to greater understanding of pluripotency and early developmental events. *Biol Reprod.* 2004; 71:1772.

395. Terskikh A V, Miyamoto T, Chang C, Diatchenko L, Weissman I L. Gene expression analysis of purified hematopoietic stem cells and committed progenitors. *Blood.* 2003; 102:94-101.

396. Komor M, Guller S, Baldus C D, de Vos S, Hoelzer D, Ottmann O G, Hofmann W K. Transcriptional profiling of human hematopoiesis during in vitro lineage-specific differentiation. *Stem Cells.* 2005; 23:1154-69.

397. Cheng L C. Tavaoie M, Doetsch F. Stem cells: from epigenetics to microRNAs. *Neuron.* 2005; 46:363-7.

398. Ko M S, McLaren A. Epigenetics of germ cells, stem cells, and early embryos. *Dev Cell.* 2006; 10:161-6.

399. Shivdasani R A. MicroRNAs: regulators of gene expression and cell differentiation. *Blood.* 2006 [Epub ahead of print].

400. Lee M S, Jun D H, Hwang C I, Park S S, Kang J J, Park H S, Kim J, Kim J H, Seo J S, Park W Y. Selection of neural differentiation-specific genes by comparing profiles of random differentiation. *Stem Cells.* 2006; 24:1946-55.

401. Assmus B, Honold J, Schachinge V, Brittenn M B, Fischer-Rasokat U. Lehmann R, Teupe C, Pistorius K, Martin H, Abolmaai N D, Tonn T, Dimmler S, Zeiher A M. Transcoronary transplantation of progenitor cells after myocardial infarction. *N Engl Med* 355:1189-1191, 2006; 355:1274-1277, 2006

402. Baserga R. The biology of cell reproduction. Harvard University Press. 1985

403. Chen S, Lecleider R J. Transforming growth factor-beta-induced differentiation of smooth muscle from a neural crest stem cell line. *Circ Res.* 2004; 94:1195-1202.

404. Bruhl T, Heeschen C, Aicher A, Jadidi A S, Haendeler J, Hoffmann J, Schneider M D, Zeiher A M, Dimmeler S, Rossig L. p21Cip1 levels differentially regulate turnover of mature endothelial cells, endothelial progenitor cells, and in vivo neovascularization. *Circ Res.* 2004; 94:686-692.

405. Brandenberger R, Wei H, Zhang S, Lei S, Murage J, Fisk G J, Li Y, Xu C, Fang R, Guegler K, Rao M S, Mandalam R, Lebkowski J, Stanton L W. Transcriptome characterization elucidates signaling networks that control human ES cell growth and differentiation. *Nat Biotechnol.* 2004; 22:707-716.

406. Ginis I, Luo Y, Miura T, Thies S, Brandenberger R, Gerecht-Nir S, Amit M, Hoke A, Carpenter M K, Itskovitz-Eldor J, Rao M S. Differences between human and mouse embryonic stem cells. *Dev Biol.* 2004; 269:360-380.

407. Brazma A, Hingamp P, Quackenbush J, Sherlock G, Spellman P, Stoeckert C, Aach J, Ansorge W, Ball C A, Causton H C, Gaasterland T, Glenisson P, Holstege F C, Kim I F, Markowitz V, Matese J C, Parkinson H, Robinson A, Sarkans U, Schulze-Kremer S, Stewart J. Taylor R, Vilo J, Vingron M. Minimum information about a microarray experiment (MIAME)-toward standards for microarray data. *Nat Genet.* 2001; 29:365-371.

408. Draghici S, Khatri P, Bhaysar P, Shah A, Krawetz S A, Tainsky M A. Onto-Tools, the toolkit of the modern biologist: Onto-Express, Onto-Compare, Onto-Design and Onto-Translate. *Nucleic Acids Res.* 2003; 31:3775-3781.

409. Urbanek K, Rota M, Cascapera S, Bearzi C, Nascimbene A, De Angelis A, Hosoda T, Chimenti S, Baker M, Limana F, Nurzynska D, Torella D, Rotatori F, Rastaldo R, Musso E, Quaini F, Leri A, Kajstura J, Anversa P. Cardiac stem cells possess growth factor-receptor systems that following activation regenerate the infracted myocardium improving ventricular function and long-term survival. *Circ Res.* 2005; 97:663-673.

410. Wallenstein S, Zucker C L, Fleiss J L. Some statistical methods useful in circulation research. *Circ Res.* 1980; 47:1-9.

411. Berenson M L, Levine D M, Rindskopf D. Applied statistics. Prentice Hall, Englewood Cliffs. Pp. 362-418, 1988.

412. Jeffery I B, Higgins D G, Culhane A C. Comparison and evaluation of methods for generating differentially expressed gene lists from microarray data. *BMC Bioinformatics.* 2006; 7:359.

413. Hack C J. Integrated transcriptome and proteome data: the challenges ahead. *Brief Fund Genomic Proteomic.* 2004; 3:212-219.

414. Ikeno F, Lyons J, Kaneda K, Baluom M, Benet L, Rezaee M. Novel precutaneous adventitial drug delivery system for regional vascular treatment. *Cath. Cardiovasc Interv* 63:222-230, 2004

415. Suematsu N, Ojaimi C, Kinugawa S. Xu X, Koller A, Recchia F A, Hintze T H. Hyperhomocysteinemia alters cardiac substrate metabolism by impairing NO bioavailability through oxidative stress. *Circulation.* 115:255-262, 2007.

416. Bernstein R D, Zhang X, Zhao G, Forfia P R, Tuzman J, Ochoa M, Vogel T and Hintze T H. Mechanisms of nitrate accumulation in plasma during pacing induced heart failure in conscious dogs. *Nitric oxide biology and Chemistry* 1:386-396, 1998.

417. Recchia F A, McConnell P I, Bernstein R D, Vogel T R, Xu X B and Hintze T H. Reduced nitric oxide production and altered myocardial metabolism during the decompensation of pacing-induced heart failure in the conscious dog. *Circ Res* 83:969-979, 1998.

418. Post H, d'Agostino C, Lionette V, Castellari M, Kang E Y, Altarejos M, X B Xu, T H Hintze, Recchia F A. Reduced left ventricular compliance and mechanical efficiency after prolonged inhibition of NO synthesis in conscious dogs. *J Physiol.* 552:233-239, 2003.

419. Erbs S, Linke A, Schachinger V, Assmus B, Thiele H, Diederich K W, Hoffmann C, Dimmler S, Tonn T, Hambrecht R, Zeiher A M, Schuler G. Restoration of microvascular function in infarct-related artery by intracoronary transplantation of bone marrow progenitor cells in patients with acute myocardial infarction: the Doppler substudy of Reinfarction of Enriched Progenitor cells and Infarct Remodeling in Acute Myocardial Infarction (REPAIR-AM1) trial. *Circulation* 116:366-374, 2007

420. Stewart J M, Wang J, Zeballos G A, Dean R, Schustek M, Ochoa M, Hintze T H. Bilaterial atriectomy eliminates atrial peptide release during volume expansion in conscious dogs. *Circ. Res.* 70:724-732, 1992.

421. Shen W Q, Xu X, Wang J, Ochoa M, Zeballos G A, Schustek M, Stewart J M, Hintze T H. Contribution of the ventricles and atrial appendages to the elevation of plasma ANF during congestive heart failure in conscious dogs. *Basic Res Cardio* 41:319-328, 1996.

422. Lei B, Matsuo K, Labinsky V, Sharma N, Chandler M P, Ahn A, Hintze T H, W C Stanley and F A Recchia. Exogeneous nitric oxide reduces glucose transporters translocation and lactate production in ischemic myocardium, in vivo *PNAS.* 102:6966-6971, 2005

423. Millard R W, Baig H, Vatner S F. Cardiovascular effects of radioactive microsphere suspensions and Tween 80 solutions. *Am J Physiol* 232:H331-H334, 1977

424. Sun D, Huang A, Zhao G, Bernstein R, Forfia P, Xu X, Koller A, Kaley G, Hintze T H. Reduced NO-dependent arteriolar dilation during the development of cardiomyopathy. *Am. J. Physiol.* Heart Circ. Physiol. 278: H461-H468, 2000

425. Sun D, Huang A, Mital S Kichuk M R, Marboe C, Addonizio L J, Muhler R E, Koller A, Hintze T G, Kaley G. Norepinephrine elicits B2 receptor mediated dilation of isolated human coronary arterioles. *Circulation.* 106:550-555, 2002.

426. Lavallee M, Vatner S F. Regional myocardial blood flow and necrosis in primates following coronary occlusion. *Am J Physiol* 246:H635-11639, 1984.

The invention claimed is:

1. A method for generating a biological bypass in a subject in need thereof comprising:
    selecting cardiac progenitor cells that express vascular endothelial growth factor receptor 2 (VEGFR-2) from a population of c-kit positive, lineage negative, CD34 negative cardiac progenitor cells extracted from myocardial tissue obtained from the subject, thereby obtaining isolated vascular progenitor cells; and
    administering an effective dose of said isolated vascular progenitor cells to a stenotic or occluded artery in the subject's heart, wherein the vascular progenitor cells differentiate into endothelial cells and/or smooth muscle cells, thereby forming coronary vessels that reestablish blood flow to the myocardium.

2. The method of claim 1, wherein the coronary vessels have diameters ranging from about 6 μm to about 2 mm.

3. The method of claim 1, wherein the coronary vessels include coronary arteries, arterioles, and capillaries.

4. The method of claim 3, wherein the coronary arteries are at least 500 μm in diameter.

5. The method of claim 1, wherein the vascular progenitor cells are administered by a catheter.

6. The method of claim 1, wherein the subject is human.

7. A method for restoring structural and functional integrity to damaged myocardium in a subject in need thereof comprising:
    selecting cardiac progenitor cells that express VEGFR-2 from a population of c-kit positive, lineage negative, CD34 negative cardiac progenitor cells extracted from myocardial tissue obtained from the subject, thereby obtaining isolated vascular progenitor cells; and
    administering an effective dose of said isolated vascular progenitor cells to the damaged myocardium, wherein the vascular progenitor cells differentiate into endothelial cells and smooth muscles cells forming functional coronary vessels, thereby increasing blood flow to the damaged myocardium.

8. The method of claim 7, wherein said effective dose of isolated vascular progenitor cells is about $2 \times 10^4$ to about $2 \times 10^7$.

9. The method of claim 7 further comprising administering an effective dose of isolated myocyte progenitor cells to the damaged myocardium, wherein said myocyte progenitor cells are lineage negative, c-kit positive, VEGFR-2 negative, and CD34 negative, and wherein the myocyte progenitor cells differentiate into cardiomyocytes forming functional myocardium, thereby increasing contractile function.

10. The method of claim 9, wherein said myocyte progenitor cells are isolated from myocardial tissue obtained from the subject.

11. The method of claim 9, wherein the myocyte progenitor cells are administered simultaneously with the vascular progenitor cells.

12. The method of claim 11, wherein the vascular progenitor cells and myocyte progenitor cells are administered in a ratio of 1:20 to 20:1.

13. The method of claim 11, wherein the vascular progenitor cells and myocyte progenitor cells are administered in a ratio of 1:1.

14. The method of claim 9, wherein the myocyte progenitor cells are administered at a specified time interval after the vascular progenitor cells.

15. The method of claim 14, wherein the myocyte progenitor cells are administered after the vascular progenitor cells have generated functional coronary vessels.

16. The method of claim 9, wherein the vascular progenitor cells and myocyte progenitor cells are administered by a catheter.

17. The method of claim 16, wherein the vascular progenitor cells and myocyte progenitor cells are administered to the border zone of the damaged myocardium.

18. The method of claim 9, wherein the vascular progenitor cells and myocyte progenitor cells are administered by an intracoronary route of administration.

19. The method of claim 9, wherein the damaged myocardium is an infarct.

20. The method of claim 19, wherein the vascular progenitor cells and myocyte progenitor cells are administered to the middle of the infarct.

21. The method of claim 7, wherein the subject is human.

22. The method of claim 1, wherein said isolated vascular progenitor cells are administered by an intracoronary route of administration.

23. The method of claim 1, wherein said effective dose of isolated vascular progenitor cells is about $2 \times 10^4$ to about $2 \times 10^7$.

24. The method of claim 1, wherein more than one effective dose of isolated vascular progenitor cells is administered to the stenotic or occluded artery.

25. The method of claim 1, wherein said isolated vascular progenitor cells are exposed to one or more cytokines prior to administration.

26. The method of claim 25, wherein said one or more cytokines is insulin-like growth factor-1, hepatocyte growth factor, or a combination thereof.

27. The method of claim 9, wherein said effective dose of isolated myocyte progenitor cells is about $2 \times 10^4$ to about $2 \times 10^7$.

28. The method of claim 9, wherein more than one effective dose of isolated vascular progenitor cells and/or isolated myocyte progenitor cells is administered to the damaged myocardium.

29. The method of claim 9, wherein said isolated vascular progenitor cells and/or said myocyte progenitor cells are exposed to one or more cytokines prior to administration.

30. The method of claim 29, wherein said one or more cytokines is insulin-like growth factor-1, hepatocyte growth factor, or a combination thereof.

31. The method of claim 1, further comprising expanding said isolated vascular progenitor cells in culture to obtain a pure population of vascular progenitor cells prior to administration to the subject.

32. The method of claim 7, further comprising expanding said isolated vascular progenitor cells in culture to obtain a pure population of vascular progenitor cells prior to administration to the subject.

* * * * *